(12) United States Patent
Ophardt et al.

(10) Patent No.: US 10,368,701 B2
(45) Date of Patent: *Aug. 6, 2019

(54) RESERVOIR WITH REMOVABLE MOBILE DISPENSER

(71) Applicant: OP-Hygiene IP GmbH, Niederbipp (CH)

(72) Inventors: Heiner Ophardt, Arisdorf (CH); David R. Duncan, St. Catharines (CA)

(73) Assignee: OP-Hygiene IP GmbH, Niederbipp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,136

(22) Filed: May 15, 2018

(65) Prior Publication Data

US 2018/0255980 A1 Sep. 13, 2018

Related U.S. Application Data

(63) Continuation of application No. 15/051,319, filed on Feb. 23, 2016, now Pat. No. 9,993,119.

(30) Foreign Application Priority Data

Feb. 24, 2015 (CA) ..................................... 2882828
Feb. 4, 2016 (CA) ..................................... 2919940

(51) Int. Cl.
*A47K 5/12* (2006.01)
*B65B 3/12* (2006.01)
*B05B 11/00* (2006.01)
*G16H 40/20* (2018.01)

(52) U.S. Cl.
CPC .......... *A47K 5/1211* (2013.01); *A47K 5/1201* (2013.01); *A47K 5/1205* (2013.01);
(Continued)

(58) Field of Classification Search
CPC .. A47K 5/1211; A47K 5/1201; A47K 5/1205; A47K 5/1207; B05B 11/0054; B05B 11/0056; B05B 11/3014
(Continued)

(56) References Cited

U.S. PATENT DOCUMENTS 5,427,279 A 6/1995 Kaufman
5,740,948 A 4/1998 Chu et al.
(Continued)

FOREIGN PATENT DOCUMENTS

GB 2495716 4/2013
WO WO 2010094963 8/2010

*Primary Examiner* — Paul R Durand
*Assistant Examiner* — Michael J. Melaragno
(74) *Attorney, Agent, or Firm* — Thorpe North and Western LLP

(57) ABSTRACT

A replaceable cartridge for a liquid master dispenser is disclosed. The replaceable cartridge includes a reservoir for containing liquid to be dispensed from the liquid master dispenser; and a personal dispenser removably coupled to the reservoir. The personal dispenser includes a receptacle for containing liquid to be dispensed from the personal dispenser; and an outlet port for discharge of the liquid from the receptacle. The personal dispenser is configured for selectively discharging the liquid contained in the receptacle from the outlet port, after the personal dispenser is removed from the reservoir. The reservoir has a cavity sized for removably receiving the personal dispenser.

20 Claims, 39 Drawing Sheets

(52) U.S. Cl.
CPC ........ *A47K 5/1207* (2013.01); *B05B 11/0054* (2013.01); *B05B 11/0056* (2013.01); *B05B 11/3014* (2013.01); *B65B 3/12* (2013.01); *B05B 11/3057* (2013.01); *G16H 40/20* (2018.01); *Y02A 90/22* (2018.01)

(58) Field of Classification Search
USPC .......................................................... 22/175
See application file for complete search history.

(56) References Cited

U.S. PATENT DOCUMENTS

| | | |
|---|---|---|
| 5,836,482 A | 11/1998 | Ophardt et al. |
| 7,748,573 B2 | 7/2010 | Ophardt et al. |
| 7,984,825 B2 | 7/2011 | Ophardt et al. |
| 8,684,236 B2 | 4/2014 | Ophardt |
| 9,993,119 B2 * | 6/2018 | Ophardt ............... A47K 5/1205 |
| 2004/0140326 A1 | 7/2004 | Smart et al. |
| 2004/0149779 A1 | 8/2004 | Boll et al. |
| 2008/0110936 A1 | 5/2008 | Ophardt |
| 2008/0251539 A1 | 10/2008 | Yapaola et al. |
| 2009/0045221 A1 | 2/2009 | Ophardt et al. |
| 2010/0219206 A1 | 9/2010 | Ophardt |
| 2010/0288788 A1 | 11/2010 | Ophardt |
| 2012/0158193 A1 | 6/2012 | De Rosa et al. |
| 2012/0279987 A1 | 11/2012 | Ophardt et al. |
| 2013/0019992 A1 | 1/2013 | Feriani et al. |
| 2013/0068791 A1 | 3/2013 | Pelfrey et al. |
| 2014/0230960 A1 | 8/2014 | Ciavarella et al. |
| 2014/0253336 A1 | 9/2014 | Ophardt |

\* cited by examiner

RESERVOIR WITH REMOVABLE MOBILE DISPENSER

RELATED APPLICATION

This application is a continuation of co-pending U.S. patent application Ser. No. 15/051,319 filed Feb. 23, 2016 and claims the benefit of 35 U.S.C. 120.

FIELD OF THE INVENTION

This invention relates to devices that dispense hand cleaning fluids, or other liquids. More particularly, the invention relates to a liquid master dispenser having a removable personal or point of care dispenser for providing a mobile supply of the liquid.

BACKGROUND OF THE INVENTION

The importance of regular hand cleaning in reducing the spread of infectious disease is well known. To encourage frequent hand cleaning, it is becoming increasingly common in health care facilities to incorporate prominent hand cleaning stations at entrances and exits, as well as at other locations throughout. The hand cleaning stations are typically provided with devices for dispensing hand cleaners such as soap or hand sanitizer, which may be manually operated or touchlessly operated.

It is also becoming increasingly common for individuals to carry a supply of hand cleaner in a mobile personal or point of care dispenser, to facilitate hand cleaning when away from a hand cleaning station. This is particularly prevalent in the health care industry, where frequent hand cleaning is essential. Mobile personal or point of care dispensers are often small squeezable containers, which may be deposited in a pocket or clipped to an item of clothing for easy access, or may be placed for use at a point of care.

Despite the increasing awareness of the importance of frequent hand cleaning, the spread of infections in settings such as hospitals and long term care facilities remains problematic. To further combat the spread of infections, some institutions have begun implementing measures for tracking the hand cleaning activity of health care workers. For example, compliance systems may include monitoring hand cleaning and the use of hand cleaners. The present inventors have appreciated that previously known dispensing systems do not provide arrangements for conveniently monitoring the use of cleaners in personal dispensers or for the filling of personal dispensers.

The inventors of this application have appreciated that previously known devices do not integrate the functions of stationary dispensers and mobile dispensers.

SUMMARY OF THE INVENTION

To at least partially overcome some of the disadvantages of previously known devices, the invention provides a liquid master dispenser that incorporates a removable mobile personal, or point of care, dispenser. The personal dispenser is configured to removably couple to the liquid master dispenser to receive liquid therefrom. The personal dispenser can then be removed and carried to a location remote from the master dispenser, where the liquid in the personal dispenser can be dispensed as needed. In preferred embodiments, the liquid master dispenser is able to dispense the liquid, as for example onto a user's hands, both while the personal dispenser is coupled to the master dispenser and while the personal dispenser is removed from the master dispenser.

The inventors have appreciated that, in at least some embodiments, the liquid dispenser of the invention is able to provide the dual functions of: (i) filling and refilling a mobile personal dispenser; and (ii) directly dispensing liquid, as for example onto a user's hands. In at least some preferred embodiments, the integration of a stationary hand cleaner dispenser with a mobile personal dispenser permits simplified tracking of hand cleaning compliance to take into account the cleaner dispensed from the personal dispenser.

In one embodiment, the liquid master dispenser of the invention incorporates a reservoir for containing the liquid to be dispensed, and a dispenser outlet for discharge of the liquid from the reservoir. The liquid master dispenser also incorporates a discharge mechanism, such as a manually or electronically activated pump assembly, which is operable to discharge the liquid from the dispenser outlet. A personal dispenser is removably coupled to the dispenser outlet, and has a receptacle for containing liquid received from the liquid master dispenser. The personal dispenser is provided with an outlet port from which the liquid contained in the receptacle may be discharged.

While the personal dispenser is coupled to the dispenser outlet, the liquid discharged from the dispenser outlet accumulates in the receptacle. As the liquid accumulates, the air displaced thereby may, for example, be expelled from the receptacle via the outlet port or a separate pressure relief valve.

The personal dispenser is configured so that, once the volume of the liquid contained within the receptacle reaches a preselected threshold amount, the receipt of further liquid from the master dispenser causes liquid contained within the personal dispenser to be discharged from the outlet port. This may be achieved, for example, by incorporating a baffle wall into the receptacle which prevents the accumulated liquid from reaching the outlet port until the level of the liquid within the receptacle exceeds the height of the baffle wall. Preferably, the height of the baffle wall is selected so that the receptacle must be nearly full before any liquid is expelled from the outlet port.

The personal dispenser may be removed from the master dispenser at any time, and carried manually to locations remote from the master dispenser. While removed from the master dispenser, the personal dispenser is configured to permit the discharge of liquid contained within the receptacle from the outlet port, to provide a supply of the liquid while away from the master dispenser. This may be achieved, for example, by configuring the receptacle to be manually compressible, so that the liquid is discharged from the outlet port when the personal dispenser is squeezed. While the personal dispenser is removed from the master dispenser, the discharge mechanism of the master dispenser remains operable, so that the liquid contained in the reservoir can be directly discharged from the dispenser outlet.

In another embodiment, the present invention provides a replaceable cartridge for a liquid master dispenser. The replaceable cartridge provides a supply of the liquid to be dispensed, and is configured to be installed in the master dispenser to dispense the liquid therefrom. The cartridge can be removed from the master dispenser and replaced as required. The cartridge includes a reservoir having a reservoir outlet, and a personal dispenser removably coupled to the reservoir outlet. The personal dispenser has a receptacle for containing liquid discharged from the reservoir outlet, and an inlet port for receiving the liquid discharged from the reservoir outlet. An outlet port of the personal dispenser is provided for discharging the liquid from the receptacle.

Preferably, the replaceable cartridge includes a pump assembly disposed across the reservoir outlet that is configured to discharge the liquid from the reservoir upon application of a mechanical force. The mechanical force may be provided, for example, by an actuator carried by a housing of the master dispenser.

Preferably in some embodiments, the personal dispenser is configured to accumulate the liquid received from the reservoir until a preselected volume of the liquid is contained therein, at which point the receipt of further liquid from the reservoir causes discharge of the liquid from the outlet port. The personal dispenser is furthermore removable from the reservoir, and may be carried to locations remote from the master dispenser to selectively discharge the liquid contained therein.

In a further embodiment, the invention provides a refillable personal dispenser for dispensing liquid. The personal dispenser includes a receptacle for containing the liquid, and a coupling mechanism for releasably coupling the personal dispenser to a master dispenser. The personal dispenser also includes an inlet port for receiving liquid discharged from the master dispenser while the personal dispenser is coupled thereto, and an outlet port for discharge of the liquid from the receptacle. The inlet port preferably incorporates a one-way inlet valve that permits fluid to enter the receptacle through the inlet port, and prevents fluid from exiting the receptacle through the inlet port. The outlet port likewise preferably incorporates a one-way outlet valve that permits fluid to exit the receptacle through the outlet port, and prevents fluid from entering the receptacle through the outlet port.

The personal dispenser is preferably configured to accumulate the liquid received from the reservoir until a preselected volume is reached, after which the liquid is discharged from the outlet port when further liquid is received from the reservoir. The personal dispenser is also configured to permit the selective discharge of the liquid contained in the receptacle while uncoupled from the reservoir.

In one embodiment of the invention, a liquid master dispenser is provided that incorporates a reservoir, a dispenser outlet, and a discharge mechanism similar to those described above, and which further includes a separate refill outlet configured to couple with a personal dispenser and deliver liquid from the reservoir to the personal dispenser upon activation of a separate filling mechanism.

Preferably, the liquid dispenser incorporates a usage monitoring system which records the amount of liquid that has been dispensed from both the dispenser outlet and the refill outlet. This ensures that the usage monitoring system takes into account the liquid that is used to fill the personal dispenser, and not just the liquid that is directly dispensed from the dispenser outlet. As such, the usage monitoring system is able to create a more complete record of liquid usage, which may for example be particularly useful in monitoring hand cleaning compliance in a health care setting.

Accordingly, in one aspect the present invention resides in a liquid master dispenser, comprising:

a reservoir for containing liquid to be dispensed;

a dispenser outlet for discharge of the liquid from the reservoir;

a discharge mechanism operable to discharge the liquid from the dispenser outlet when activated; and a personal dispenser removably coupled to the dispenser outlet, the personal dispenser comprising a receptacle for containing the liquid and an outlet port for discharge of the liquid from the receptacle;

wherein:

(a) while the personal dispenser is coupled to the dispenser outlet, the liquid discharged from the dispenser outlet accumulates in the receptacle until the receptacle contains a preselected volume of the liquid, and once the receptacle contains the preselected volume of the liquid, the discharge of further said liquid from the dispenser outlet causes the liquid contained in the receptacle to be discharged from the outlet port; and (b) while the personal dispenser is removed from the dispenser outlet:

(i) the personal dispenser is configured to be carried manually to locations remote from the master dispenser for selectively discharging the liquid contained in the receptacle from the outlet port; and (ii) the discharge mechanism is operable to discharge the liquid contained in the reservoir from the dispenser outlet.

In another aspect, the present invention resides in a replaceable cartridge for a liquid master dispenser, comprising:

a reservoir for containing liquid to be dispensed, the reservoir having a reservoir outlet for selective discharge of the liquid from the reservoir; and a personal dispenser removably coupled to the reservoir outlet, the personal dispenser comprising:

a receptacle for containing the liquid discharged from the reservoir outlet;

an inlet port for receiving the liquid discharged from the reservoir outlet and communicating the liquid to the receptacle; and an outlet port for discharge of the liquid from the receptacle;

wherein the reservoir outlet is configured to permit the selective discharge of the liquid from the reservoir while the personal dispenser is removed from the reservoir outlet;

wherein the personal dispenser is configured so that, while the personal dispenser is coupled to the reservoir outlet, the liquid discharged from the reservoir outlet accumulates in the receptacle until the receptacle contains a preselected volume of the liquid, and once the receptacle contains the preselected volume of the liquid, the discharge of further said liquid from the reservoir outlet causes the liquid contained in the receptacle to be discharged from the outlet port; and wherein the personal dispenser is configured for selectively discharging the liquid contained in the receptacle from the outlet port, after the personal dispenser is removed from the reservoir outlet.

In a further aspect, the present invention resides in a refillable personal dispenser for dispensing liquid, comprising:

a receptacle for containing the liquid;

a coupling mechanism for releasably coupling to a reservoir;

an inlet port for receiving the liquid from the reservoir and communicating the liquid to the receptacle; and an outlet port for discharge of the liquid from the receptacle;

wherein the outlet port is configured so that, while the personal dispenser is coupled to the reservoir, the liquid received by the inlet port accumulates in the receptacle until the receptacle contains a preselected volume of the liquid; and once the receptacle contains the preselected volume of the liquid, the outlet port is configured to discharge the liquid contained in the receptacle upon receipt of further said liquid by the inlet port;

wherein the inlet port comprises a one-way inlet valve that permits fluid to enter the receptacle through the inlet port, and prevents fluid from exiting the receptacle through the inlet port; and wherein the receptacle defines an internal volume and is compressible to selectively reduce the internal volume from an uncompressed volume to a compressed volume upon application of a compressing force, to thereby discharge the liquid from the outlet port.

In a still further aspect, the present invention resides in a liquid dispenser, comprising:

a reservoir for containing liquid to be dispensed;

a dispenser outlet for discharge of the liquid from the reservoir;

a discharge mechanism operable to discharge the liquid from the dispenser outlet when activated;

a refill outlet configured to couple with a personal dispenser and deliver the liquid from the reservoir to the personal dispenser; and a filling mechanism operable to deliver the liquid from the refill outlet when activated.

In yet another aspect, the present invention resides in a hand cleaning liquid master dispenser, comprising:

a reservoir for containing liquid to be dispensed;

a discharge mechanism operable to discharge the liquid from the reservoir when activated; and a personal dispenser removably coupled to the master dispenser, the personal dispenser comprising a receptacle for containing the liquid and an outlet port for discharge of the liquid from the receptacle;

wherein:

(a) while the personal dispenser is coupled to the master dispenser, the discharge mechanism discharges the liquid from the reservoir into the receptacle and the liquid discharged accumulates in the receptacle until the receptacle contains a preselected volume of the liquid, and while the receptacle contains the preselected volume of the liquid, the discharge mechanism discharges the liquid from a dispenser outlet; and (b) while the personal dispenser is removed from the master dispenser:

(i) the personal dispenser is configured to be carried manually to locations remote from the master dispenser for selectively discharging the liquid contained in the receptacle from the outlet port; and (ii) the discharge mechanism is operable to discharge the liquid contained in the reservoir from the dispenser outlet.

Further aspects of the invention include:

1. A liquid dispenser, comprising:
a reservoir for containing liquid to be dispensed;
a dispenser outlet for discharge of the liquid from the reservoir; and
a discharge mechanism operable to discharge the liquid from the dispenser outlet when activated;
characterized in that the liquid dispenser further comprises a removable personal dispenser, wherein the liquid dispenser is configured to deliver the liquid from the reservoir to the personal dispenser.

2. A liquid dispenser, optionally including one or more features of 1, characterized in that the liquid dispenser further comprises a usage monitoring system configured to generate information indicative of an amount of the liquid dispensed from the liquid dispenser, wherein said amount includes the liquid dispensed from the dispenser outlet and the liquid delivered to the personal dispenser.

3. A liquid dispenser, optionally including one or more features of any of 1 to 2, characterized in that the personal dispenser is removably coupled to the dispenser outlet.

4. A liquid dispenser, optionally including one or more features of any of 1 to 3, characterized in that the personal dispenser comprises a receptacle for containing the liquid and an outlet port for discharge of the liquid from the receptacle;

wherein:

(a) while the personal dispenser is coupled to the dispenser outlet, the liquid discharged from the dispenser outlet accumulates in the receptacle until the receptacle contains a preselected volume of the liquid, and once the receptacle contains the preselected volume of the liquid, the discharge of further said liquid from the dispenser outlet causes the liquid contained in the receptacle to be discharged from the outlet port; and (b) while the personal dispenser is removed from the dispenser outlet:

(i) the personal dispenser is configured to be carried manually to locations remote from the dispenser outlet for selectively discharging the liquid contained in the receptacle from the outlet port; and (ii) the discharge mechanism is operable to discharge the liquid contained in the reservoir from the dispenser outlet.

5. A liquid dispenser, optionally including one or more features of any of 1 to 4, characterized in that the personal dispenser includes an inlet port for receiving the liquid discharged from the dispenser outlet and communicating the liquid to the receptacle; the personal dispenser coupled to the dispenser outlet with the dispenser outlet engaged with the inlet port;

wherein the inlet port comprises a one-way inlet valve that permits fluid to enter the receptacle through the inlet port, and prevents fluid from exiting the receptacle through the inlet port;

wherein the outlet port comprises a one-way outlet valve that permits fluid to exit the receptacle through the outlet port, and prevents fluid from entering the receptacle through the outlet port; and wherein the receptacle defines an internal volume and is compressible to selectively reduce the internal volume from an uncompressed volume to a compressed volume upon application of a compressing force, to thereby discharge the liquid from the outlet port.

6. A liquid dispenser, optionally including one or more features of any of 1 to 5, characterized in that the discharge mechanism is configured to permit the liquid to be drawn from the reservoir out the dispenser outlet through application of a vacuum pressure to the dispenser outlet;

wherein the personal dispenser comprises a dispensing mechanism operable, while the personal dispenser is coupled to the dispenser outlet, to create the vacuum pressure to draw the liquid from the reservoir, out the dispenser outlet, and into the receptacle;

wherein the dispensing mechanism is manually operative to create the vacuum pressure;

wherein while the personal dispenser is coupled to the dispenser outlet, the dispenser outlet sealingly engages with the inlet port, placing the dispenser outlet in communication with the receptacle; and wherein the discharge mechanism requires electrical power for operation, and while the personal dispenser is coupled to the dispenser outlet, if the electrical power required for operation of the discharge mechanism is not available, operation of the dispensing mechanism draws the liquid from the reservoir, out the dispenser outlet, into the receptacle, and when the receptacle contains the preselected volume of the liquid, out the outlet port.

7. A liquid dispenser, optionally including one or more features of any of 1 to 6, characterized in that the receptacle comprises:

an internal chamber having an open end for receiving and expelling the liquid therefrom; and a manually compressible diaphragm defining one side of the internal chamber;

wherein the personal dispenser is configured so that compression of the diaphragm effects the discharge of the liquid from the outlet port;

wherein the internal chamber is configured so that, while the personal dispenser is coupled to the dispenser outlet, the open end is positioned at a designated height above the diaphragm, the designated height corresponding to a level of the liquid within the receptacle when the receptacle contains a designated volume of the liquid, so that the liquid only enters the internal chamber once the receptacle contains the designated volume of the liquid;

wherein the diaphragm is at least partially transparent and is visible to a user to provide a visual indication of whether the internal chamber contains the liquid; and wherein the receptacle further comprises a baffle interposed between the inlet port and the outlet port, for directing the liquid received by the inlet port toward the internal chamber.

8. A liquid dispenser, optionally including one or more features of any of 1 to 7, characterized in that the outlet port comprises an opening in fluid communication with the receptacle;

wherein the personal dispenser is configured so that, while the personal dispenser is coupled to the dispenser outlet, the opening is positioned at a preselected height relative to the receptacle, the preselected height corresponding to a level of the liquid within the receptacle when the receptacle contains the preselected volume of the liquid;

wherein while the personal dispenser is coupled to the dispenser outlet, while the level of the liquid within the receptacle is below the preselected height, the liquid discharged into the receptacle from the dispenser outlet displaces air in the receptacle out the outlet port;

wherein the outlet port comprises a tubular member disposed within the receptacle;

wherein the opening is an inlet opening of the tubular member, and the tubular member extends from the inlet opening to a discharge opening; and wherein the personal dispenser is configured so that, while the personal dispenser is coupled to the dispenser outlet, the discharge opening is positioned below the preselected height.

9. A liquid dispenser, optionally including one or more features of any of 1 to 8, characterized in that the discharge mechanism comprises a pump assembly configured to discharge the liquid from the reservoir upon application of a mechanical force;

wherein the reservoir, the dispenser outlet, the pump assembly, and the personal dispenser together form a replaceable cartridge;

the liquid dispenser further comprising a housing configured to support the replaceable cartridge, the housing carrying an actuator configured to selectively apply the mechanical force to the pump assembly;

wherein the replaceable cartridge is removable from the housing;

wherein the dispenser outlet comprises an outlet tube configured to be received within the inlet port of the personal dispenser, the inlet port removably sealably receiving the outlet tube.

10. A liquid dispenser, optionally including one or more features of any of 1 to 9, characterized in that the liquid dispenser further comprises:

a sensor configured to detect if the personal dispenser is coupled to the dispenser outlet;

a sensor configured to detect if the receptacle contains the preselected volume of the liquid; and a control system that receives information from the sensors and controls the discharge mechanism;

wherein the control system is configured to, upon detecting that the personal dispenser has been coupled to the dispenser outlet, activate the discharge mechanism to discharge the liquid to fill the receptacle when detecting that the receptacle does not contain the preselected volume of the liquid, and to end the activation of the discharge mechanism to fill the receptacle upon detecting that the receptacle contains the preselected volume of the liquid.

11. A liquid dispenser, optionally including one or more features of any of 1 to 10, characterized in that the reservoir has a cavity sized for removably receiving the personal dispenser;

wherein, prior to assembly of the liquid dispenser, the personal dispenser is held within the cavity of the reservoir in an initial bundled configuration;

the liquid dispenser further comprising a label that is secured to a face of the reservoir and a face of the personal dispenser while in the initial bundled configuration;

wherein the label is configured to be severed upon removal of the personal dispenser from the cavity, so as to leave a first portion of the label secured to the face of the reservoir and a second portion of the label secured to the face of the personal dispenser.

12. A liquid dispenser, optionally including one or more features of any of 1 to 11, characterized in that the liquid dispenser further comprises a mounting dock for removably engaging a housing of the personal dispenser for mounting of the personal dispenser;

wherein the mounting dock is positioned so that the personal dispenser is coupled to the dispenser outlet when the housing of the personal dispenser is mounted to the mounting dock.

13. A liquid dispenser, optionally including one or more features of any of 1 to 12, characterized in that the inlet port comprises a one-way inlet valve that permits fluid to enter the receptacle through the inlet port, and prevents fluid from exiting the receptacle through the inlet port;

wherein the outlet port comprises a one-way outlet valve that permits fluid to exit the receptacle through the outlet port, and prevents fluid from entering the receptacle through the outlet port;

wherein the receptacle comprises a collapsible bag that is configured to expand, up to a maximum volume, to accommodate the liquid received by the inlet port;

wherein, once the bag reaches the maximum volume, receipt of further liquid from the inlet port causes pressure within the bag to increase up to a threshold pressure;

wherein the one-way outlet valve is configured to discharge the liquid from the outlet port when the threshold pressure is reached; and wherein the personal dispenser further comprises a plunger that is operable to exert a compressive force on the bag, to increase the pressure within the bag up to the threshold pressure and thereby discharge the liquid from the outlet port.

14. A liquid dispenser, optionally including one or more features of any of 1 to 13, characterized in that the personal dispenser is configured so that the liquid is contained in the receptacle without coming into contact with atmospheric air;

wherein the plunger comprises a manually operable push button;

wherein the personal dispenser comprises a housing defining an internal cavity that extends longitudinally from a first end of the housing to a second end of the housing, the housing having a rack of teeth arranged longitudinally on an internal surface thereof;

wherein the plunger comprises a flexible pawl arranged within the internal cavity, the flexible pawl having a foot that, when in an unbiased state, engages with the teeth;

wherein the bag is arranged within the internal cavity, between the flexible pawl and the first end of the housing;

wherein the foot and the teeth are angled so that:

(i) the foot slides freely along the rack when the plunger is moved longitudinally toward the first end of the housing; and (ii) when the foot is in the unbiased state, the engagement of the foot with the teeth prevents the plunger from being moved longitudinally toward the second end of the housing;

the liquid dispenser further comprising a mounting dock for removably mounting the personal dispenser, the mounting dock being positioned so that the personal dispenser is coupled to the dispenser outlet when the personal dispenser is mounted to the mounting dock;

wherein the mounting dock comprises a protruding rib, and the housing of the personal dispenser has a slot that is sized to receive the protruding rib when the personal dispenser is mounted to the mounting dock;

wherein the protruding rib is configured to engage with the foot when received by the slot, so as to bend the foot away from, and out of engagement with, the rack;

wherein the foot slides freely along the rib when the plunger is moved longitudinally toward the first end of the housing and toward the second end of the housing; and wherein the foot is configured to return to the unbiased state upon removal of the rib from the slot.

15. A liquid dispenser, optionally including one or more features of any of 1 to 14, wherein the liquid comprises a hand cleaning liquid, and the hand cleaning liquid comprises a hand soap or a hand sanitizer.

16. A liquid master dispenser, optionally including one or more features of any of 1 to 15, comprising:

a reservoir for containing liquid to be dispensed;

a dispenser outlet for discharge of the liquid from the reservoir;

a discharge mechanism operable to discharge the liquid from the dispenser outlet when activated; and a personal dispenser removably coupled to the dispenser outlet, the personal dispenser comprising a receptacle for containing the liquid and an outlet port for discharge of the liquid from the receptacle;

wherein:

(a) while the personal dispenser is coupled to the dispenser outlet, the liquid discharged from the dispenser outlet accumulates in the receptacle until the receptacle contains a preselected volume of the liquid, and once the receptacle contains the preselected volume of the liquid, the discharge of further said liquid from the dispenser outlet causes the liquid contained in the receptacle to be discharged from the outlet port; and (b) while the personal dispenser is removed from the dispenser outlet:

(i) the personal dispenser is configured to be carried manually to locations remote from the dispenser outlet for selectively discharging the liquid contained in the receptacle from the outlet port; and (ii) the discharge mechanism is operable to discharge the liquid contained in the reservoir from the dispenser outlet.

17. A liquid master dispenser, optionally including one or more features of any of 1 to 16, further comprising a usage monitoring system configured to generate information indicative of an amount of the liquid dispensed from the liquid dispenser.

18. A liquid master dispenser, optionally including one or more features of any of 1 to 17, wherein the usage monitoring system comprises at least one of:

a sensor configured to detect a volume or a mass of the liquid contained in the reservoir;

a sensor configured to detect a volume or a mass of the liquid contained in the receptacle;

a sensor configured to detect a flow of the liquid through the dispenser outlet;

a sensor configured to detect a flow of the liquid through the outlet port;

a sensor configured to detect the activation of the discharge mechanism; and a sensor configured to detect activation of a dispensing mechanism of the personal dispenser.

19. A liquid master dispenser, optionally including one or more features of any of 1 to 18, wherein the personal dispenser includes an inlet port for receiving the liquid discharged from the dispenser outlet and communicating the liquid to the receptacle; the personal dispenser coupled to the dispenser outlet with the dispenser outlet engaged with the inlet port;

wherein the inlet port comprises a one-way inlet valve that permits fluid to enter the receptacle through the inlet port, and prevents fluid from exiting the receptacle through the inlet port;

wherein the outlet port comprises a one-way outlet valve that permits fluid to exit the receptacle through the outlet port, and prevents fluid from entering the receptacle through the outlet port; and wherein the receptacle defines an internal volume and is compressible to selectively reduce the internal volume from an uncompressed volume to a compressed volume upon application of a compressing force, to thereby discharge the liquid from the outlet port.

20. A liquid master dispenser, optionally including one or more features of any of 1 to 19, wherein the discharge mechanism is configured to permit the liquid to be drawn from the reservoir out the dispenser outlet through application of a vacuum pressure to the dispenser outlet;

wherein the personal dispenser comprises a dispensing mechanism operable, while the personal dispenser is coupled to the dispenser outlet, to create the vacuum pressure to draw the liquid from the reservoir, out the dispenser outlet, and into the receptacle;

wherein the dispensing mechanism is manually operative to create the vacuum pressure;

wherein while the personal dispenser is coupled to the dispenser outlet, the dispenser outlet sealingly engages with the inlet port, placing the dispenser outlet in communication with the receptacle; and wherein the discharge mechanism requires electrical power for operation, and while the personal dispenser is coupled to the dispenser outlet, if the electrical power required for operation of the discharge mechanism is not available, operation of the dispensing mechanism draws the liquid from the reservoir, out the dispenser outlet, into the receptacle, and when the receptacle contains the preselected volume of the liquid, out the outlet port.

21. A liquid master dispenser, optionally including one or more features of any of 1 to 20, wherein the receptacle comprises:

an internal chamber having an open end for receiving and expelling the liquid therefrom; and a manually compressible diaphragm defining one side of the internal chamber;

wherein the personal dispenser is configured so that compression of the diaphragm effects the discharge of the liquid from the outlet port;

wherein the internal chamber is configured so that, while the personal dispenser is coupled to the dispenser outlet, the open end is positioned at a designated height above the diaphragm, the designated height corresponding to a level of the liquid within the receptacle when the receptacle contains a designated volume of the liquid, so that the liquid only enters the internal chamber once the receptacle contains the designated volume of the liquid;

wherein the diaphragm is at least partially transparent and is visible to a user to provide a visual indication of whether the internal chamber contains the liquid; and wherein the receptacle further comprises a baffle interposed between the inlet port and the outlet port, for directing the liquid received by the inlet port toward the internal chamber.

22. A liquid master dispenser, optionally including one or more features of any of 1 to 21, wherein the outlet port comprises an opening in fluid communication with the receptacle;

wherein the personal dispenser is configured so that, while the personal dispenser is coupled to the dispenser outlet, the opening is positioned at a preselected height relative to the receptacle, the preselected height corresponding to a level of the liquid within the receptacle when the receptacle contains the preselected volume of the liquid;

wherein while the personal dispenser is coupled to the dispenser outlet, while the level of the liquid within the receptacle is below the preselected height, the liquid discharged into the receptacle from the dispenser outlet displaces air in the receptacle out the outlet port;

wherein the outlet port comprises a tubular member disposed within the receptacle;

wherein the opening is an inlet opening of the tubular member, and the tubular member extends from the inlet opening to a discharge opening; and wherein the personal dispenser is configured so that, while the personal dispenser is coupled to the dispenser outlet, the discharge opening is positioned below the preselected height.

23. A liquid master dispenser, optionally including one or more features of any of 1 to 22, wherein the discharge mechanism comprises a pump assembly configured to discharge the liquid from the reservoir upon application of a mechanical force;

wherein the reservoir, the dispenser outlet, the pump assembly, and the personal dispenser together form a replaceable cartridge;

the liquid dispenser further comprising a housing configured to support the replaceable cartridge, the housing carrying an actuator configured to selectively apply the mechanical force to the pump assembly;

wherein the replaceable cartridge is removable from the housing;

wherein the dispenser outlet comprises an outlet tube configured to be received in removable sealed engagement within the inlet port of the personal dispenser resisting removal.

24. A liquid master dispenser, optionally including one or more features of any of 1 to 23, further comprising:

a sensor configured to detect if the personal dispenser is coupled to the dispenser outlet;

a sensor configured to detect if the receptacle contains the preselected volume of the liquid; and a control system that receives information from the sensors and controls the discharge mechanism;

wherein the control system is configured to, upon detecting that the personal dispenser has been coupled to the dispenser outlet, activate the discharge mechanism to discharge the liquid to fill the receptacle when detecting that the receptacle does not contain the preselected volume of the liquid, and to end the activation of the discharge mechanism to fill the receptacle upon detecting that the receptacle contains the preselected volume of the liquid.

25. A liquid master dispenser, optionally including one or more features of any of 1 to 24, wherein the reservoir has a cavity sized for removably receiving the personal dispenser;

wherein, prior to assembly of the liquid master dispenser, the personal dispenser is held within the cavity of the reservoir in an initial bundled configuration;

the liquid master dispenser further comprising a label that is secured to a face of the reservoir and a face of the personal dispenser while in the initial bundled configuration;

wherein the label is configured to be severed upon removal of the personal dispenser from the cavity, so as to leave a first portion of the label secured to the face of the reservoir and a second portion of the label secured to the face of the personal dispenser.

26. A liquid master dispenser, optionally including one or more features of any of 1 to 25, further comprising a mounting dock for removably engaging a housing of the personal dispenser;

wherein the mounting dock is positioned so that the personal dispenser is coupled to the dispenser outlet when the housing of the personal dispenser is mounted to the mounting dock.

27. A liquid master dispenser, optionally including one or more features of any of 1 to 26, wherein the receptacle comprises a collapsible bag that is configured to expand, up to a maximum volume, to accommodate the liquid received by the inlet port;

wherein, once the bag reaches the maximum volume, receipt of further liquid from the inlet port causes pressure within the bag to increase up to a threshold pressure;

wherein the one-way outlet valve is configured to discharge the liquid from the outlet port when the threshold pressure is reached; and wherein the personal dispenser further comprises a plunger that is operable to exert a compressive force on the bag, to increase the pressure within the bag up to the threshold pressure and thereby discharge the liquid from the outlet port.

28. A liquid master dispenser, optionally including one or more features of any of 1 to 27, wherein the personal dispenser is configured so that the liquid is contained in the receptacle without coming into contact with atmospheric air;

wherein the plunger comprises a manually operable push button;

wherein the personal dispenser comprises a housing defining an internal cavity that extends longitudinally from a first end of the housing to a second end of the housing, the housing having a rack of teeth arranged longitudinally on an internal surface thereof;

wherein the plunger comprises a flexible pawl arranged within the internal cavity, the flexible pawl having a foot that, when in an unbiased state, engages with the teeth;

wherein the bag is arranged within the internal cavity, between the flexible pawl and the first end of the housing;

wherein the foot and the teeth are angled so that:

(i) the foot slides freely along the rack when the plunger is moved longitudinally toward the first end of the housing; and (ii) when the foot is in the unbiased state, the engagement of the foot with the teeth prevents the plunger from being moved longitudinally toward the second end of the housing;

the liquid dispenser further comprising a mounting dock for removably mounting the personal dispenser, the mounting dock being positioned so that the personal dispenser is coupled to the dispenser outlet when the personal dispenser is mounted to the mounting dock;

wherein the mounting dock comprises a protruding rib, and the housing of the personal dispenser has a slot that is sized to receive the protruding rib when the personal dispenser is mounted to the mounting dock;

wherein the protruding rib is configured to engage with the foot when received by the slot, so as to bend the foot away from, and out of engagement with, the rack;

wherein the foot slides freely along the rib when the plunger is moved longitudinally toward the first end of the housing and toward the second end of the housing; and wherein the foot is configured to return to the unbiased state upon removal of the rib from the slot.

29. A liquid master dispenser, optionally including one or more features of any of 1 to 28, wherein the liquid comprises a hand soap or a hand sanitizer.

30. A refillable personal dispenser for dispensing hand cleaning liquid, optionally including one or more features of any of 1 to 29, comprising:

a receptacle for containing the liquid;

a coupling mechanism for releasably coupling to a reservoir;

an inlet port for receiving the liquid from the reservoir and communicating the liquid to the receptacle; and an outlet port for discharge of the liquid from the receptacle;

wherein the outlet port is configured so that, while the personal dispenser is coupled to the reservoir, the liquid received by the inlet port accumulates in the receptacle until the receptacle contains a preselected volume of the liquid; and once the receptacle contains the preselected volume of the liquid, the outlet port is configured to discharge the liquid contained in the receptacle upon receipt of further said liquid by the inlet port;

wherein the inlet port comprises a one-way inlet valve that permits fluid to enter the receptacle through the inlet port, and prevents fluid from exiting the receptacle through the inlet port; and wherein the receptacle defines an internal volume and is compressible to selectively reduce the internal volume from an uncompressed volume to a compressed volume upon application of a compressing force, to thereby discharge the liquid from the outlet port.

31. A refillable personal dispenser, optionally including one or more features of any of 1 to 30, wherein the personal dispenser is configured so that the liquid is contained in the receptacle without coming into contact with atmospheric air.

32. A refillable personal dispenser, optionally including one or more features of any of 1 to 31, wherein the outlet port comprises a one-way outlet valve that permits fluid to exit the receptacle through the outlet port, and prevents fluid from entering the receptacle through the outlet port; and wherein the receptacle comprises a collapsible bag that is configured to expand, up to a maximum volume, to accommodate the liquid received by the inlet port;

wherein, once the bag reaches the maximum volume, receipt of further liquid from the inlet port causes pressure within the bag to increase up to a threshold pressure;

wherein the one-way outlet valve is configured to discharge the liquid from the outlet port when the threshold pressure is reached; and wherein the personal dispenser further comprises a plunger that is operable to exert a compressive force on the bag, to increase the pressure within the bag up to the threshold pressure and thereby discharge the liquid from the outlet port.

33. A refillable personal dispenser, optionally including one or more features of any of 1 to 32, wherein the plunger comprises a manually operable push button;

wherein the personal dispenser comprises a housing defining an internal cavity that extends longitudinally from a first end of the housing to a second end of the housing, the housing having a rack of teeth arranged longitudinally on an internal surface thereof;

wherein the plunger comprises a flexible pawl arranged within the internal cavity, the flexible pawl having a foot that, when in an unbiased state, engages with the teeth;

wherein the bag is arranged within the internal cavity, between the flexible pawl and the first end of the housing;

wherein the foot and the teeth are angled so that:

(i) the foot slides freely along the rack when the plunger is moved longitudinally toward the first end of the housing; and (ii) when the foot is in the unbiased state, the engagement of the foot with the teeth prevents the plunger from being moved longitudinally toward the second end of the housing;

wherein the housing has a slot that is sized to receive a protruding rib when the personal dispenser is coupled to the reservoir, so that the rib engages with the foot so as to bend the foot away from, and out of engagement with, the rack;

wherein the foot slides freely along the rib when the plunger is moved longitudinally toward the first end of the housing and toward the second end of the housing; and wherein the foot is configured to return to the unbiased state upon removal of the rib from the slot.

34. A liquid dispenser, optionally including one or more features of any of 1 to 33, comprising:

a reservoir for containing liquid to be dispensed;

a dispenser outlet for discharge of the liquid from the reservoir;

a discharge mechanism operable to discharge the liquid from the dispenser outlet when activated; and a removable personal dispenser, wherein the liquid dispenser is configured to deliver the liquid from the reservoir to the personal dispenser.

35. A liquid dispenser, optionally including one or more features of any of 1 to 34, further comprising a usage monitoring system configured to generate information indicative of an amount of the liquid dispensed from the liquid dispenser, wherein said amount includes the liquid dispensed from the dispenser outlet and the liquid delivered to the personal dispenser;

wherein the liquid comprises a hand cleaning liquid.

36. A liquid master dispenser, optionally including one or more features of any of 1 to 35, comprising:

a reservoir for containing liquid to be dispensed;

a dispenser outlet for discharge of the liquid from the reservoir;

a discharge mechanism operable to discharge the liquid from the dispenser outlet when activated; and a personal dispenser removably coupled to the dispenser outlet, the personal dispenser comprising a receptacle for containing the liquid and an outlet port for discharge of the liquid from the receptacle;

wherein:

(a) while the personal dispenser is coupled to the dispenser outlet, the liquid discharged from the dispenser outlet accumulates in the receptacle until the receptacle contains a preselected volume of the liquid, and once the receptacle contains the preselected volume of the liquid, the discharge of further said liquid from the dispenser outlet causes the liquid contained in the receptacle to be discharged from the outlet port; and (b) while the personal dispenser is removed from the dispenser outlet:

(i) the personal dispenser is configured to be carried manually to locations remote from the master dispenser for selectively discharging the liquid contained in the receptacle from the outlet port; and (ii) the discharge mechanism is operable to discharge the liquid contained in the reservoir from the dispenser outlet.

37. A liquid master dispenser, optionally including one or more features of any of 1 to 36, wherein the personal dispenser includes an inlet port for receiving the liquid discharged from the dispenser outlet and communicating the liquid to the receptacle; the personal dispenser coupled to the master dispenser with the dispenser outlet engaged with the inlet port.

38. A liquid master dispenser, optionally including one or more features of any of 1 to 37, wherein the inlet port comprises a one-way inlet valve that permits fluid to enter the receptacle through the inlet port, and prevents fluid from exiting the receptacle through the inlet port.

39. A liquid master dispenser, optionally including one or more features of any of 1 to 38, wherein the outlet port comprises a one-way outlet valve that permits fluid to exit the receptacle through the outlet port, and prevents fluid from entering the receptacle through the outlet port.

40. A liquid master dispenser, optionally including one or more features of any of 1 to 39, wherein the receptacle defines an internal volume and is compressible to selectively reduce the internal volume from an uncompressed volume to a compressed volume upon application of a compressing force, to thereby discharge the liquid from the outlet port.

41. A liquid master dispenser, optionally including one or more features of any of 1 to 42, wherein the receptacle is biased toward returning to the uncompressed volume upon release of the compressing force.

42. A liquid master dispenser, optionally including one or more features of any of 1 to 41, wherein the personal dispenser comprises a one-way air inlet valve configured to permit air to enter the receptacle as the receptacle returns to the uncompressed volume while the personal dispenser is removed from the dispenser outlet.

43. A liquid master dispenser, optionally including one or more features of any of 1 to 42, wherein the inlet valve is also the one-way air inlet valve.

44. A liquid master dispenser, optionally including one or more features of any of 1 to 43, wherein the discharge mechanism is configured to permit the liquid to be drawn from the reservoir out the dispenser outlet through application of a vacuum pressure to the dispenser outlet; and wherein the personal dispenser comprises a dispensing mechanism operable, while the personal dispenser is coupled to the dispenser outlet, to create the vacuum pressure to draw the liquid from the reservoir, out the dispenser outlet, and into the receptacle.

45. A liquid master dispenser, optionally including one or more features of any of 1 to 44, wherein the dispensing mechanism is manually operative to create the vacuum pressure.

46. A liquid master dispenser, optionally including one or more features of any of 1 to 45, wherein the discharge mechanism requires electrical power for operation, and while the personal dispenser is coupled to the dispenser outlet, if the electrical power required for operation of the discharge mechanism is not available, operation of the dispensing mechanism draws the liquid from the reservoir, out the dispenser outlet, into the receptacle, and when the receptacle contains the preselected volume of the liquid, out the outlet port.

47. A liquid master dispenser, optionally including one or more features of any of 1 to 46, wherein while the personal dispenser is coupled to the dispenser outlet, the dispenser outlet sealingly engages with the inlet port, placing the dispenser outlet in communication with the receptacle.

48. A liquid master dispenser, optionally including one or more features of any of 1 to 49, wherein while the personal dispenser is coupled to the dispenser outlet, a one-way valve outlet valve of the discharge mechanism permits fluid to exit the reservoir through an outlet opening, and prevents fluid from entering the reservoir from the receptacle via the dispenser outlet and the outlet port.

49. A liquid master dispenser, optionally including one or more features of any of 1 to 48, wherein while the personal dispenser is coupled to the dispenser outlet, the personal dispenser is configured to draw the liquid from the reservoir into the receptacle via the dispenser outlet, and when the receptacle contains the preselected volume of the liquid, to discharge the liquid contained in the receptacle from the outlet port.

50. A liquid master dispenser, optionally including one or more features of any of 1 to 49, wherein the receptacle comprises a diaphragm pump that is manually operable to discharge the liquid from the outlet port, the diaphragm pump comprising:

an internal chamber having an open end for receiving and expelling the liquid therefrom; and a manually compressible diaphragm defining one side of the internal chamber;

wherein the personal dispenser is configured so that compression of the diaphragm effects the discharge of the liquid from the outlet port;

wherein the internal chamber is configured so that, while the personal dispenser is coupled to the dispenser outlet, the open end is positioned at a designated height above the diaphragm, the designated height corresponding to a level of the liquid within the receptacle when the receptacle contains a designated volume of the liquid, so that the liquid only enters the internal chamber once the receptacle contains the designated volume of the liquid.

51. A liquid master dispenser, optionally including one or more features of any of 1 to 50, wherein the diaphragm is at least partially transparent and is visible to a user to provide a visual indication of whether the internal chamber contains the liquid.

52. A liquid master dispenser, optionally including one or more features of any of 1 to 51, wherein the receptacle further comprises a baffle interposed between the inlet port and the outlet port, for directing the liquid received by the inlet port toward the internal chamber.

53. A liquid master dispenser, optionally including one or more features of any of 1 to 52, wherein the diaphragm is configured so that a maximum volume of between 1 ml and 5 ml of the liquid is discharged from the outlet port with each manual compression of the diaphragm.

54. A liquid master dispenser, optionally including one or more features of any of 1 to 53, wherein the preselected volume is between 20 ml and 60 ml.

55. A liquid master dispenser, optionally including one or more features of any of 1 to 54, wherein the outlet port is configured to discharge the liquid contained in the receptacle only when a pressure differential across the outlet port exceeds a preselected threshold.

56. A liquid master dispenser, optionally including one or more features of any of 1 to 55, wherein the one-way outlet valve is configured to permit fluid to exit the receptacle through the outlet port only when a pressure differential across the one-way outlet valve exceeds a preselected threshold.

57. A liquid master dispenser, optionally including one or more features of any of 1 to 56, wherein the preselected threshold is at least 60 mbar.

58. A liquid master dispenser, optionally including one or more features of any of 1 to 57, wherein the outlet port comprises an opening in fluid communication with the receptacle; and wherein the personal dispenser is configured so that, while the personal dispenser is coupled to the dispenser outlet, the opening is positioned at a preselected height relative to the receptacle, the preselected height corresponding to a level of the liquid within the receptacle when the receptacle contains the preselected volume of the liquid.

59. A liquid master dispenser, optionally including one or more features of any of 1 to 58, wherein while the personal dispenser is coupled to the dispenser outlet, while the level of the liquid within the receptacle is below the preselected height, the liquid discharged into the receptacle from the dispenser outlet displaces air in the receptacle out the outlet port.

60. A liquid master dispenser, optionally including one or more features of any of 1 to 59, wherein the outlet port comprises a tubular member disposed within the receptacle;

wherein the opening is an inlet opening of the tubular member, and the tubular member extends from the inlet opening to a discharge opening; and wherein the personal dispenser is configured so that, while the personal dispenser is coupled to the dispenser outlet, the discharge opening is positioned below the preselected height.

61. A liquid master dispenser, optionally including one or more features of any of 1 to 60, wherein the discharge mechanism comprises a pump, and a hollow tubular elongated spout tube extending from an inlet end coupled to the pump, to an outlet end spaced therefrom; the outlet end of the spout tube comprising the dispenser outlet;

the liquid master dispenser further comprising a mounting dock that is removably coupled to the elongated spout tube between the inlet end and the outlet end, the mounting dock for removably mounting the personal dispenser;

wherein the personal dispenser further comprises a docking seat configured for engagement with the mounting dock, the inlet port spaced from the docking seat;

wherein with engagement of the mounting dock with the docking seat, the outlet end of the elongated spout tube engages with the personal dispenser within the inlet port.

62. A liquid master dispenser, optionally including one or more features of any of 1 to 61, wherein with the engagement of the mounting dock with the docking seat is a snap fit arrangement to provide a preselected resistance against removal of the docking seat from the mounting dock.

63. A liquid master dispenser, optionally including one or more features of any of 1 to 62, wherein the outlet end of the spout tube extends along an insertion axis, the outlet end of the elongated spout tube engages with the inlet port by relative movement parallel the insertion axis, and the mounting dock engages with the docking seat by relative movement parallel the insertion axis.

64. A liquid master dispenser, optionally including one or more features of any of 1 to 63, wherein the discharge mechanism comprises a pump, and the dispenser outlet comprises a hollow tubular elongated spout tube extending from an inlet end coupled to the pump, to an outlet end spaced therefrom;

wherein the elongated spout tube is configured so that the outlet end is angled below horizontal when the liquid dispenser is in an operative position for operation;

the liquid dispenser further comprising a mounting dock that is coupled to the elongated spout tube between the inlet end and the outlet end, the mounting dock defining a generally arcuate track for mounting the personal dispenser, the generally arcuate track having a front end that faces toward the outlet end of the elongated spout tube, and a back end that faces away from the outlet end of the elongated spout tube;

wherein the personal dispenser further comprises a generally arcuate docking seat configured for sliding engagement with the generally arcuate track, the generally arcuate docking seat having a front end that faces toward the inlet port of the personal dispenser, and a back end that faces away from the inlet port of the personal dispenser; and wherein the personal dispenser is configured so that the inlet port is spaced from the outlet end of the elongated spout tube while the back end of the generally arcuate docking seat is engaged with the front end of the generally arcuate track; and as the back end of the generally arcuate docking seat slides along the generally arcuate track toward the back end of the generally arcuate track, the inlet port moves toward the outlet end of the elongated spout tube; and once the generally arcuate docking seat is fully engaged with the generally arcuate track, with the front end of the generally arcuate docking seat engaged with the front end of the generally arcuate track, and the back end of the generally arcuate docking seat engaged with the back end of the generally arcuate track, the outlet end of the elongated spout tube is received within the inlet port.

65. A liquid master dispenser, optionally including one or more features of any of 1 to 64, wherein the generally arcuate track comprises an elongated dovetail shaped projection that extends from the front end of the generally arcuate track to the back end of the generally arcuate track; and wherein the generally arcuate docking seat comprises a pair of docking rails that extend from the front end of the generally arcuate docking seat to the back end of the generally arcuate docking seat, and define an elongated dovetail shaped channel therebetween for receiving the elongated dovetail shaped projection.

66. A liquid master dispenser, optionally including one or more features of any of 1 to 65, wherein:

a first of the generally arcuate track and the generally arcuate docking seat comprises an elongated dovetail shaped projection; and a second of the generally arcuate track and the generally arcuate docking seat comprises a pair of docking rails that define an elongated dovetail shaped channel therebetween for receiving the elongated dovetail shaped projection.

67. A liquid master dispenser, optionally including one or more features of any of 1 to 66, wherein the elongated dovetail shaped projection is tapered, such that a width of the elongated dovetail shaped projection at the front end of the generally arcuate track is less than a width of the elongated dovetail shaped projection at the back end of the generally arcuate track; and wherein the docking rails are configured to define a corresponding taper in the elongated dovetail shaped channel, such that a width of the elongated dovetail shaped channel at the front end of the generally arcuate docking seat is less than a width of the elongated dovetail shaped channel at the back end of the generally arcuate docking seat;

wherein the width of the elongated dovetail shaped projection at the back end of the generally arcuate track is greater than the width of the elongated dovetail shaped channel at the front end of the generally arcuate docking seat; and wherein the width of the elongated dovetail shaped channel at the back end of the generally arcuate docking seat is greater than the width of the elongated dovetail shaped projection at the front end of the generally arcuate track.

68. A liquid master dispenser, optionally including one or more features of any of 1 to 67, wherein the width of the elongated dovetail shaped projection at the front end of the generally arcuate track is approximately equal to the width of the elongated dovetail shaped channel at the front end of the generally arcuate docking seat; and wherein a width of the elongated dovetail shaped projection immediately adjacent to the front end of the generally arcuate track is greater than the width of the elongated dovetail shaped channel at the front end of the generally arcuate docking seat.

69. A liquid master dispenser, optionally including one or more features of any of 1 to 68, wherein each of the docking rails has a flexible retaining boss provided at the back end of the generally arcuate docking seat;

wherein the flexible retaining bosses are configured to sit behind the elongated dovetail shaped projection while the generally arcuate docking seat is fully engaged with the generally arcuate track, to provide a preselected resistance against sliding removal of the generally arcuate docking seat from the generally arcuate track.

70. A liquid master dispenser, optionally including one or more features of any of 1 to 69, wherein the elongated spout tube comprises a metallic tube that extends in a generally horizontal direction from the pump, and curves downwardly at the outlet end.

71. A liquid master dispenser, optionally including one or more features of any of 1 to 70, wherein the discharge mechanism comprises a pump assembly configured to discharge the liquid from the reservoir upon application of a mechanical force.

72. A liquid master dispenser, optionally including one or more features of any of 1 to 71, wherein the reservoir, the dispenser outlet, the pump assembly, and the personal dispenser together form a replaceable cartridge.

73. A liquid master dispenser, optionally including one or more features of any of 1 to 72, further comprising a housing configured to support the replaceable cartridge, the housing carrying an actuator configured to selectively apply the mechanical force to the pump assembly;

wherein the replaceable cartridge is removable from the housing.

74. A liquid master dispenser, optionally including one or more features of any of 1 to 73, wherein the dispenser outlet comprises an outlet tube configured to be received within the inlet port of the personal dispenser, the outlet tube extending along an insertion axis and having a coaxial annular groove on an external surface thereof;

wherein the inlet port comprises a coupling channel for receiving the outlet tube, the coupling channel extending along a coupling axis and having a coaxial O-ring disposed therein;

wherein the O-ring is configured to engage with the annular groove while the outlet tube is received within the coupling channel, to provide a preselected resistance against removal of the outlet tube from the coupling channel.

75. A liquid master dispenser, optionally including one or more features of any of 1 to 74, wherein the liquid comprises a hand soap or a hand sanitizer.

76. A liquid master dispenser, optionally including one or more features of any of 1 to 75, wherein the reservoir is configured to contain 500 ml to 2000 ml of the liquid, and the receptacle is configured to contain 20 ml to 60 ml of the liquid.

77. A liquid master dispenser, optionally including one or more features of any of 1 to 76, wherein the personal dispenser further comprises a pressure relief valve configured so that, while the personal dispenser is coupled to the dispenser outlet, the pressure relief valve releases air from the receptacle that is displaced by the liquid received from the dispenser outlet.

78. A liquid master dispenser, optionally including one or more features of any of 1 to 77, further comprising a usage monitoring system configured to generate information indicative of an amount of the liquid dispensed from the liquid dispenser.

79. A liquid master dispenser, optionally including one or more features of any of 1 to 78, further comprising a communication system configured to transmit the information to a usage tracking device.

80. A liquid master dispenser, optionally including one or more features of any of 1 to 79, further comprising:

a sensor configured to detect if the personal dispenser is coupled to the dispenser outlet; and a sensor configured to detect if the receptacle contains the preselected volume of the liquid.

81. A liquid master dispenser, optionally including one or more features of any of 1 to 80, further comprising a control system that receives information from the sensors and controls the discharge mechanism;

wherein the control system is configured to, upon detecting that the personal dispenser has been coupled to the dispenser outlet, activate the discharge mechanism to discharge the liquid to fill the receptacle when detecting that the receptacle does not contain the preselected volume of the liquid, and to end the activation of the discharge mechanism to fill the receptacle upon detecting that the receptacle contains the preselected volume of the liquid.

82. A liquid master dispenser, optionally including one or more features of any of 1 to 81, further comprising a manual activation mechanism for manual activation of the discharge mechanism.

83. A liquid master dispenser, optionally including one or more features of any of 1 to 82, further comprising an electronic activation device for activation of the discharge mechanism upon receiving an activation instruction from a user.

84. A liquid master dispenser, optionally including one or more features of any of 1 to 83, wherein the electronic activation device is selected from the group consisting of a button, a touchscreen, a wireless communication device, a microphone, a motion sensor, a radar sensor, a light sensor, an infrared sensor, and a camera.

85. A liquid master dispenser, optionally including one or more features of any of 1 to 84, wherein the electronic activation device senses the presence of a user's hand underneath the outlet port while the personal dispenser is coupled to the dispenser outlet, and underneath the dispenser outlet while the personal dispenser is removed from the dispenser outlet.

86. A liquid master dispenser, optionally including one or more features of any of 1 to 85, further comprising an electronic activation device for activation of the discharge mechanism upon sensing the presence of a user's hand underneath the outlet port while the personal dispenser is coupled to the dispenser outlet, and underneath the dispenser outlet while the personal dispenser is removed from the dispenser outlet.

87. A replaceable cartridge for a liquid master dispenser, optionally including one or more features of any of 1 to 86, comprising:

a reservoir for containing liquid to be dispensed, the reservoir having a reservoir outlet for selective discharge of the liquid from the reservoir; and a personal dispenser removably coupled to the reservoir outlet, the personal dispenser comprising:

a receptacle for containing the liquid discharged from the reservoir outlet;

an inlet port for receiving the liquid discharged from the reservoir outlet and communicating the liquid to the receptacle; and an outlet port for discharge of the liquid from the receptacle;

wherein the reservoir outlet is configured to permit the selective discharge of the liquid from the reservoir while the personal dispenser is removed from the reservoir outlet;

wherein the personal dispenser is configured so that, while the personal dispenser is coupled to the reservoir outlet, the liquid discharged from the reservoir outlet accumulates in the receptacle until the receptacle contains a preselected volume of the liquid, and once the receptacle contains the preselected volume of the liquid, the discharge of further said liquid from the reservoir outlet causes the liquid contained in the receptacle to be discharged from the outlet port; and wherein the personal dispenser is configured for selectively discharging the liquid contained in the receptacle from the outlet port, after the personal dispenser is removed from the reservoir outlet.

88. A replaceable cartridge, optionally including one or more features of any of 1 to 87, further comprising a pump assembly disposed across the reservoir outlet, the pump assembly configured to discharge the liquid from the reservoir upon application of a mechanical force.

89. A replaceable cartridge, optionally including one or more features of any of 1 to 88, wherein the pump assembly comprises an outlet tube configured to be received within the inlet port of the personal dispenser, the outlet tube extending along an insertion axis and having a coaxial annular groove on an external surface thereof;

wherein the inlet port comprises a coupling channel for receiving the outlet tube, the coupling channel extending along a coupling axis and having a coaxial O-ring disposed therein;

wherein the O-ring is configured to engage with the annular groove while the outlet tube is received within the coupling channel, to provide a preselected resistance against removal of the outlet tube from the coupling channel.

90. A replaceable cartridge, optionally including one or more features of any of 1 to 89, wherein the pump assembly comprises an outlet tube configured to be received within the inlet port of the personal dispenser, the outlet tube extending along an insertion axis;

wherein the inlet port comprises a coupling channel for receiving the outlet tube, the coupling channel extending along a coupling axis;

wherein the outlet tube and the inlet port are removably coupled in a snap with a preselected resistance against removal of the outlet tube from the inlet port.

91. A replaceable cartridge, optionally including one or more features of any of 1 to 90, wherein the liquid comprises a hand cleaner.

92. A replaceable cartridge, optionally including one or more features of any of 1 to 91, wherein the reservoir is configured to contain 250 ml to 5000 ml of the liquid; and wherein the preselected volume is between 10 ml and 80 ml.

93. A replaceable cartridge, optionally including one or more features of any of 1 to 92, wherein the reservoir is configured to contain 500 ml to 2000 ml of the liquid.

94. A replaceable cartridge, optionally including one or more features of any of 1 to 93, wherein the personal dispenser further comprises a pressure relief valve configured so that, while the personal dispenser is coupled to the reservoir outlet, the pressure relief valve releases air from the receptacle that is displaced by the liquid received from the reservoir outlet.

95. A replaceable cartridge, optionally including one or more features of any of 1 to 94, wherein the inlet port comprises a one-way inlet valve that permits fluid to enter the receptacle through the inlet port, and prevents fluid from exiting the receptacle through the inlet port; and wherein the receptacle defines an internal volume and is compressible to selectively reduce the internal volume from an uncompressed volume to a compressed volume upon application of a compressing force, to thereby discharge the liquid from the outlet port.

96. A replaceable cartridge, optionally including one or more features of any of 1 to 95, wherein the receptacle is biased toward returning to the uncompressed volume upon release of the compressing force;

wherein the outlet port comprises a one-way outlet valve that permits fluid to exit the receptacle through the outlet port, and prevents fluid from entering the receptacle through the outlet port; and wherein the personal dispenser comprises a one-way air inlet valve configured to permit air to enter the receptacle as the receptacle returns to the uncompressed volume, while the personal dispenser is removed from the reservoir outlet.

97. A replaceable cartridge, optionally including one or more features of any of 1 to 96, wherein the inlet valve is also the one-way air inlet valve.

98. A replaceable cartridge, optionally including one or more features of any of 1 to 97, wherein the outlet port is configured to discharge the liquid contained in the receptacle only when a pressure differential across the outlet port exceeds a preselected threshold.

99. A refillable personal dispenser for dispensing liquid, optionally including one or more features of any of 1 to 98, comprising:
a receptacle for containing the liquid;
a coupling mechanism for releasably coupling to a reservoir;
an inlet port for receiving the liquid from the reservoir and communicating the liquid to the receptacle; and
an outlet port for discharge of the liquid from the receptacle;
wherein the outlet port is configured so that, while the personal dispenser is coupled to the reservoir, the liquid received by the inlet port accumulates in the receptacle until the receptacle contains a preselected volume of the liquid; and once the receptacle contains the preselected volume of the liquid, the outlet port is configured to discharge the liquid contained in the receptacle upon receipt of further said liquid by the inlet port;
wherein the inlet port comprises a one-way inlet valve that permits fluid to enter the receptacle through the inlet port, and prevents fluid from exiting the receptacle through the inlet port; and
wherein the receptacle defines an internal volume and is compressible to selectively reduce the internal volume from an uncompressed volume to a compressed volume upon application of a compressing force, to thereby discharge the liquid from the outlet port.

100. A refillable personal dispenser, optionally including one or more features of any of 1 to 99, wherein the receptacle is biased toward returning to the uncompressed volume upon release of the compressing force;
wherein the outlet port comprises a one-way outlet valve that permits fluid to exit the receptacle through the outlet port, and prevents fluid from entering the receptacle through the outlet port; and
wherein the personal dispenser comprises a one-way air inlet valve configured to permit air to enter the receptacle as the receptacle returns to the uncompressed volume, while the personal dispenser is removed from the reservoir.

101. A refillable personal dispenser, optionally including one or more features of any of 1 to 100, wherein the inlet valve is also the one-way air inlet valve.

102. A refillable personal dispenser, optionally including one or more features of any of 1 to 101, wherein the receptacle comprises a diaphragm pump that is manually operable to discharge the liquid from the outlet port, the diaphragm pump comprising:
an internal chamber having an open end for receiving and expelling the liquid therefrom; and
a manually compressible diaphragm defining one side of the internal chamber;
wherein compression of the diaphragm effects the discharge of the liquid from the outlet port;
wherein the internal chamber is configured so that, while the personal dispenser is coupled to the reservoir, the open end is positioned at a designated height above the diaphragm, the designated height corresponding to a level of the liquid within the receptacle when the receptacle contains a designated volume of the liquid, so that the liquid only enters the internal chamber once the receptacle contains the designated volume of the liquid; and
wherein the diaphragm is at least partially transparent.

103. A refillable personal dispenser, optionally including one or more features of any of 1 to 102, wherein the receptacle further comprises a baffle interposed between the inlet port and the outlet port, for directing the liquid received by the inlet port toward the internal chamber.

104. A refillable personal dispenser, optionally including one or more features of any of 1 to 103, wherein the diaphragm is configured so that a maximum volume of between 1 ml and 5 ml of the liquid is discharged from the outlet port with each manual compression of the diaphragm.

105. A refillable personal dispenser, optionally including one or more features of any of 1 to 104, wherein the preselected volume is between 20 ml and 25 ml.

106. A refillable personal dispenser, optionally including one or more features of any of 1 to 105, wherein the outlet port is configured to discharge the liquid contained in the receptacle only when a pressure differential across the outlet port exceeds a preselected threshold.

107. A refillable personal dispenser, optionally including one or more features of any of 1 to 106, wherein the preselected threshold is at least 60 mbar.

108. A refillable personal dispenser, optionally including one or more features of any of 1 to 107, wherein the coupling mechanism comprises a generally arcuate docking seat configured for sliding engagement with a generally arcuate track of the reservoir, the generally arcuate docking seat having a front end that faces toward the inlet port, and a back end that faces away from the inlet port.

109. A refillable personal dispenser, optionally including one or more features of any of 1 to 108, wherein the generally arcuate docking seat comprises a pair of docking rails that extend from the front end of the generally arcuate docking seat to the back end of the generally arcuate docking seat, and define an elongated dovetail shaped channel therebetween.

110. A refillable personal dispenser, optionally including one or more features of any of 1 to 109, wherein the docking rails are configured to define a taper in the elongated dovetail shaped channel, such that a width of the elongated dovetail shaped channel at the front end of the generally arcuate docking seat is less than a width of the elongated dovetail shaped channel at the back end of the generally arcuate docking seat.

111. A refillable personal dispenser, optionally including one or more features of any of 1 to 110, wherein each of the docking rails has a flexible retaining boss provided at the back end of the generally arcuate docking seat;
wherein the flexible retaining bosses provide a preselected resistance against sliding removal of the generally arcuate docking seat from the generally arcuate track.

112. A refillable personal dispenser, optionally including one or more features of any of 1 to 111, wherein the liquid comprises a hand soap or a hand sanitizer.

113. A refillable personal dispenser, optionally including one or more features of any of 1 to 112, further comprising a pressure relief valve configured so that, while the personal dispenser is coupled to the reservoir, the pressure relief valve releases air from the receptacle that is displaced by the liquid received by the inlet port.

114. A liquid dispenser, optionally including one or more features of any of 1 to 113, comprising:
a reservoir for containing liquid to be dispensed;
a dispenser outlet for discharge of the liquid from the reservoir;
a discharge mechanism operable to discharge the liquid from the dispenser outlet when activated;
a refill outlet configured to couple with a personal dispenser and deliver the liquid from the reservoir to the personal dispenser; and
a filling mechanism operable to deliver the liquid from the refill outlet when activated.

115. A liquid dispenser, optionally including one or more features of any of 1 to 114, further comprising a usage monitoring system configured to generate information indicative of an amount of the liquid dispensed from the liquid dispenser, wherein said amount includes both the liquid dispensed from the dispenser outlet and the liquid delivered to the personal dispenser from the refill outlet.

116. A liquid dispenser, optionally including one or more features of any of 1 to 115, wherein the usage monitoring system comprises at least one of:

a sensor configured to detect a volume or a mass of the liquid contained in the reservoir;

a sensor configured to detect a flow of the liquid through the dispenser outlet;

a sensor configured to detect a flow of the liquid through the refill outlet;

a sensor configured to detect the activation of the discharge mechanism; and a sensor configured to detect the activation of the filling mechanism.

117. A liquid dispenser, optionally including one or more features of any of 1 to 116, further comprising a communication system configured to transmit the information to a usage tracking device.

118. A liquid dispenser, optionally including one or more features of any of 1 to 117, further comprising a three-way valve for directing the liquid from the reservoir to the dispenser outlet or the refill outlet, wherein the three-way valve is configured to:

permit the liquid to flow from the reservoir to the refill outlet, and prevent the liquid from flowing from the reservoir to the dispenser outlet, when the personal dispenser is coupled to the refill outlet and contains less than a preselected volume of the liquid;

permit the liquid to flow from the reservoir to the dispenser outlet, and prevent the liquid from flowing from the reservoir to the refill outlet, when the personal dispenser is coupled to the refill outlet and contains the preselected volume of the liquid; and permit the liquid to flow from the reservoir to the dispenser outlet, and prevent the liquid from flowing from the reservoir to the refill outlet, when the personal dispenser is uncoupled from the refill outlet.

119. A liquid dispenser, optionally including one or more features of any of 1 to 118, further comprising a conduit for conveying the liquid from the reservoir to the dispenser outlet or the refill outlet, the conduit having a conduit inlet in fluid communication with the reservoir and a conduit outlet;

wherein the dispenser outlet and the refill outlet are rotatably mounted relative to the conduit outlet for selectively alternating between a dispensing condition, wherein the dispenser outlet is aligned with and in fluid communication with the conduit outlet, and a refill condition, wherein the refill outlet is aligned with and in fluid communication with the conduit outlet.

120. A liquid dispenser, optionally including one or more features of any of 1 to 119, further comprising:

a sensor configured to detect if the personal dispenser is coupled to the refill outlet; and a sensor configured to detect if the personal dispenser is full.

121. A liquid dispenser, optionally including one or more features of any of 1 to 120, wherein the filling mechanism is configured to automatically deliver the liquid from the refill outlet to the personal dispenser, when the personal dispenser is coupled to the refill outlet; and wherein the filling mechanism is configured to automatically stop delivery of the liquid from the refill outlet to the personal dispenser, when the personal dispenser is full.

122. A liquid dispenser, optionally including one or more features of any of 1 to 121, further comprising at least one further refill outlet configured to couple with at least one further personal dispenser and deliver the liquid from the reservoir to the at least one further personal dispenser.

123. A liquid dispenser, optionally including one or more features of any of 1 to 122, wherein the liquid comprises a hand soap or a hand sanitizer.

124. A hand cleaning liquid master dispenser, optionally including one or more features of any of 1 to 123, comprising:

a reservoir for containing liquid to be dispensed;

a discharge mechanism operable to discharge the liquid from the reservoir when activated; and a personal dispenser removably coupled to the master dispenser, the personal dispenser comprising a receptacle for containing the liquid and an outlet port for discharge of the liquid from the receptacle;

wherein:

(a) while the personal dispenser is coupled to the master dispenser, the discharge mechanism discharges the liquid from the reservoir into the receptacle and the liquid discharged accumulates in the receptacle until the receptacle contains a preselected volume of the liquid, and while the receptacle contains the preselected volume of the liquid, the discharge mechanism discharges the liquid from a dispenser outlet; and (b) while the personal dispenser is removed from the master dispenser:

(i) the personal dispenser is configured to be carried manually to locations remote from the master dispenser for selectively discharging the liquid contained in the receptacle from the outlet port; and (ii) the discharge mechanism is operable to discharge the liquid contained in the reservoir from the dispenser outlet.

125. A hand cleaning liquid master dispenser, optionally including one or more features of any of 1 to 124, wherein:

while the personal dispenser is coupled to the master dispenser, the outlet port is the dispenser outlet.

126. A hand cleaning liquid master dispenser, optionally including one or more features of any of 1 to 125, wherein:

the dispenser outlet is separate from the outlet port;

a valve arrangement is provided to selectively deliver the liquid from the discharge mechanism: (a) to the receptacle while the personal dispenser is coupled to the master dispenser and the receptacle contains a volume of liquid less than the preselected volume of the liquid; and (b) to the dispenser outlet while the personal dispenser is coupled to the master dispenser and the receptacle contains at least the preselected volume of the liquid; and (c) to the dispenser outlet while the personal dispenser is removed from the master dispenser.

127. A hand cleaning liquid master dispenser, optionally including one or more features of any of 1 to 128, further comprising a usage monitoring system configured to generate information indicative of an amount of the liquid dispensed from the reservoir by the discharge mechanism.

128. A liquid master dispenser, optionally including one or more features of any of 1 to 127, wherein the reservoir has a cavity sized for removably receiving the personal dispenser.

129. A liquid master dispenser, optionally including one or more features of any of 1 to 128, wherein, prior to assembly of the liquid master dispenser, the personal dispenser is held within the cavity of the reservoir in an initial bundled configuration.

130. A liquid master dispenser, optionally including one or more features of any of 1 to 129, further comprising a label that is secured to a face of the reservoir and a face of the personal dispenser while in the initial bundled configuration;

wherein the label is configured to be severed upon removal of the personal dispenser from the cavity, so as to leave a first portion of the label secured to the face of the reservoir and a second portion of the label secured to the face of the personal dispenser.

131. A liquid master dispenser, optionally including one or more features of any of 1 to 130, further comprising a mounting dock for removably mounting the personal dispenser, the mounting dock having resiliently flexible arms;

wherein the resiliently flexible arms, while in an unbiased condition, define an inner profile that is complementary to an outer profile of the personal dispenser;

wherein the personal dispenser is mounted to the mounting dock by urging the flexible arms apart, positioning the personal dispenser between the flexible arms, and allowing the flexible arms to return to the unbiased condition with the personal dispenser therebetween; and wherein the mounting dock is positioned so that the personal dispenser is coupled to the dispenser outlet when the personal dispenser is mounted to the mounting dock.

132. A liquid master dispenser, optionally including one or more features of any of 1 to 131, wherein the mounting dock and the personal dispenser have lock-out features that prevent the mounting dock and the personal dispenser from mounting with a device that lacks complimentary lock-out features.

133. A liquid master dispenser, optionally including one or more features of any of 1 to 132, wherein the lock-out features comprise at least one rib on the mounting dock or the personal dispenser, and at least one void on the mounting dock or the personal dispenser, wherein the void is configured to receive the rib when the personal dispenser is mounted to the mounting dock.

134. A liquid master dispenser, optionally including one or more features of any of 1 to 133, wherein the personal dispenser is configured so that the liquid is contained in the receptacle without coming into contact with atmospheric air.

135. A liquid master dispenser, optionally including one or more features of any of 1 to 134, wherein the inlet port comprises a one-way inlet valve that permits fluid to enter the receptacle through the inlet port, and prevents fluid from exiting the receptacle through the inlet port;

wherein the outlet port comprises a one-way outlet valve that permits fluid to exit the receptacle through the outlet port, and prevents fluid from entering the receptacle through the outlet port; and wherein the receptacle comprises a collapsible bag.

136. A liquid master dispenser, optionally including one or more features of any of 1 to 135, wherein the collapsible bag is configured to expand, up to a maximum volume, to accommodate the liquid received by the inlet port.

137. A liquid master dispenser, optionally including one or more features of any of 1 to 136, wherein, once the bag reaches the maximum volume, receipt of further liquid from the inlet port causes pressure within the bag to increase up to a threshold pressure; and wherein the one-way outlet valve is configured to discharge the liquid from the outlet port when the threshold pressure is reached.

138. A liquid master dispenser, optionally including one or more features of any of 1 to 137, wherein the personal dispenser further comprises a plunger that is operable to exert a compressive force on the bag, to increase the pressure within the bag up to the threshold pressure and thereby discharge the liquid from the outlet port.

139. A liquid master dispenser, optionally including one or more features of any of 1 to 138, wherein the plunger comprises a manually operable push button.

140. A liquid master dispenser, optionally including one or more features of any of 1 to 139, wherein the personal dispenser comprises a housing defining an internal cavity that extends longitudinally from a first end of the housing to a second end of the housing, the housing having a rack of teeth arranged longitudinally on an internal surface thereof;

wherein the plunger comprises a flexible pawl arranged within the internal cavity, the flexible pawl having a foot that, when in an unbiased state, engages with the teeth;

wherein the bag is arranged within the internal cavity, between the flexible pawl and the first end of the housing; and wherein the foot and the teeth are angled so that:

(i) the foot slides freely along the rack when the plunger is moved longitudinally toward the first end of the housing; and (ii) when the foot is in the unbiased state, the engagement of the foot with the teeth prevents the plunger from being moved longitudinally toward the second end of the housing.

141. A liquid master dispenser, optionally including one or more features of any of 1 to 140, further comprising a mounting dock for removably mounting the personal dispenser, the mounting dock being positioned so that the personal dispenser is coupled to the dispenser outlet when the personal dispenser is mounted to the mounting dock;

wherein the mounting dock comprises a protruding rib, and the housing of the personal dispenser has a slot that is sized to receive the protruding rib when the personal dispenser is mounted to the mounting dock;

wherein the protruding rib is configured to engage with the foot when received by the slot, so as to bend the foot away from, and out of engagement with, the rack;

wherein the foot slides freely along the rib when the plunger is moved longitudinally toward the first end of the housing and toward the second end of the housing; and wherein the foot is configured to return to the unbiased state upon removal of the rib from the slot.

142. A liquid master dispenser, optionally including one or more features of any of 1 to 141, wherein the reservoir is configured so that the liquid is contained in the reservoir without coming into contact with the atmospheric air.

143. A liquid master dispenser, optionally including one or more features of any of 1 to 142, wherein the reservoir is configured to collapse as the liquid is discharged therefrom.

144. A liquid master dispenser, optionally including one or more features of any of 1 to 143, wherein the dispenser outlet is configured to sealingly engage with the inlet port of the personal dispenser, to prevent the atmospheric air from contacting the liquid as it is transferred from the dispenser outlet to the personal dispenser.

145. A device incorporating one or more features of any of 1 to 144.

146. A replaceable cartridge for a liquid master dispenser, optionally including one or more features of any of 1 to 145, comprising:

a reservoir for containing liquid to be dispensed from the liquid master dispenser; and a personal dispenser removably coupled to the reservoir, the personal dispenser comprising:

a receptacle for containing liquid to be dispensed from the personal dispenser; and an outlet port for discharge of the liquid from the receptacle;

wherein the personal dispenser is configured for selectively discharging the liquid contained in the receptacle from the outlet port, after the personal dispenser is removed from the reservoir.

147. A replaceable cartridge, optionally including one or more features of any of 1 to 146, wherein the reservoir has a cavity sized for removably receiving the personal dispenser.

148. A replaceable cartridge, optionally including one or more features of any of 1 to 147, wherein the personal dispenser is held within the cavity of the reservoir in an initial bundled configuration.

149. A replaceable cartridge, optionally including one or more features of any of 1 to 148, further comprising a label that is secured to a face of the reservoir and a face of the personal dispenser while in the initial bundled configuration;

wherein the label is configured to be severed upon removal of the personal dispenser from the cavity, so as to leave a first portion of the label secured to the face of the reservoir and a second portion of the label secured to the face of the personal dispenser.

150. A replaceable cartridge, optionally including one or more features of any of 1 to 149, wherein the personal dispenser is held within the cavity of the reservoir, without protruding from the cavity, when in an initial bundled configuration.

151. A replaceable cartridge, optionally including one or more features of any of 1 to 150, wherein the reservoir has a face in which the cavity is formed, and the personal dispenser has a face that is substantially flush with the face of the reservoir when in the initial bundled configuration.

152. A replaceable cartridge, optionally including one or more features of any of 1 to 151, wherein the replaceable cartridge has a substantially flat profile when in the initial bundled configuration.

153. A replaceable cartridge, optionally including one or more features of any of 1 to 152, wherein the reservoir has at least one indentation adjacent to the cavity.

154. A replaceable cartridge, optionally including one or more features of any of 1 to 153, wherein the at least one indentation is configured to provide manual access for removal of the personal dispenser from the cavity.

155. A replaceable cartridge, optionally including one or more features of any of 1 to 155, wherein the at least one indentation comprises two indentations that are provided on opposite sides of the cavity, the two indentations being sized and spaced to allow a user to grasp and remove the personal dispenser from the cavity.

156. A replaceable cartridge, optionally including one or more features of any of 1 to 155, wherein the reservoir comprises:

a top wall with an outlet opening;

a bottom wall; and a side wall that connects the top wall and the bottom wall;

wherein the cavity is formed as a recess in the side wall.

157. A replaceable cartridge, optionally including one or more features of any of 1 to 156, wherein the reservoir is formed from plastic.

158. A replaceable cartridge, optionally including one or more features of any of 1 to 157, wherein the reservoir has a reservoir outlet for selective discharge of the liquid from the reservoir;

wherein the personal dispenser has an inlet port for receiving the liquid discharged from the reservoir outlet and communicating the liquid to the receptacle;

wherein the personal dispenser is configured to sealingly engage with the reservoir outlet so that the liquid discharged from the reservoir outlet accumulates in the receptacle, the personal dispenser being selectively removable from the reservoir outlet;

wherein the inlet port comprises a one-way inlet valve that permits fluid to enter the receptacle through the inlet port, and prevents fluid from exiting the receptacle through the inlet port; and wherein the receptacle defines an internal volume and is compressible to selectively reduce the internal volume from an uncompressed volume to a compressed volume upon application of a compressing force, to thereby discharge the liquid from the outlet port.

159. A replaceable cartridge, optionally including one or more features of any of 1 to 158, wherein the liquid to be dispensed from the master liquid dispenser and the liquid to be dispensed from the personal dispenser comprises a hand cleaner.

160. A liquid dispenser, optionally including one or more features of any of 1 to 159, comprising:

a reservoir for containing liquid to be dispensed;

a dispenser outlet for discharge of the liquid from the reservoir;

a discharge mechanism operable to discharge the liquid from the dispenser outlet when activated;

a refill outlet configured to couple with a personal dispenser and deliver the liquid from the reservoir to the personal dispenser; and a filling mechanism operable to deliver the liquid from the refill outlet when activated;

wherein the dispenser outlet is separate from the refill outlet.

161. A liquid dispenser, optionally including one or more features of any of 1 to 160, further comprising a valve arrangement for directing the liquid from the reservoir to the dispenser outlet or the refill outlet, wherein the valve arrangement is configured to:

permit the liquid to flow from the reservoir to the refill outlet, and prevent the liquid from flowing from the reservoir to the dispenser outlet, when the personal dispenser is coupled to the refill outlet and contains less than a preselected volume of the liquid;

permit the liquid to flow from the reservoir to the dispenser outlet, and prevent the liquid from flowing from the reservoir to the refill outlet, when the personal dispenser is coupled to the refill outlet and contains the preselected volume of the liquid; and permit the liquid to flow from the reservoir to the dispenser outlet, and prevent the liquid from flowing from the reservoir to the refill outlet, when the personal dispenser is uncoupled from the refill outlet.

162. A liquid dispenser, optionally including one or more features of any of 1 to 161, further comprising a conduit for conveying the liquid from the reservoir to the dispenser outlet or the refill outlet, the conduit having a conduit inlet in fluid communication with the reservoir and a conduit outlet;

wherein the dispenser outlet and the refill outlet are rotatably mounted relative to the conduit outlet for selectively alternating between a dispensing condition, wherein the dispenser outlet is aligned with and in fluid communication with the conduit outlet, and a refill condition, wherein the refill outlet is aligned with and in fluid communication with the conduit outlet.

163. A liquid dispenser, optionally including one or more features of any of 1 to 162, further comprising a usage monitoring system configured to generate information indicative of an amount of the liquid dispensed from the liquid dispenser, wherein said amount includes both the liquid dispensed from the dispenser outlet and the liquid delivered to the personal dispenser from the refill outlet;

wherein the usage monitoring system comprises at least one of:

a sensor configured to detect a volume or a mass of the liquid contained in the reservoir;

a sensor configured to detect a flow of the liquid through the dispenser outlet;

a sensor configured to detect a flow of the liquid through the refill outlet;

a sensor configured to detect the activation of the discharge mechanism; and a sensor configured to detect the activation of the filling mechanism.

164. A liquid dispenser, optionally including one or more features of any of 1 to 163, further comprising:

a sensor configured to detect if the personal dispenser is coupled to the refill outlet; and a sensor configured to detect if the personal dispenser is full;

wherein the filling mechanism is configured to automatically deliver the liquid from the refill outlet to the personal dispenser, when the personal dispenser is coupled to the refill outlet; and wherein the filling mechanism is configured to automatically stop delivery of the liquid from the refill outlet to the personal dispenser, when the personal dispenser is full.

165. A liquid dispenser, optionally including one or more features of any of 1 to 164, wherein the liquid comprises a hand cleaner.

BRIEF DESCRIPTION OF THE DRAWINGS

Further aspects and advantages of the invention will appear from the following description taken together with the accompanying drawings, in which.

DETAILED DESCRIPTION OF THE DRAWINGS

Figure 1:
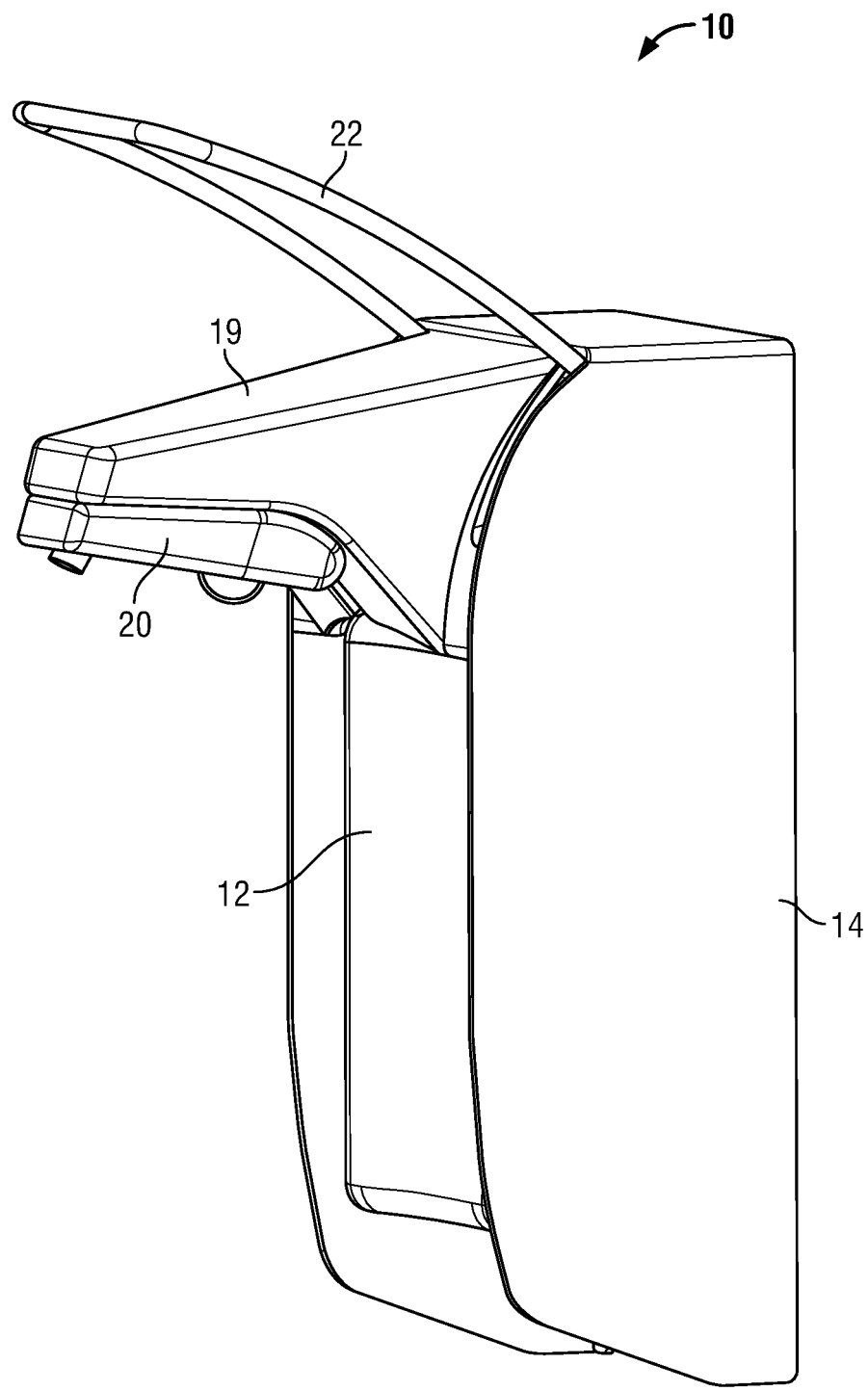
FIG. 1 shows a perspective view of a liquid master dispenser in accordance with a first preferred embodiment of the invention.

Reference is made first to FIGS. 1, 2A, 2B and 2C which show a liquid master dispenser 10 in accordance with a first preferred embodiment of the invention. The master dispenser 10 includes a reservoir 12, a housing 14, a pump assembly 16, a dispenser outlet 18, and a personal dispenser or point of care dispenser 20. The master dispenser 10 is similar to that disclosed in U.S. Pat. No. 7,748,573 to Ophardt et al., issued Jul. 6, 2010, and in U.S. Publication No. US 2014/025336 to Ophardt, both of which are incorporated herein by reference.

The reservoir 12 is a container for holding the liquid to be dispensed from the master dispenser 10. The housing 14 partially surrounds and supports the reservoir 12, the pump assembly 16, and the dispenser outlet 18. The housing 14 is adapted for permanent attachment to a wall or other similar structure, although the housing 14 could alternatively be free standing as on a table top or other support surface, or selectively removable from a stand or other support. The housing 14 carries a discharge tube shroud 19.

The pump assembly 16 is configured to pump the liquid from the reservoir 12 and out through the dispenser outlet 18 upon application of a mechanical force thereto. In the preferred embodiment shown, a manual actuator 22 is provided for applying the mechanical force to the pump assembly 16.

Figure 2A:
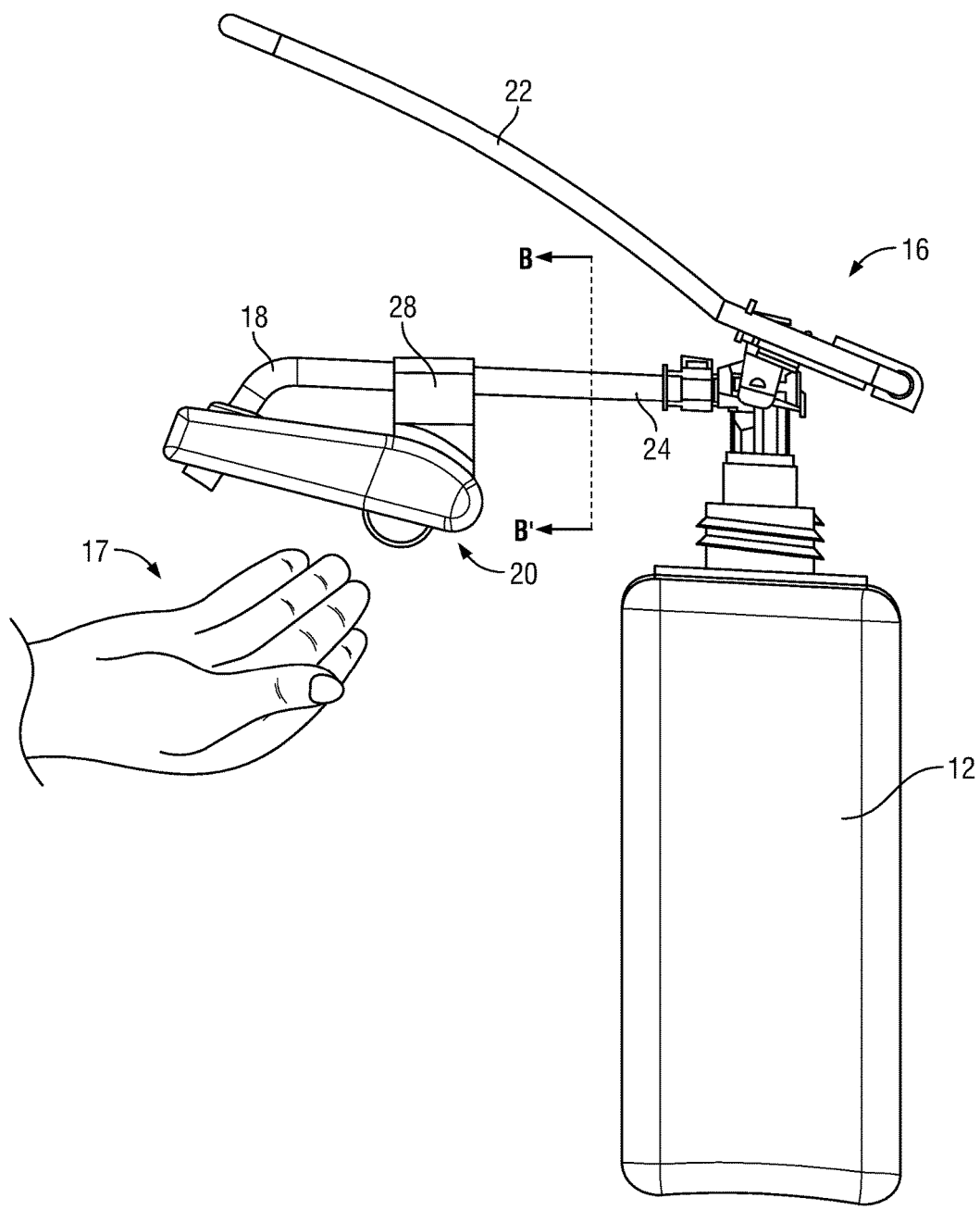
FIG. 2A shows a pictorial side view of the liquid master dispenser of FIG. 1 with the housing removed, and a personal dispenser in a coupled state.
Figure 2B:
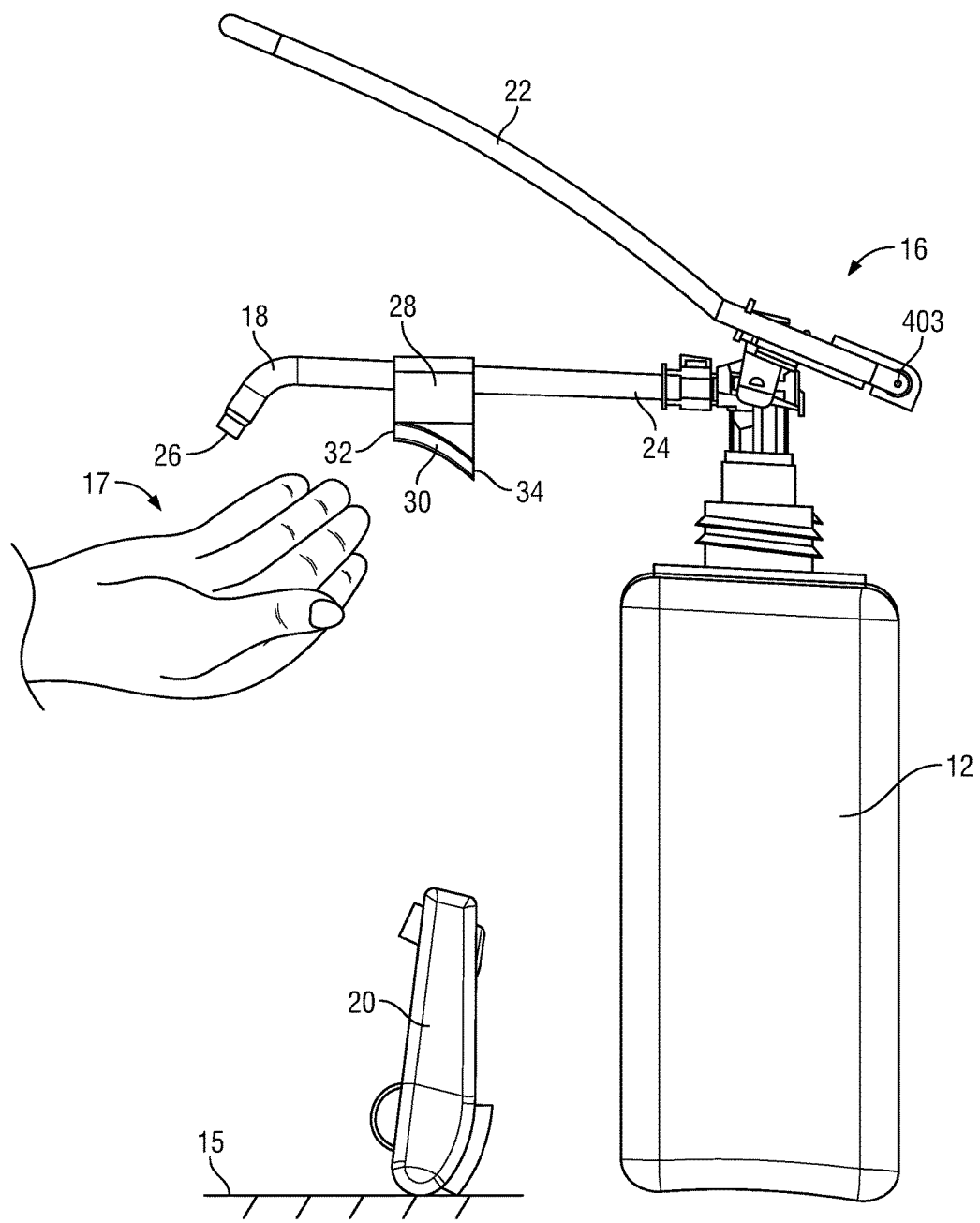
FIG. 2B show a pictorial side view of the liquid master dispenser as in FIG. 2A but with the personal dispenser in an uncoupled state supported on an independent desktop support surface.
Figure 2C:
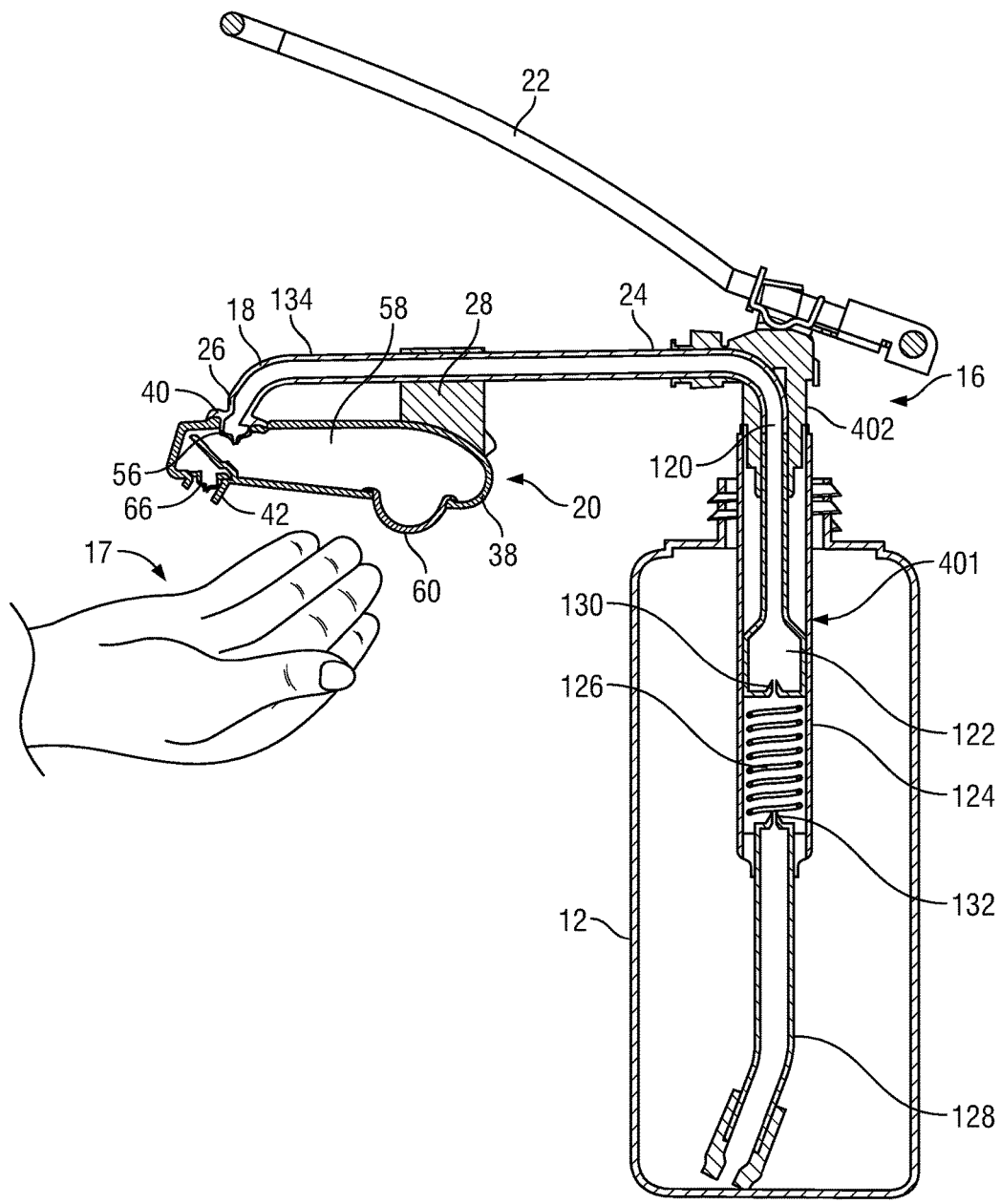
FIG. 2C shows a cross-sectional view FIG. 2A showing the liquid master dispenser and the personal dispenser in the coupled state.

The pump assembly 16 is best shown in FIG. 2C as including a piston chamber forming body 401 and a piston forming element 402. The piston chamber forming body 401 is fixed to the housing 14 against movement and defines therein a piston chamber 124 from which a dip tube 128 extends downwardly in to the reservoir 12. The reservoir 12 is supported by the housing 14. The piston forming element 402 is mounted to the piston chamber forming body 401 for relative vertical movement with a piston 122 of the piston forming element 402 coaxially slidable within piston chamber 124 biased upwardly by a spring 126 disposed within the piston chamber 124 between the piston chamber 124 and the piston 122. A manual actuator 22 in the form of a pivoting lever is mounted to the housing 14 for pivoting about a horizontal axis to move the piston forming element 402 downwardly relative to the piston chamber forming body 401 against the bias of the spring 126.

The piston forming element 402 includes a hollow spout tube 134 that extends from the piston 122 forming an internal conduit 120 therein that is integral with a dispenser outlet 18. At one end, the internal conduit 120 expands radially outward to form the piston 122, which sits snugly within the piston chamber 124. The piston 122 is provided with a duckbill check valve 130, which permits fluid to flow into the piston 122 from the piston chamber 124, and prevents fluid from flowing out of the piston 122 into the piston chamber 124.

The piston chamber 124 defines a cylindrical cavity within which the piston 122 is able to move up and down. The spring 126 sits within the piston chamber 124 below the piston 122, and biases the piston 122 upwards. The dip tube 128 extends downwardly from the piston chamber 124 toward the bottom of the reservoir 12, for drawing the liquid therefrom. A one-way duckbill valve 132 sits between the piston chamber 124 and the dip tube 128, and permits fluid to flow into the piston chamber 124 from the dip tube 128, and prevents fluid from flowing out of the piston chamber 124 into the dip tube 128.

The pump assembly 16 is operated by depressing the manual actuator 22, which causes the internal conduit 120 and the piston 122 to slide downwardly within the piston chamber 124. The movement of the piston 122 pressurizes the fluid contained within the piston chamber 124, forcing the fluid upwards through the check valve 130. The influx of fluid into the piston 122 displaces any fluid contained therein, which in turn displaces any fluid contained within the internal conduit 120 and forces the fluid out through the dispenser outlet 18.

When the manual actuator 22 is released, the spring 126 pushes the piston 122 back up to its initial position. This reduces the pressure within the piston chamber 124, which draws liquid in from the reservoir 12 via the dip tube 128 and through the valve 132. The process may then be repeated as desired.

Initially, the pump assembly 16 is primed by operating the pump assembly 16 repeatedly until all of the air contained therein is completely displaced by liquid from the reservoir 12. Once the pump assembly 16 is fully primed, further operation of the pump assembly 16 will force the liquid contained therein out through the dispenser outlet 18.

As shown in FIG. 2C, the dispenser outlet 18 is an outer portion of the hollow tubular elongated spout tube 134 that extends horizontally from the internal conduit 120, and is in fluid communication with the reservoir 12 via the pump assembly 16 for receiving the liquid therefrom. The spout tube 134 extends from an inlet end 24 that is continuous with the internal conduit 120, to an outlet end 26 from which the liquid is dispensed. The spout tube 134 curves downward near the outlet end 26, so that the outlet end 26 is angled below horizontal, that is extends forwardly as it extends downwardly, to direct the liquid into a user's hand 17 disposed below the outlet end 26 during dispensing.

A mounting dock 28 is coupled to the spout tube 134 between the inlet end 24 and the outlet end 26. The mounting dock 28 is provided for sliding engagement with the personal dispenser 20, to enable coupling and uncoupling of the personal dispenser 20 with the spout tube 134.

Figure 3:
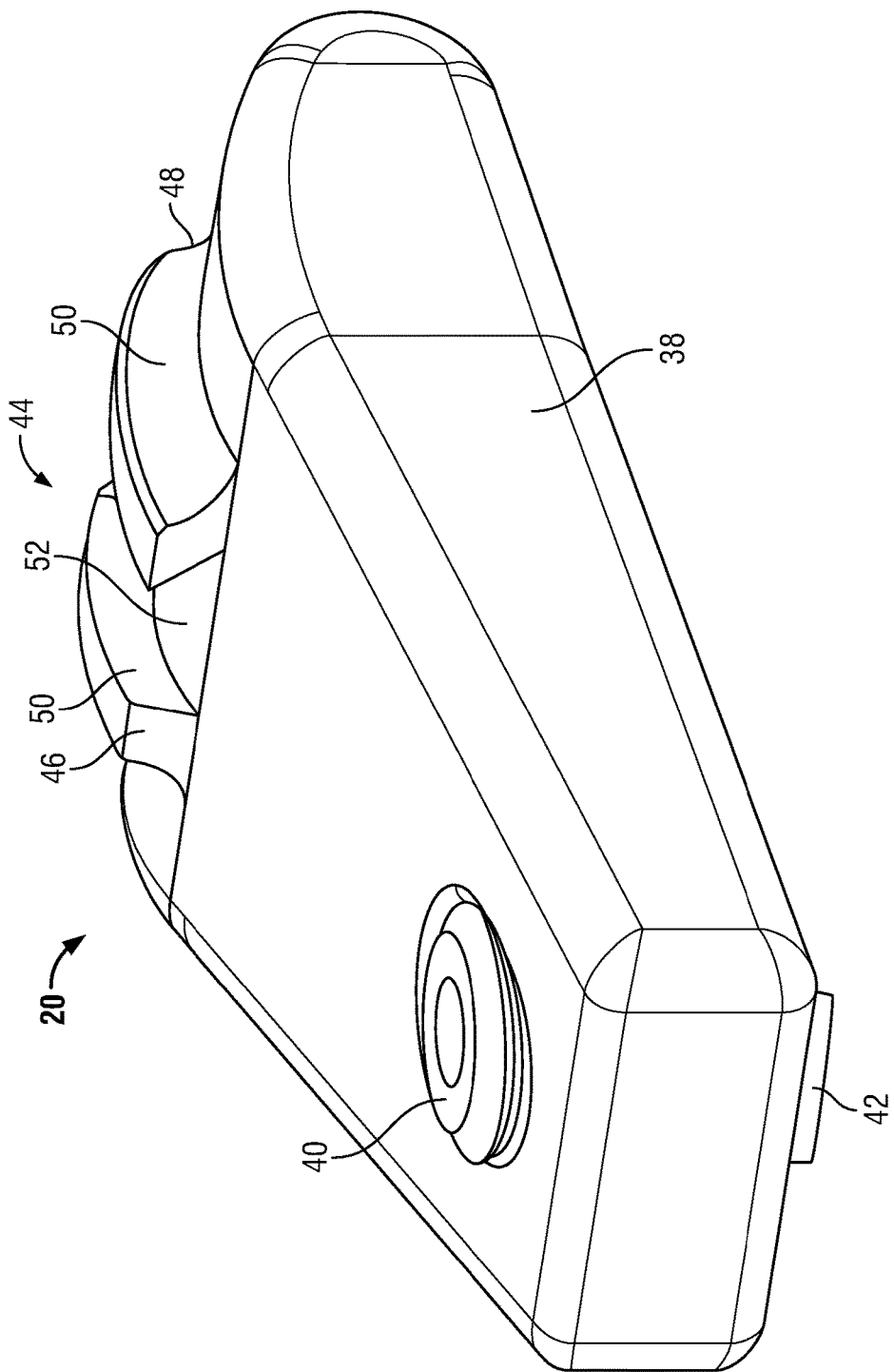
FIG. 3 shows a perspective view of the personal dispenser of the liquid master dispenser of FIG. 1.
Figure 4:
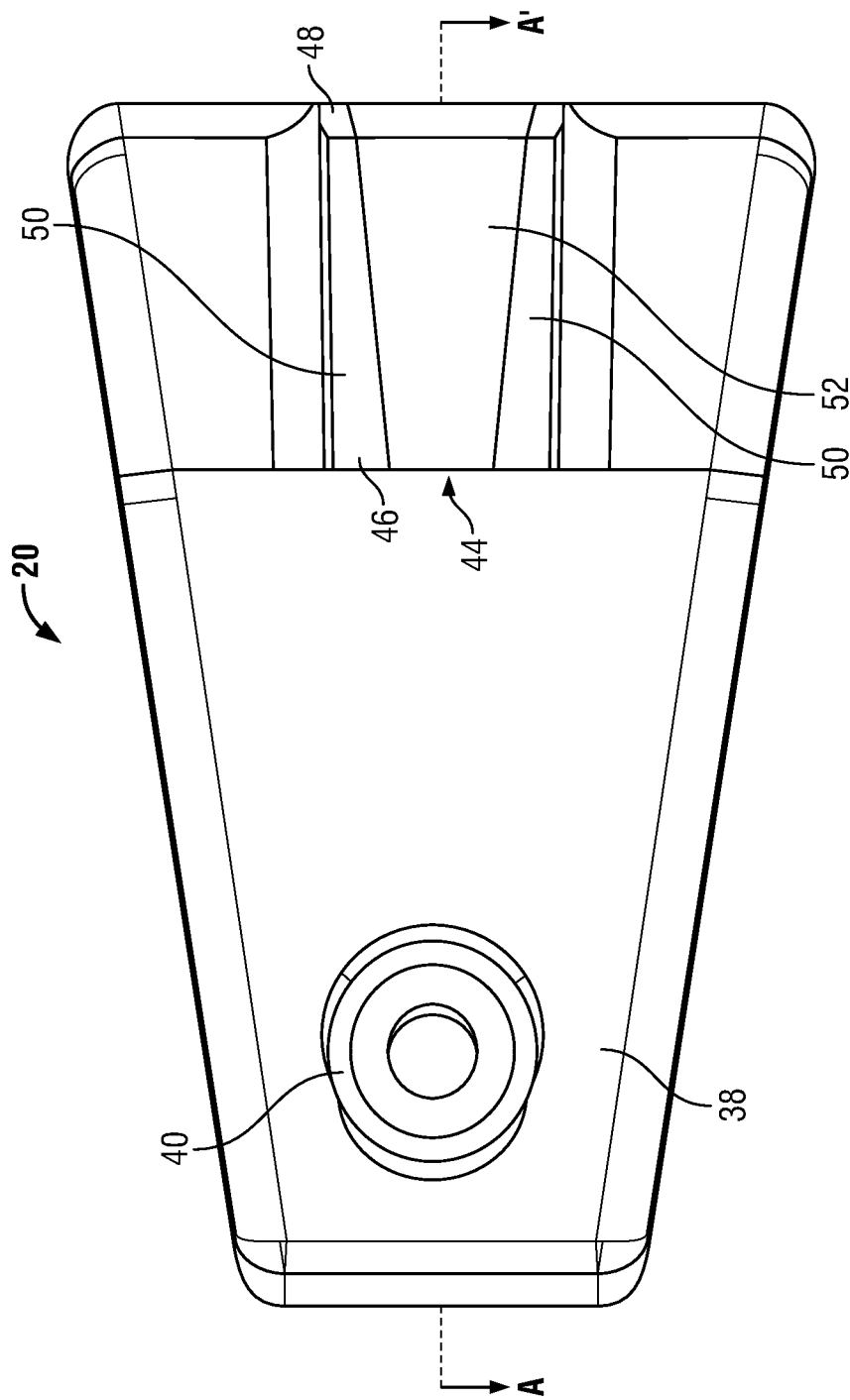
FIG. 4 shows a top view of the personal dispenser of FIG. 3.
Figure 5:
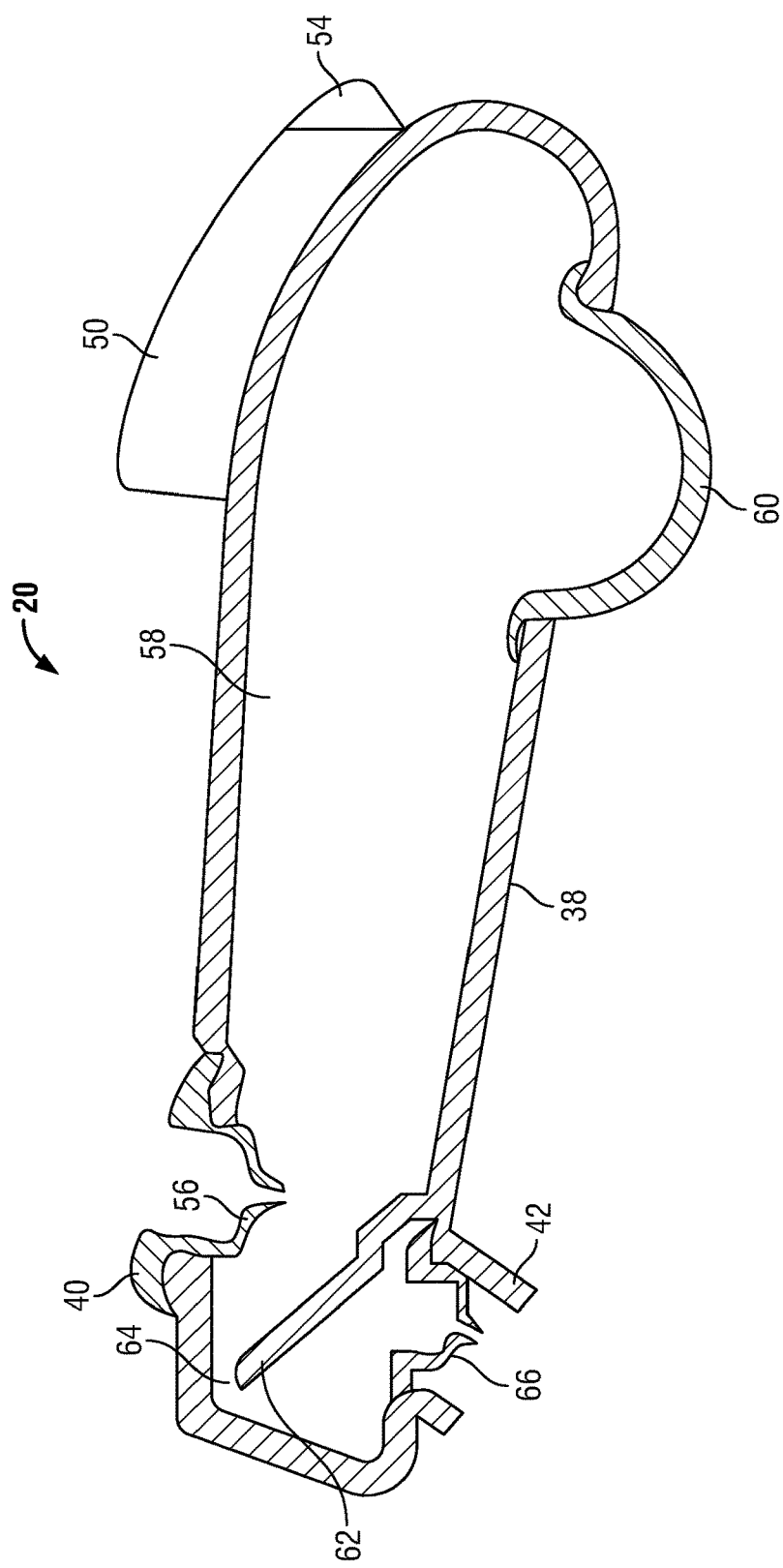
FIG. 5 shows a cross sectional view of the personal dispenser of FIG. 4, taken along line A-A'.

The personal dispenser 20 is best shown in FIGS. 3, 4 and 5 as including a receptacle 38, an inlet port 40, an outlet port 42, and a generally arcuate docking seat 44. The inlet port 40 is configured to receive the liquid discharged from the dispenser outlet 18, and is provided with a one-way inlet valve 56 that permits fluid to enter the receptacle 38 through the inlet port 40, and prevents fluid from exiting the receptacle 38 through the inlet port 40. The one-way inlet valve 56 is a duckbill valve, although any suitable one-way valve construction could be employed.

The inlet port 40 is configured so that, while the personal dispenser 20 is coupled to the spout tube 134, the inlet port 40 sealingly engages with the outlet end 26 of the spout tube 134, as best seen in FIG. 2C. This ensures that the liquid discharged from the outlet end 26 passes through the one-way inlet valve 56 and into the receptacle 38.

The receptacle 38 is configured to contain the liquid received by the inlet port 40, and defines an internal cavity 58 within which the liquid received from the inlet port 40 accumulates. The receptacle 38 incorporates a dispensing mechanism for selectively dispensing the liquid contained therein. In the embodiment shown, the dispensing mechanism is a manually compressible diaphragm pump 60.

The diaphragm pump 60 is formed as an outwardly bulging semi-spherical membrane, preferably constructed from a resiliently flexible plastic or rubber material. The diaphragm pump 60 is configured to be inwardly compressible upon application of a manual compressing force, to selectively reduce the internal volume of the cavity 58 from an uncompressed volume to a compressed volume, to thereby discharge the liquid contained in the receptacle 38 through the outlet port 42. The diaphragm pump 60 is biased toward returning to the outwardly bulging semi-spherical shape upon release of the compressing force, to return the internal volume of the cavity 58 to its uncompressed volume.

The receptacle 38 also incorporates a baffle 62 that is interposed between the inlet port 40 and the outlet port 42. The baffle 62 forms a partial barrier between the outlet port 42 and the internal cavity 58, leaving only a narrow upper channel 64 permitting fluid communication therebetween. The configuration of the baffle 62 permits the expulsion of displaced air from the receptacle 38 as the liquid accumulates therein.

The outlet port 42 is configured to discharge the liquid from the receptacle 38, and is provided with a one-way outlet valve 66 that permits fluid to exit the receptacle 38 through the outlet port 42, and prevents fluid from entering the receptacle 38 through the outlet port 42. In the embodiment shown in FIG. 5, the one-way outlet valve 66 is a duckbill valve, although any suitable one-way valve construction could be employed. Preferably, the one-way outlet valve 66 is configured to discharge fluid from the receptacle 38 only when a pressure differential across the outlet port 42 exceeds a preselected threshold. This helps to ensure that the liquid does not unintentionally leak out of the personal dispenser 20. The preselected threshold is preferably between 50 mbar and 100 mbar, and most preferably at least about 60 mbar.

The operation of the master dispenser 10 while the personal dispenser 20 is coupled thereto will now be described. To fill the personal dispenser 20 with the liquid, the pump assembly 16 is operated to discharge the liquid from the dispenser outlet 18 in the manner previously described. The liquid discharged by the dispenser outlet 18 is received by the inlet port 40, where it passes through the one-way inlet valve 56 and into the receptacle 38.

While in the coupled orientation shown in FIG. 2C, the personal dispenser 20 is oriented such that the received liquid initially pools within the internal cavity 58 below the height of the baffle 62. Meanwhile, the lower relative density of the air contained within the internal cavity 58 causes the air to sit above the liquid, in fluid communication with the outlet port 42 through the upper channel 64. As the liquid accumulates, the pressure within the internal cavity 58 rises until the preselected threshold of the one-way outlet valve 66 is reached. Once the preselected threshold is reached, the one-way outlet valve 66 opens to release the displaced air therefrom.

Eventually, the level of the liquid contained within the internal cavity 58 reaches the height of the baffle 62. At this point, most of the air initially contained within the internal cavity 58 has been expelled from the outlet port 42. As further liquid is received by the inlet port 40, the liquid spills over the baffle 62 through the upper channel 64 to the outlet port 42, to be discharged when the pressure is above the preselected threshold.

The construction of the liquid master dispenser 10 permits the liquid to be discharged while the personal dispenser 20 remains coupled to the dispenser outlet 18. In particular, once the level of liquid within the internal cavity 58 has exceeded the height of the baffle 62, allowing the liquid to pool above the outlet port 42, further pressurization of the internal cavity 58 above the preselected threshold will cause the discharge of the liquid from the outlet port 42.

One way to further pressurize the internal cavity 58 is by activating the pump assembly 16, to introduce further liquid into the receptacle 38 through the inlet port 40. This influx of liquid will increase the pressure within the internal cavity 58. Once the preselected threshold is reached, the liquid pooled above the outlet port 42 will be discharge therefrom.

The personal dispenser 20 can be easily uncoupled from the dispenser outlet 18 when desired, and is configured to sit upright on a flat support surface 15 such as a table or desk, as shown in FIG. 2B. When detached from the dispenser outlet 18, the liquid is discharged from the personal dispenser 20 by manually compressing the diaphragm pump 60. This pressurizes the cavity 58, to thereby open the one-way outlet valve 66 and discharge the liquid therefrom. The one-way inlet valve 56 furthermore allows air to enter the receptacle 38 through the inlet port 40, to replace the discharged liquid and permit the diaphragm pump 60 to return to its original outwardly bulging semi-spherical shape. The diaphragm pump 60 can then be compressed again to discharge further liquid as desired.

While the personal dispenser 20 is removed from the dispenser outlet 18, the pump assembly 16 remains operable to dispense the liquid directly from the dispenser outlet 18, as for example onto a person's hand below the outlet end 26, as shown in FIG. 2B.

Figure 6:
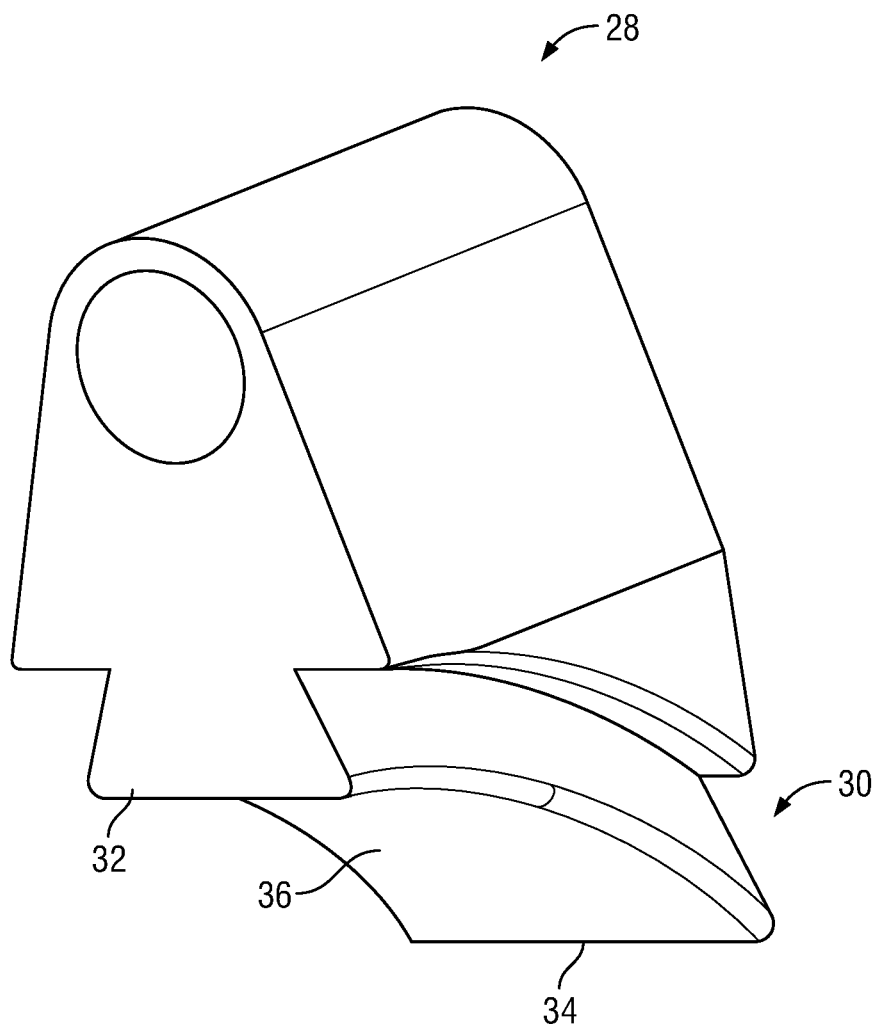
FIG. 6 shows a perspective view of a mounting dock of the liquid master dispenser of FIG. 2A.
Figure 7:
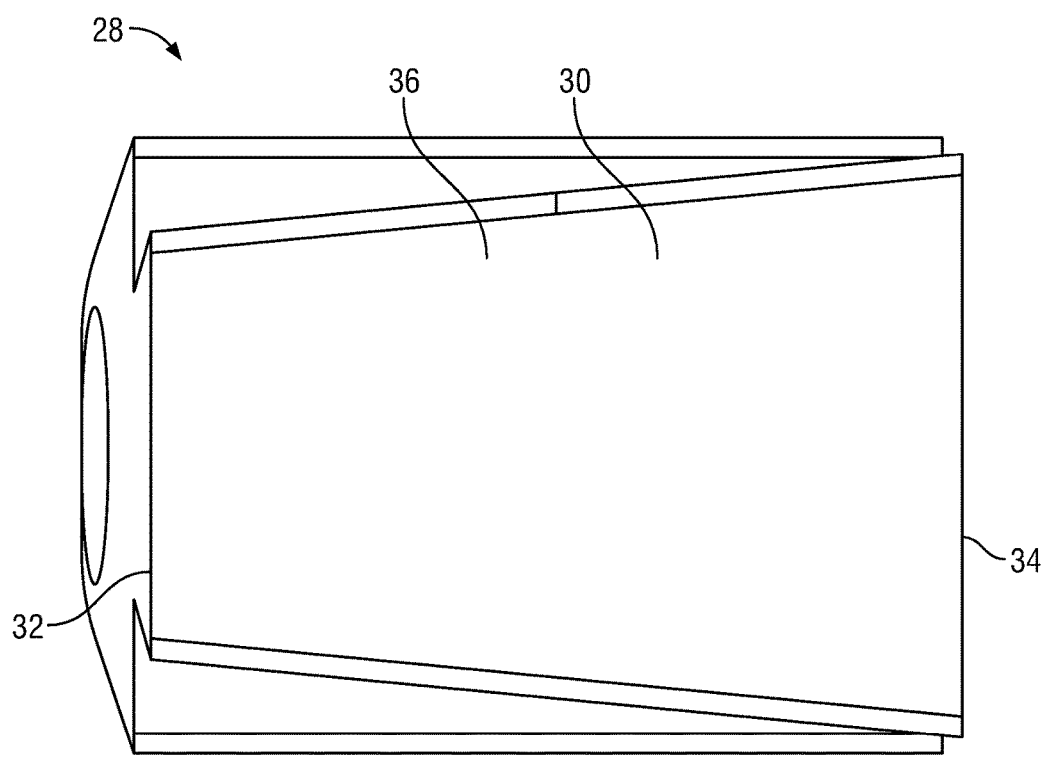
FIG. 7 shows a bottom view of the mounting dock of FIG. 6.

The structures which permit the coupling of the personal dispenser 20 to the dispenser outlet 18 will now be described in detail. As best shown in FIG. 6, the mounting dock 28 defines a generally arcuate track 30 that extends from a front end 32 to a back end 34. The front end 32 of the generally arcuate track 30 faces the outlet end 26 of the spout tube 134, and the back end 34 faces away from the outlet end 26, as shown in FIG. 2B. The generally arcuate track 30 is formed as an elongated dovetail shaped projection 36. The elongated dovetail shaped projection 36 is tapered such that a width of the elongated dovetail shaped projection 36 at the front end 32 of the generally arcuate track 30 is less than a width of the elongated dovetail shaped projection 36 at the back end 34 of the generally arcuate track 30, as is best shown in FIG. 7.

The generally arcuate docking seat 44 of the personal dispenser 20 is provided for sliding engagement with the generally arcuate track 30 of the mounting dock 28, to enable coupling and uncoupling of the personal dispenser 20 and the dispenser outlet 18. As shown in FIG. 3, the generally arcuate docking seat 44 extends from a front end 46 that faces the inlet port 40, to a back end 48 that faces away from the inlet port 40, and is formed from two docking rails 50. Together, the docking rails 50 define an elongated dovetail shaped channel 52 therebetween, which is configured to receive the elongated dovetail shaped projection 36.

As is best shown in FIG. 4, the docking rails 50 define a taper in the elongated dovetail shaped channel 52, such that a width of the elongated dovetail shaped channel 52 at the front end 46 of the generally arcuate docking seat 44 is less than a width of the elongated dovetail shaped channel 52 at the back end 48 of the generally arcuate docking seat 44. More particularly, the taper in the elongated dovetail shaped channel 52 is selected to correspond to the taper in the elongated dovetail shaped projection 36, such that the elongated dovetail shaped channel 52 and the elongated dovetail shaped projection 36 fit snugly together when the elongated dovetail shaped projection 36 is fully received within the elongated dovetail shaped channel 52.

Figure 8:
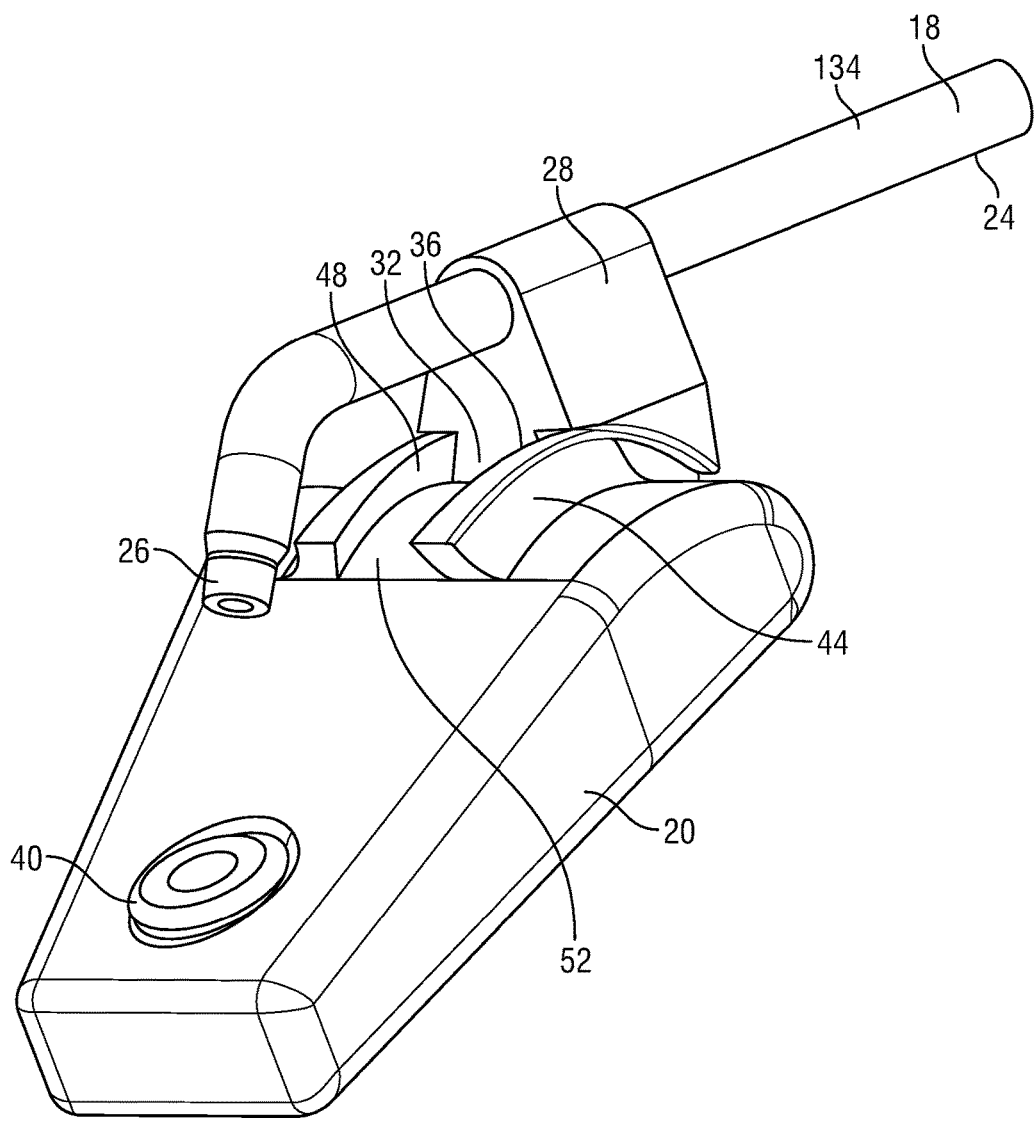
FIGS. 8 to 10 are perspective views depicting the coupling of the personal dispenser of the liquid master dispenser of FIG. 1, and showing successive relative positions moving from an initial coupling position of FIG. 8, through an intermediate position of FIG. 9, to a fully coupled position of FIG. 10.
Figure 9:
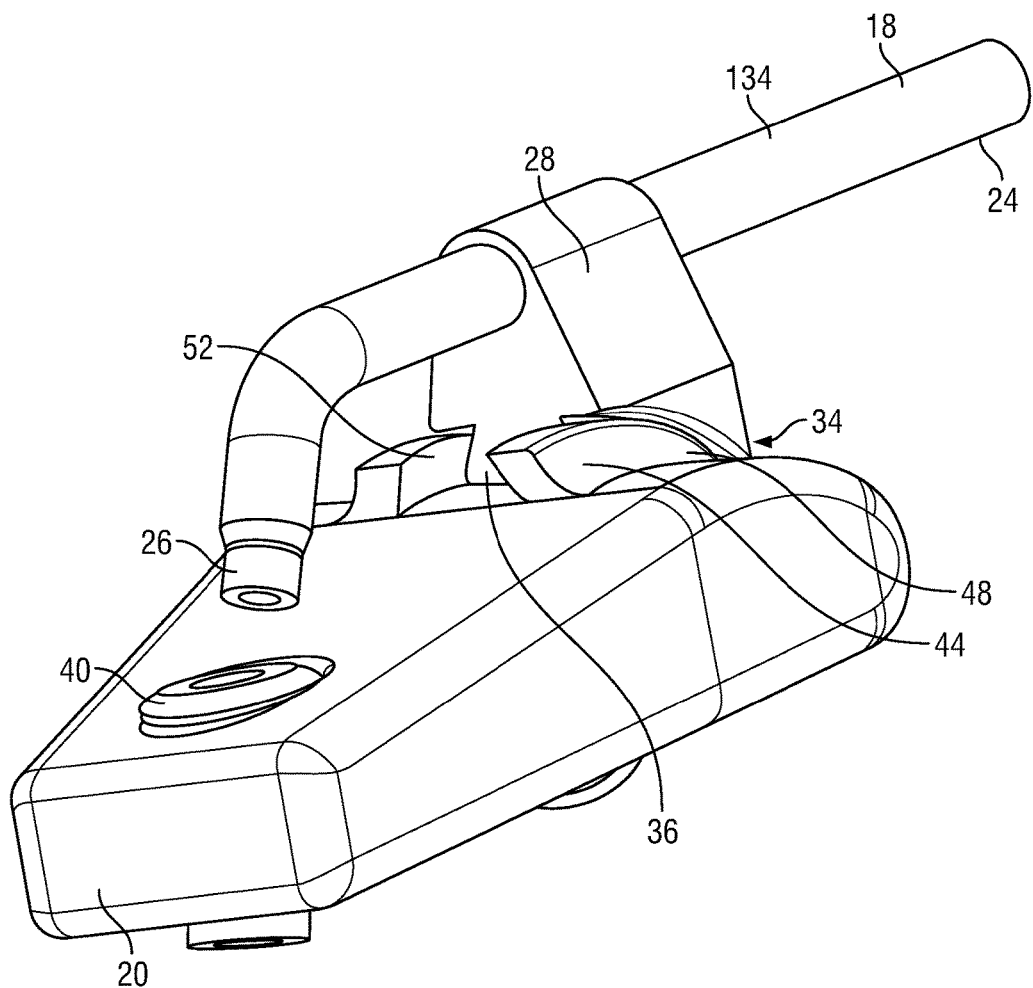

The manner by which the personal dispenser 20 is coupled with the dispenser outlet 18 will now be described with reference to FIGS. 8 to 10. As shown in FIG. 8, the front end 32 of the elongated dovetail shaped projection 36 is initially received within the back end 48 of the elongated dovetail shaped channel 52. The arrangement of the generally arcuate docking seat 44 on the personal dispenser 20 is selected such that the inlet port 40 of the personal dispenser 20 is spaced from the outlet end 26 of the spout tube 134 in this initial position.

Next, the back end 48 of the generally arcuate docking seat 44 is slid along the elongated dovetail shaped projection 36 toward the back end 34 thereof. At the same time, the curvature of the elongated dovetail shaped channel 52 and the elongated dovetail shaped projection 36 cause the inlet port 40 to move toward the outlet end 26 of the spout tube 134, as shown in FIG. 9.

Figure 10:
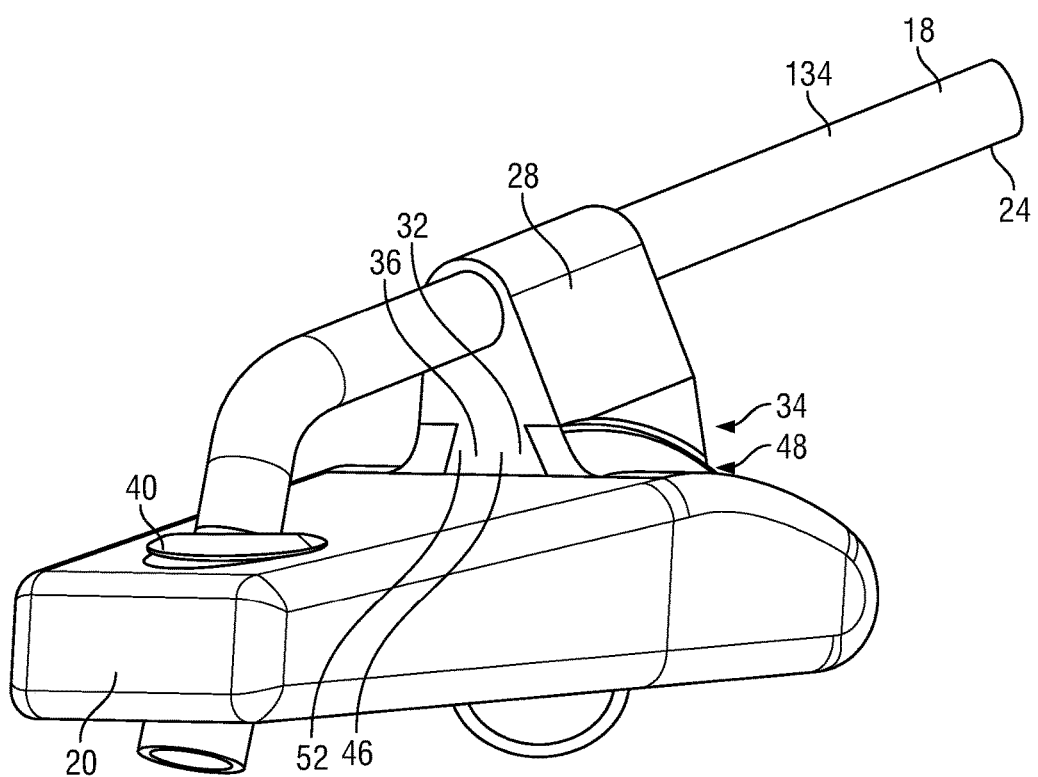

The elongated dovetail shaped channel 52 and the elongated dovetail shaped projection 36 are fully engaged once the front end 32 of the elongated dovetail shaped projection 36 is engaged with the front end 46 of the elongated dovetail shaped channel 52, and the back end 34 of the elongated dovetail shaped projection 36 is engaged with the back end 48 of the elongated dovetail shaped channel 52, as shown in FIG. 10. At this point, the outlet end 26 of the spout tube 134 is received within the inlet port 40 of the personal dispenser 20.

Figure 11:
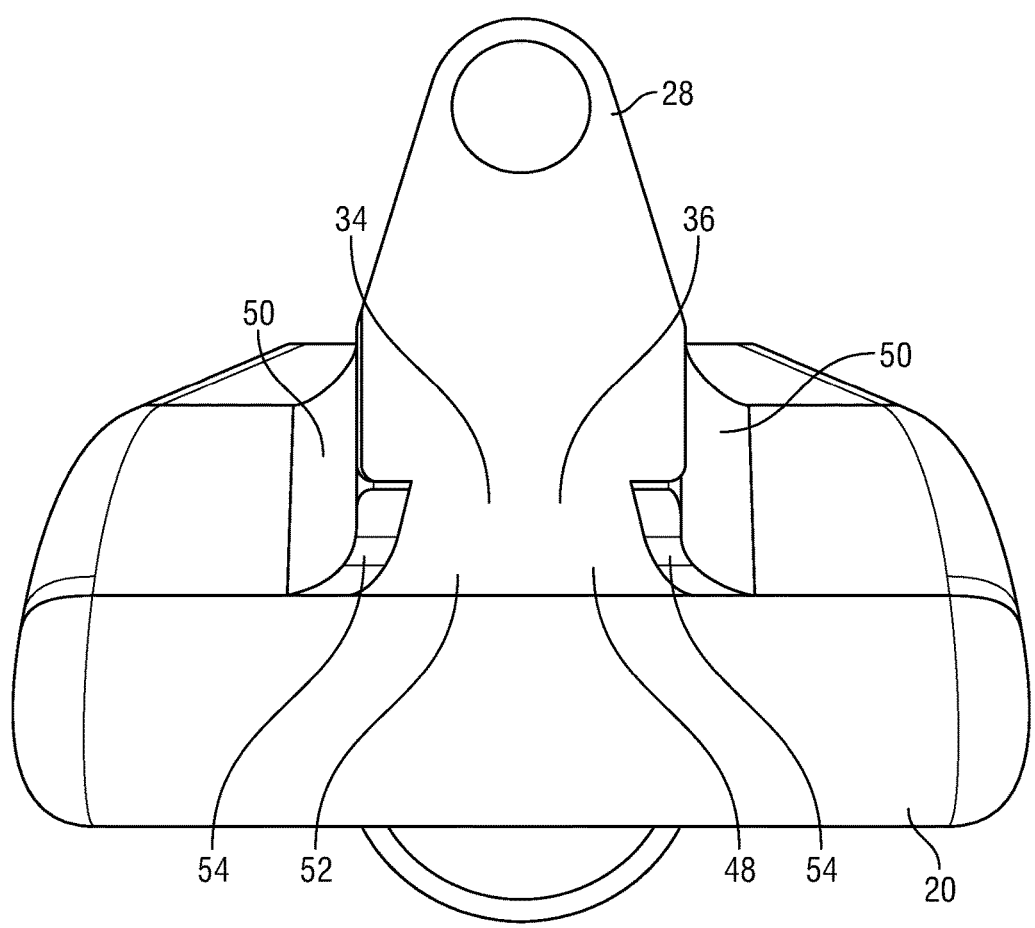
FIG. 11 shows a rear view of the personal dispenser coupled to the mounting dock taken along section line B-B' in FIG. 2A.

The corresponding tapers in the elongated dovetail shaped channel 52 and the elongated dovetail shaped projection 36 prevent the front end 46 of the elongated dovetail shaped channel 52 from sliding past the front end 32 of the elongated dovetail shaped projection 36 toward the back end 34 of the elongated dovetail shaped projection 36. As is best shown in FIG. 11, the docking rails 50 are each provided with a flexible retaining boss 54 at the back end 48 of the elongated dovetail shaped channel 52. The flexible retaining bosses 54 are configured to sit behind the elongated dovetail shaped projection 36 in a snap fit while the elongated dovetail shaped projection 36 is fully engaged with the elongated dovetail shaped channel 52, to provide a preselected resistance against the sliding removal of the elongated dovetail shaped projection 36 from the elongated dovetail shaped channel 52. A skilled artisan will appreciate that by adjusting the relative dimensions and material properties of the flexible retaining bosses 54, the degree of resistance can be adjusted. Preferably, the degree of resistance is selected so as to prevent unintentional disengagement of the elongated dovetail shaped projection 36 from the elongated dovetail shaped channel 52, while also permitting the personal dispenser 20 to be easily removed from the mounting dock 28 when so desired.

The personal dispenser 20 is removed from the mounting dock 28 by sliding the back end 48 of the elongated dovetail shaped channel 52 toward the front end 32 of the elongated dovetail shaped projection 36, until the elongated dovetail shaped channel 52 and the elongated dovetail shaped projection 36 are completely disengaged. At the same time, the curvature of the elongated dovetail shaped channel 52 and the elongated dovetail shaped projection 36 cause the inlet port 40 of the personal dispenser 20 to disengage from the outlet end 26 of the dispenser outlet 18.

The interaction of the mounting dock 28 and the docking seat 44 on the personal dispenser 20 provides one arrangement for pivotal movement of the personal dispenser 20 into engagement with the discharge outlet. Other arrangements may be used.

Figure 12:
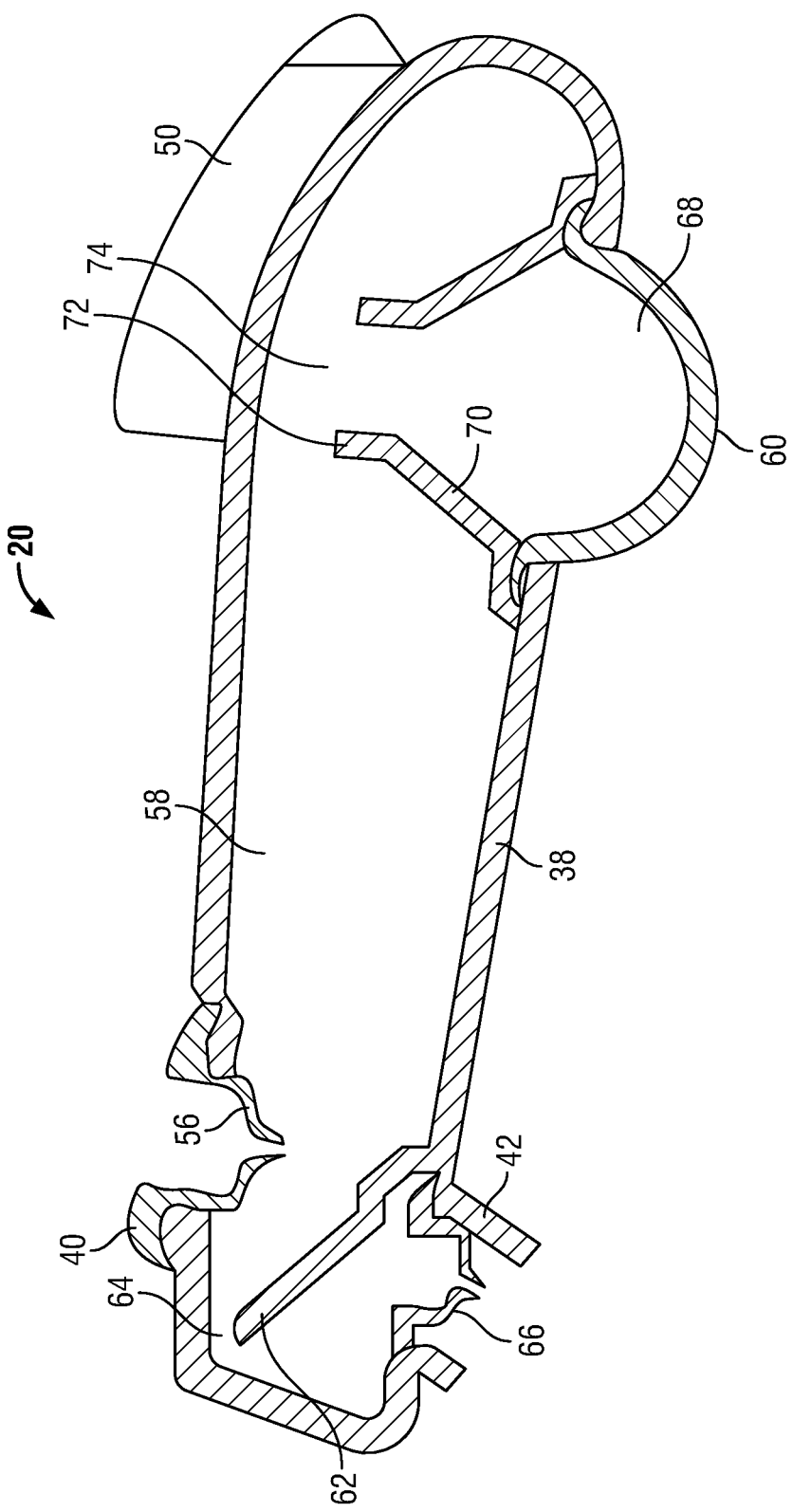
FIG. 12 shows a cross sectional view of a second embodiment of a personal dispenser similar to that shown in FIG. 5, with a first alternate construction.

A first alternate construction of the personal dispenser 20 is depicted in FIG. 12, wherein like numerals are used to identify like components. The construction depicted in FIG. 12 is generally identical to that shown in FIG. 5, with the exception that the receptacle 38 incorporates an internal chamber 68 disposed within the internal cavity 58. The internal chamber 68 is defined by a generally conical barrier wall 70 which surrounds the outer circumference of the diaphragm pump 60, and extends upwardly therefrom. The generally conical barrier wall 70 has a cylindrical upper portion 72 with an upper opening 74. The diaphragm pump 60 corresponds identically to the diaphragm pump 60 shown in FIG. 5 and described above, with the exception that the diaphragm pump 60 is completely or partially transparent, to permit visual inspection of the contents of the internal chamber 68.

While the personal dispenser 20 is coupled to the dispenser outlet 18, the generally conical barrier wall 70 prevents liquid received by the inlet port 40 from entering the internal chamber 68 until the level of the liquid reaches the height of the upper opening 74. Preferably, the height of the upper opening 74 is selected such that liquid will only enter the internal chamber 68 once the internal cavity 58 is almost completely full. This allows the presence or absence of liquid within the internal chamber 68 to serve as an indicator of whether or not the receptacle 38 is full. The presence or absence of liquid within the internal chamber 68 can furthermore be easily determined through visual inspection of the transparent diaphragm pump 60. In some embodiments, the liquid is coloured to be more readily visible through the transparent diaphragm pump 60.

Figure 13:
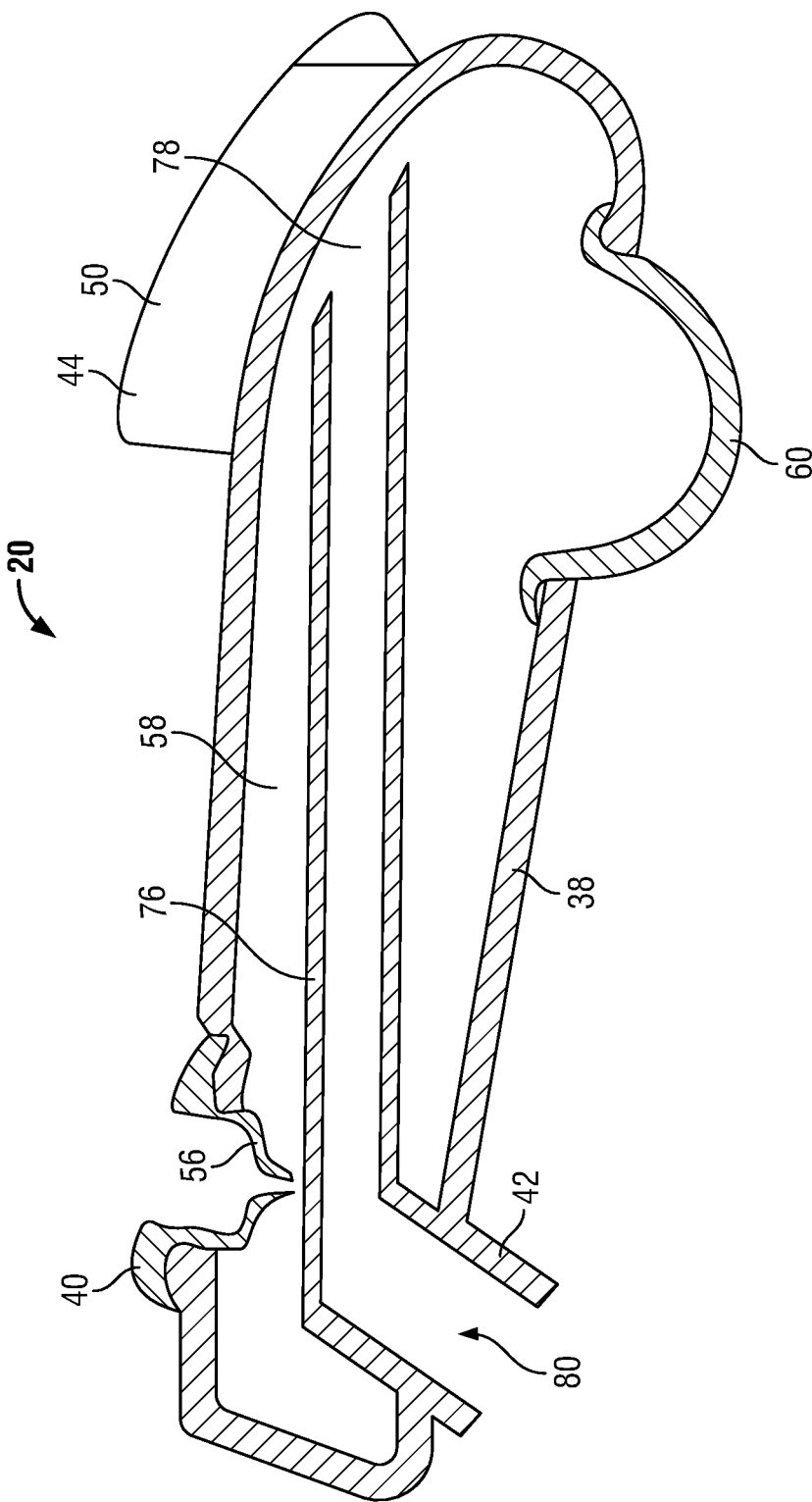
FIG. 13 shows a cross sectional view of a third embodiment of a personal dispenser similar to that shown in FIG. 5, with a second alternate construction.

A second alternate construction of the personal dispenser 20 is depicted in FIG. 13, wherein like numerals are used to identify like components. The construction depicted in FIG. 13 is generally identical to that shown in FIG. 5, with the exception that the baffle 62 has been omitted, and the outlet port 42 is formed as an elongated tubular member 76. The tubular member 76 extends from an inlet opening 78 disposed proximate to the generally arcuate docking seat 44 within the internal cavity 58, to a discharge opening 80 that protrudes out of the receptacle 38. Similar to the baffle 62 in the constructions described above, the height of the inlet opening 78 of the tubular member 76 prevents liquid received by the inlet port 40 from entering the outlet port 42 until the level of the liquid has reached the height of the inlet opening 78. This ensures that most of the air contained within the internal cavity 58 is expelled from the outlet port 42 before any liquid is discharged therefrom, in much the same way as the baffle 62 in the constructions described above.

Furthermore, when the personal dispenser 20 is removed from the master dispenser 10 and held manually upright or stood upright as shown in FIG. 2B, the orientation of the tubular member 76 causes the inlet opening 78 to sit near the bottom of the personal dispenser 20. This allows almost all of the liquid contained in the receptacle 38 to be selectively discharged while in the upright position. In particular, the orientation of the tubular member 76 ensures that the inlet opening 78 remains in fluid communication with the liquid pooled at the bottom of the receptacle 38, even when the receptacle 38 is nearly empty.

The reservoir 12 may be replaced once the liquid contained therein has been depleted. When the reservoir 12 is empty, the personal dispenser 20 may advantageously be used as a backup supply of the liquid. The presence of this backup supply permits and may encourage users to wait until the reservoir 12 is completely empty before replacing the reservoir 12, and thus reduce the amount of liquid that is wasted when a replaceable reservoir 12 is replaced before it is completely empty.

Referring again to FIGS. 1 and 2C, both of these figures show the same condition in which the personal dispenser 20 is coupled to the master dispenser 10 and the piston forming element 402 is in an uppermost position under the bias of the spring 126 as permitted by the actuator 22. In this coupled position as seen in FIG. 1, the personal dispenser 20 is below the shroud 19 with a lower profile of the shroud 19 and an upper profile of the personal dispenser 20 matching each other so as to provide a pleasing visual appearance. From the position of FIGS. 1 and 2C, on movement of the front distal end of the manual actuator 22 downwardly, the piston forming element 402 is moved downwardly relative to the piston chamber forming body 401. Since the piston chamber forming body 401 is fixed to the housing 14, the piston forming element 402 together with the discharge outlet 18 and the personal dispenser 20 are moved vertically relative to the shroud 19 and the housing 14 with operation of the pump assembly 16.

Figure 14:
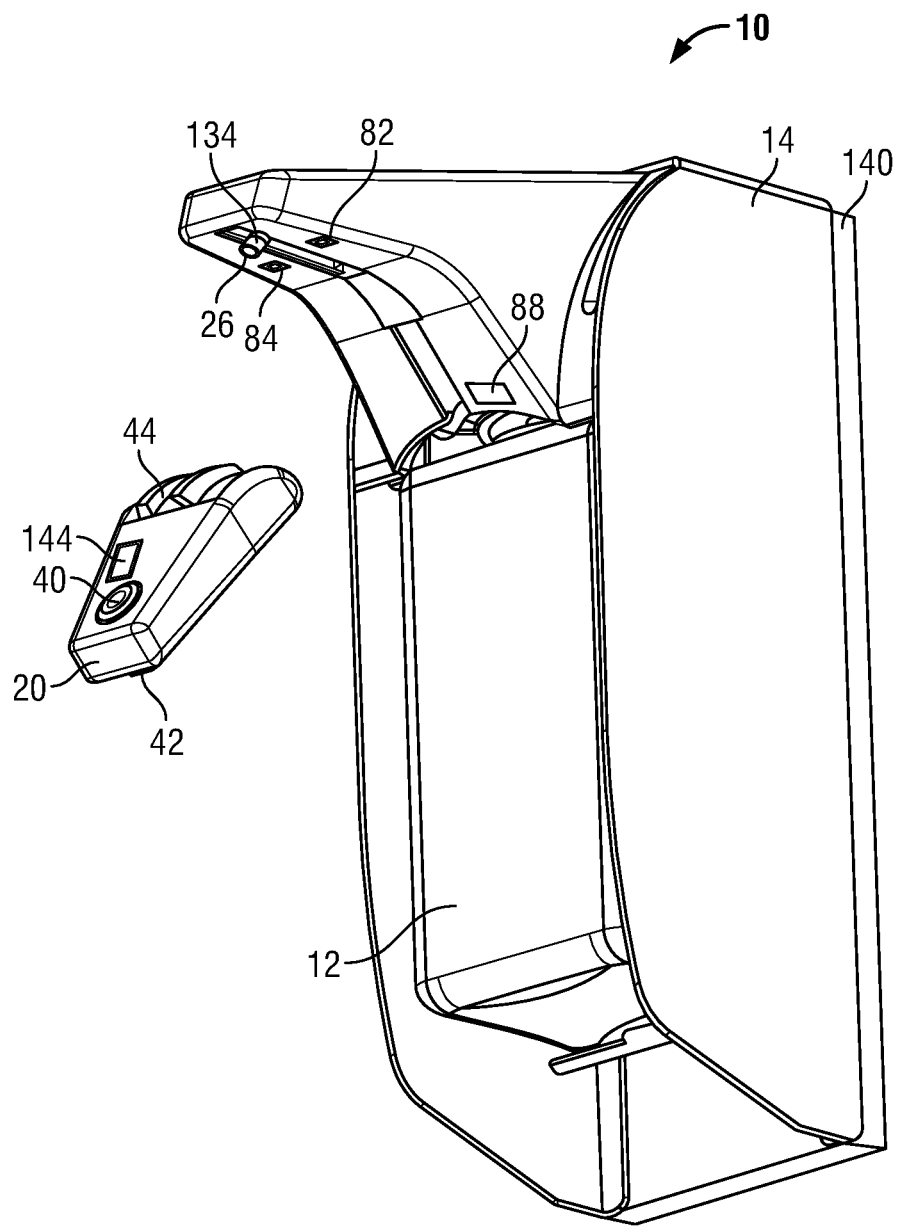
FIG. 14 shows a perspective view of a liquid master dispenser in accordance with a second preferred embodiment of the invention with a personal dispenser in an uncoupled state.

FIG. 14 shows a liquid master dispenser 10 in accordance with a second preferred embodiment of the invention, wherein like reference numerals are used to denote like components. The liquid master dispenser 10 according to the second preferred embodiment is identical to the liquid master dispenser 10 according to the first preferred embodiment, with the exception that the manual actuator 22 has been omitted, and the master dispenser 10 has been adapted to incorporate electronic components to permit automatic and touchless activation of the pump assembly 16. The master dispenser 10 may, for example, incorporate features similar to those described in U.S. Pat. No. 5,836,482 to Ophardt et al., issued Nov. 17, 1998, and United States Publication No. US 20090045221 to Ophardt et al., published Feb. 19, 2009, both of which are incorporated herein by reference.

Figure 15:
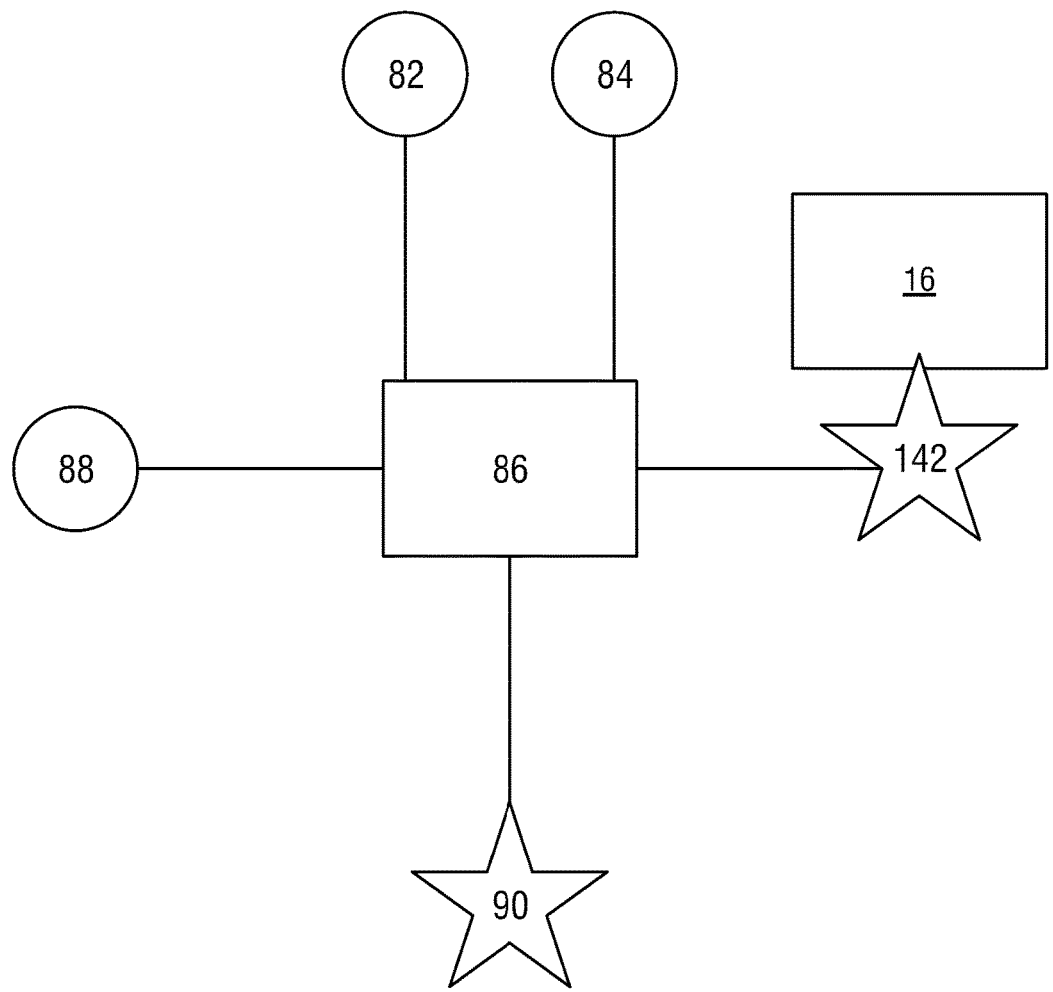
FIG. 15 is a schematic diagram of a control circuit for the dispenser of FIG. 14.

The master dispenser 10 incorporates a back panel 140 which is coupled to the housing 14 and carries various additional components for touchless operation of the master dispenser 10 including the provision as schematically shown on FIG. 15 of an electric motor 142 which when activated moves the piston element 402 in a cycle of operation to dispense an allotment of fluid from the pump assembly 16, various sensors 82, 84 and 88, a central processing unit 86, and a communication system 90. The central processing unit 86 is connected to various electronic components, as shown schematically in FIG. 15. The central processing unit 86 acts as a control system for the pump assembly 16, and is able to activate the pump assembly 16 using the electric motor 142.

The housing 14 of the master dispenser 10 is modified to incorporate infrared sensors 82 and 84, which are positioned adjacent to the outlet end 26 of the spout tube 134. The personal dispenser sensor 82 is configured to detect if the personal dispenser 20 is coupled to the spout tube 134. The sensor 82 comprises an emitter of infrared radiation and a sensor of infrared radiation. The sensor 82 is able to detect changes in infrared radiation emitted that is received by its sensor, and is calibrated to recognize the infrared radiation that is sensed due to reflection from the personal dispenser 20 when the personal dispenser 20 is placed immediately adjacent to the sensor 82, as occurs when the personal dispenser 20 is coupled to the spout tube 134.

The fluid level sensor 84 is configured to detect if the receptacle 38 of the personal dispenser 20 contains a preselected volume of the liquid. The sensor 84 comprises an emitter of infrared radiation and a sensor of infrared radiation. To enable the operation of the sensor 84, the personal dispenser 20 is provided with a transparent window 144 which permits infrared radiation to pass therethrough. The window 144 is positioned to align with the sensor 84 when the personal dispenser 20 is coupled to the spout tube 134 so that infrared radiation from the emitter of the sensor 84 passes through the window 114 into the receptacle 38, and the sensor of the sensor 84 receives infrared radiation reflected from within the receptacle 38 back out through the window 144. The sensor 84 is able to detect changes in the infrared radiation reflected back through the window 144 from within the receptacle 38. The sensor 84 is calibrated to recognize the change in infrared radiation that occurs when the liquid within the receptacle 38 rises to one or more heights including preferably a height corresponding to the preselected volume.

An additional infrared hand sensor 88 is also incorporated into the housing 14 near the spout tube 134. The sensor 88 is configured to detect the presence of a user's hand immediately below the outlet end 26 when the personal dispenser 20 is removed, and below the outlet port 42 when the personal dispenser 20 is coupled to the spout tube 134. The sensor 88 comprises an emitter of infrared radiation and a sensor of infrared radiation. The sensor 88 is calibrated to recognize the change in infrared radiation that occurs when a person's hand is held in the area below the spout tube 134. The sensors 82, 84 and 88 are linked to the central processing unit 86 by being wired or wireless connections as schematically shown on FIG. 15.

During operation, the master dispenser 10 is configured to automatically fill or refill the personal dispenser 20. In particular, the sensor 82 is configured to detect the coupling of the personal dispenser 20 to the spout tube 134, and to communicate this information to the central processing unit 86. This triggers the central processing unit 86 to activate the pump assembly 16 via the electric motor 142, to pump the liquid from the reservoir 12 out through the spout tube 134 and into the receptacle 38 of the personal dispenser 20. The pump assembly 16 remains activated until the sensor 84 detects that the receptacle 38 is full to the preselected volume, and transmits this information to the central processing unit 86. The central processing unit 86 then deactivates the pump assembly 16.

After the personal dispenser 20 has been filled and while the personal dispenser 20 is coupled to the spout tube 134, the pump assembly 16 can be activated to discharge the liquid from the master dispenser 10. In particular, the central processing unit 86 is configured to activate the pump assembly 16 when the sensor 88 detects the presence of a user's hand underneath the spout tube 134. This occurs regardless of whether or not the personal dispenser 20 is coupled to the spout tube 134, and regardless of the volume of liquid contained within the personal dispenser 20.

In a preferred embodiment of the invention, the master dispenser 10 is configured for monitoring hand cleaning compliance by automatically recording the amount of liquid that is discharged from the spout tube 134. Since the master dispenser 10 is constructed such that both (i) the liquid that is used to fill the personal dispenser 20, and (ii) the liquid that is directly dispensed, as for example onto a user's hand, are discharged from the spout tube 134, both uses of the liquid (i) and (ii) are automatically taken into account. This may be useful, for example, in a hospital setting where both personal dispensers 20 and stationary master dispensers 10 are frequently used, and the use of which must both be monitored in order to accurately assess hand cleaning frequency.

Information indicative of the amount of liquid dispensed may be collected, for example, by recording each activation of the pump assembly 16; by monitoring the volume of the liquid within the reservoir 12; and/or by detecting the flow of liquid through the pump assembly 16 or the spout tube 134. This information is collected by the central processing unit 86, which may transmit the information via the communication system 90 to a central computer, where it can be compiled and made available to hospital staff. The monitoring system may, for example, operate in a similar manner to that described in the applicant's co-pending Canadian Patent Application No. 2865608, which is incorporated by reference in its entirety.

In a dispenser as shown in FIG. 14, the personal dispenser 20 is advantageously able to act as a manual backup pump in the event that the master dispenser 10 loses power, as explained below with reference to FIG. 2C, assuming that the lever 22 is to be moved by the electric motor 142 not shown in FIG. 2C. If power is lost, with the result that the electric motor 142 is inoperable, while the personal dispenser 20 is coupled to the master dispenser 10 as seen in FIG. 2C, the internal cavity 58 of the receptacle 38 can be manually pressurized through compression of the diaphragm pump 60, to thereby discharge the liquid contained in the receptacle 38 out the outlet port 42 onto the user's hand 17. The diaphragm pump 60 is biased toward returning to its outwardly bulging semi-spherical shape upon release of the manual compressing force so as to increase the volume of the internal cavity 58 and produce a resulting drop in pressure or vacuum within the internal cavity 58 of the receptacle 38 sufficiently great to draw the liquid contained in the reservoir 12 into the receptacle 38. That is, the vacuum pressure within the internal cavity 58 of the receptacle 38 is sufficiently great to draw liquid through the one-way inlet valve 56 and through the pump assembly 16. In this regard, the vacuum is sufficient to draw fluid in the reservoir 12 up through the dip tube 128, through the one way valve 132, the piston chamber 124, the one-way valve 130, the internal conduit 120 and the one-way inlet valve 56, and into the internal cavity 58 of the receptacle 38. In this way, the liquid may be manually drawn from the reservoir 12 and out through the outlet port 42 in individual allotments through repeated manual compression and release of the diaphragm pump 60.

Reference is made to FIGS. 16 to 22 which show a liquid master dispenser 10 in accordance with a third preferred embodiment of the invention, wherein like reference numerals are used to denote like components. As in the embodiments described above, the master dispenser 10 includes a reservoir 12, a housing 14, a pump assembly 16, a dispenser outlet 18, and a personal dispenser 20. The master dispenser 10 may have a similar construction to that disclosed in U.S. Pat. No. 7,984,825 to Ophardt et al., issued Jul. 26, 2011; U.S. Pat. No. 8,684,236 to Ophardt, issued Apr. 1, 2014; and/or the applicant's co-pending Canadian Patent Application No. 2839615, which are each incorporated herein by reference.

Figure 16:
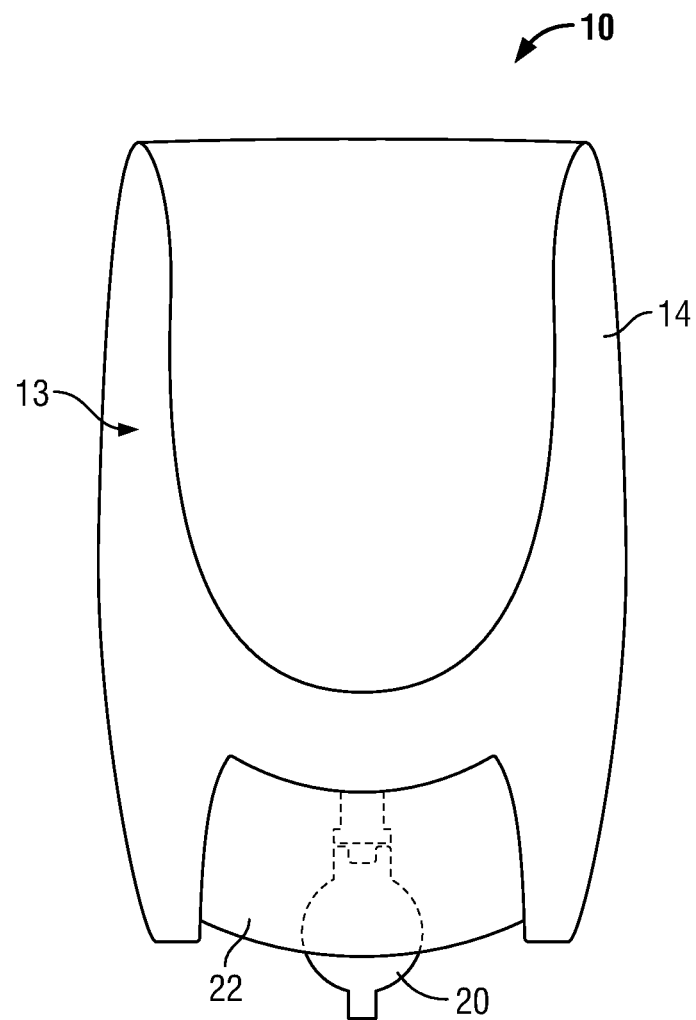
FIG. 16 shows a front view of a liquid master dispenser in accordance with a third preferred embodiment of the invention with a personal dispenser in a coupled state.
Figure 22:
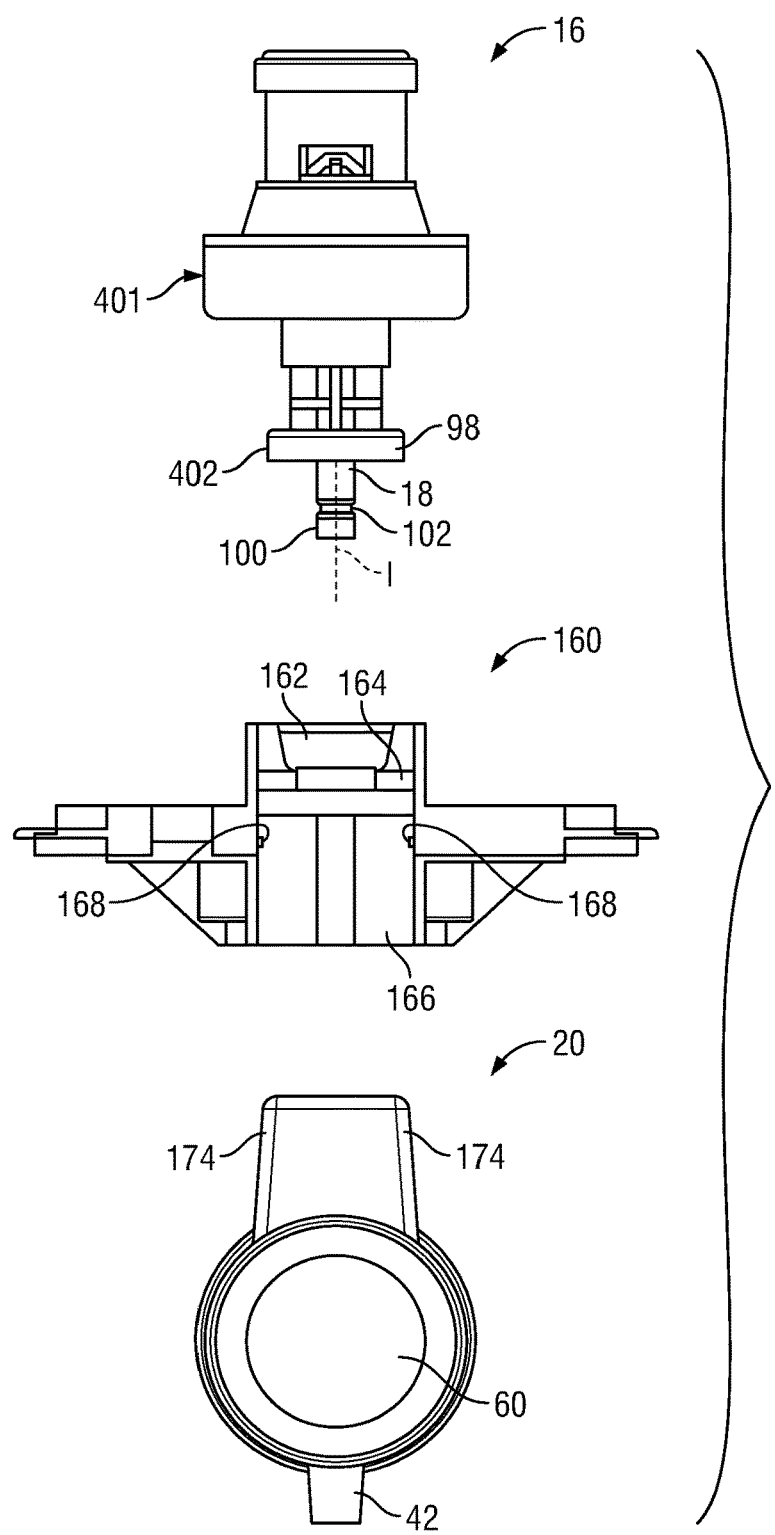
FIG. 22 shows a schematic front view of the pump assembly, an actuator plate, and the personal dispenser of the dispenser of FIG. 16.

FIG. 16 shows a front view in which a front cover 13 can be seen as well as a manual actuator 22, with lowermost portions of a personal dispenser 20 extending downwardly below the manual actuator 22. The front cover 13 is coupled to the housing 14 shown in FIG. 16 in a conventional manner as by being hingedly coupled thereto for movement about a hinge axis 11 from a closed position as seen in FIG. 16 enclosing the reservoir 12 and an open position shown in FIG. 18 in which the housing 14 and reservoir 12 are accessible. The housing 14 is schematically shown in FIG. 18 as having a back plate 510 adapted for attachment to a wall. A support plate 511 is fixed to the back plate 510 and extends forwardly to removably support the piston chamber forming body 401 of the pump assembly 16 and thereby the reservoir 12 and the piston forming element 402. An actuator plate 160 is schematically shown as mounted to the housing 14 for reciprocal upward and downward sliding movement relative the support plate 511. Spring members 512 are shown disposed between the support plate 511 and the actuator plate 160 to bias the actuator plate 160 downwardly away from the support plate 511. The actuator plate 160 removably engages the piston forming element 402. The front cover 13 carries a manual actuator 22 shown only in FIGS. 16 and 17 which, when the front cover 13 is in the closed position, is mechanically coupled between the housing 14 and the actuator plate 160 in such a way that manual movement of the manual actuator 22 causes the actuator plate 160 to slide upwards relative the support plate 511 against the bias of the spring members 512. The actuator plate 160 is best shown in FIG. 22 as having an upper chamber 162 with an actuation flange 164 for engagement with the piston forming element 402 of pump assembly 16, and a lower chamber 166 with a pair of small lateral protrusions 168 for engagement with the personal dispenser 20.

The reservoir 12, the pump assembly 16, the dispenser outlet 18, and the personal dispenser 20 are coupled to form a replaceable cartridge 94, which is shown in FIG. 18. The reservoir 12 is a container for holding the liquid to be dispensed from the liquid dispenser 10. The liquid is preferably hand soap or hand sanitizer. The bottom of the reservoir 12 is provided with a reservoir outlet 96, which is coupled to the piston chamber forming body 401 of pump assembly 16.

Figure 19:
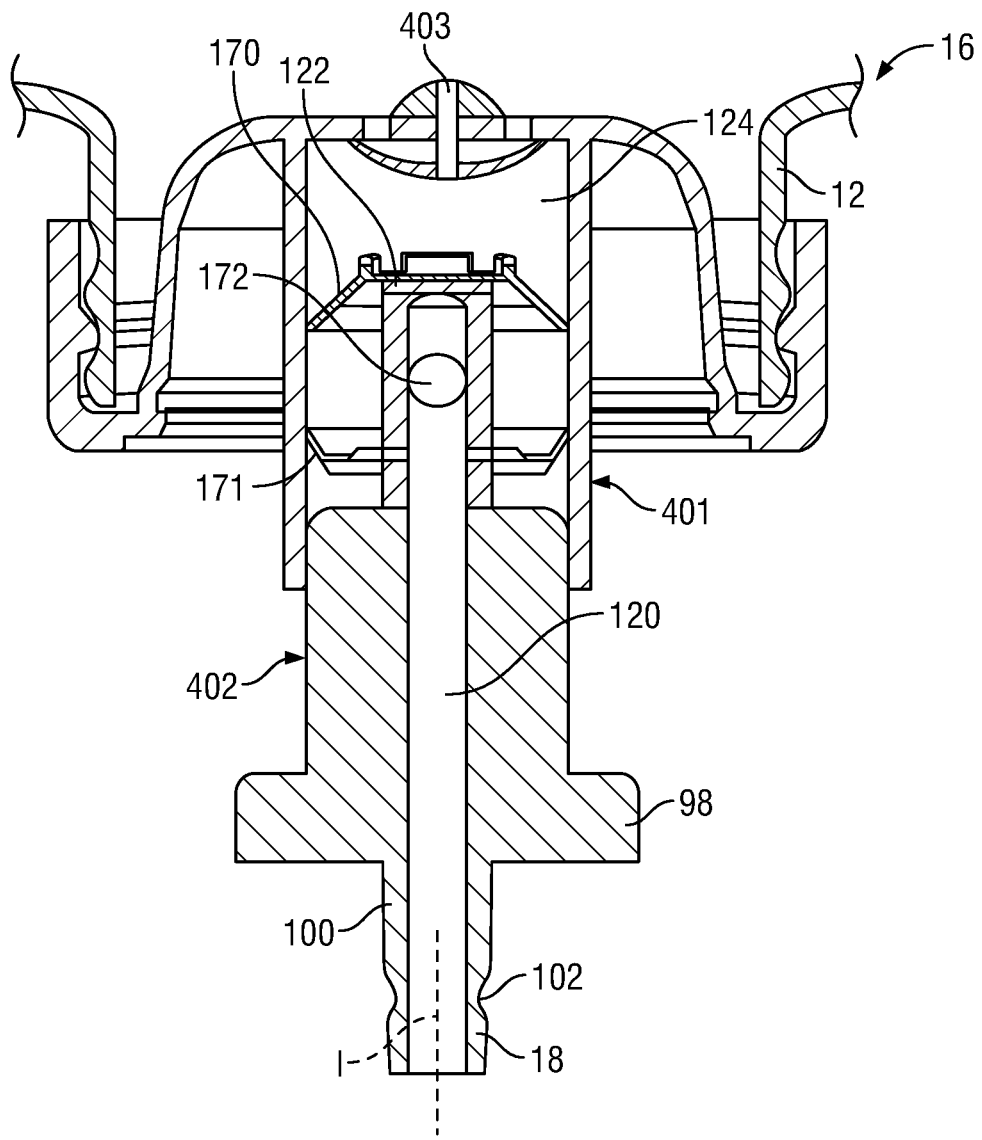
FIG. 19 shows a cross-sectional front view of a pump assembly of the replaceable cartridge of FIG. 18.

The pump assembly 16 is shown in FIG. 19 with the piston chamber forming body 401 threadably secured to the outlet 96 of the reservoir 12. The piston forming element 402 of the pump assembly 16 includes an actuation collar 98, configured to removably be received within the upper chamber 162 of the actuator plate 160 to couple the piston forming element 402 and the actuator plate 160, such that with reciprocal upwards and downwards movement of the actuator plate 160 the piston forming element 402 is reciprocally moved coaxially relative the piston chamber forming body 401 to pump the liquid from the reservoir 12 out through the dispenser outlet 18. Thus, by manual movement of the manual actuator 22, an upwards mechanical force is applied to the actuation collar 98 and transferred to the piston forming element 402 to pump the liquid from the reservoir 12.

The internal structure of the pump assembly 16 is best shown in FIG. 19. As in the previously described embodiments, the pump assembly 16 includes a piston forming element 402 with a piston 122 that is positioned within a piston chamber 124 defined within the piston chamber forming body 401. The dispenser outlet 18 is in fluid communication with the piston 122 via an internal conduit 120 with a one-way valve 403 across the conduit permitting flow outwardly from the reservoir 12 but preventing flow inwardly into the reservoir 12. The piston 122 is provided with an inner disc 170 which acts as a one-way valve to permit pressurized liquid between the inlet valve 403 and the inner disc 170 to flow outwardly past inner disc 170 in the piston chamber 124, and prevents liquid from flowing inwardly therepast. The piston 122 is provided with a sealing disc 170 which prevents liquid from flowing outwardly therepast in the piston chamber 124. With upward movement of the piston 122 relative the piston chamber forming body 401 in a retraction stroke, the liquid within the piston chamber 124 between the inlet valve 403 and the inner disc 170 is forced past the inner disc 170 and through an opening 172 into the internal conduit 120 of the hollow stem of the piston forming element 402 and out the dispenser outlet 18. With downward movement of the piston 122 relative the piston chamber forming body 401 in a withdrawal stroke, the volume between the inlet valve 403 and the inner disc 170 increases drawing liquid from the reservoir 12 outwardly past the inlet valve 403.

The dispenser outlet 18 is formed as a short outlet tube 100 that extends from the pump assembly 16 along an insertion axis I. A coaxial annular groove 102 is formed on the external surface of the outlet tube 100.

Figure 20:
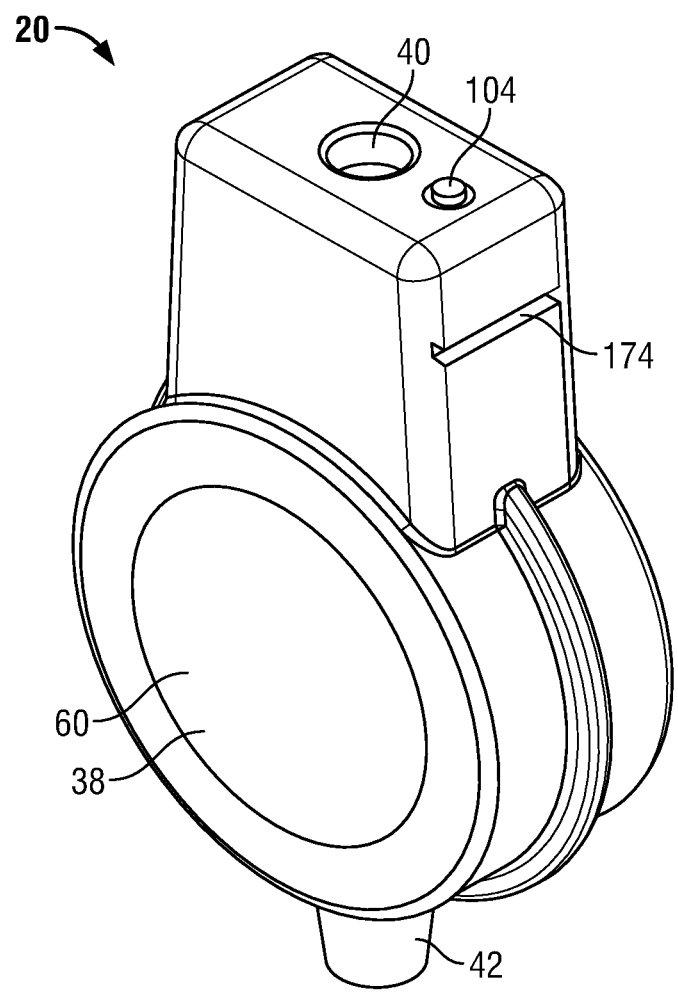
FIG. 20 shows a perspective view of a personal dispenser of the replaceable cartridge of FIG. 16.

The personal dispenser 20 is best shown in FIG. 20. As in the embodiments described above, the personal dispenser 20 includes a receptacle 38, an inlet port 40, and an outlet port 42. In addition, the personal dispenser 20 incorporates a pressure relief valve 104 and lateral channels 174. As in the previous embodiments, the inlet port 40 is configured to receive the liquid discharged from the dispenser outlet 18; the receptacle 38 is configured to contain the liquid received by the inlet port 40; and the outlet port 42 is configured to discharge the liquid from the receptacle 38.

Figure 17:
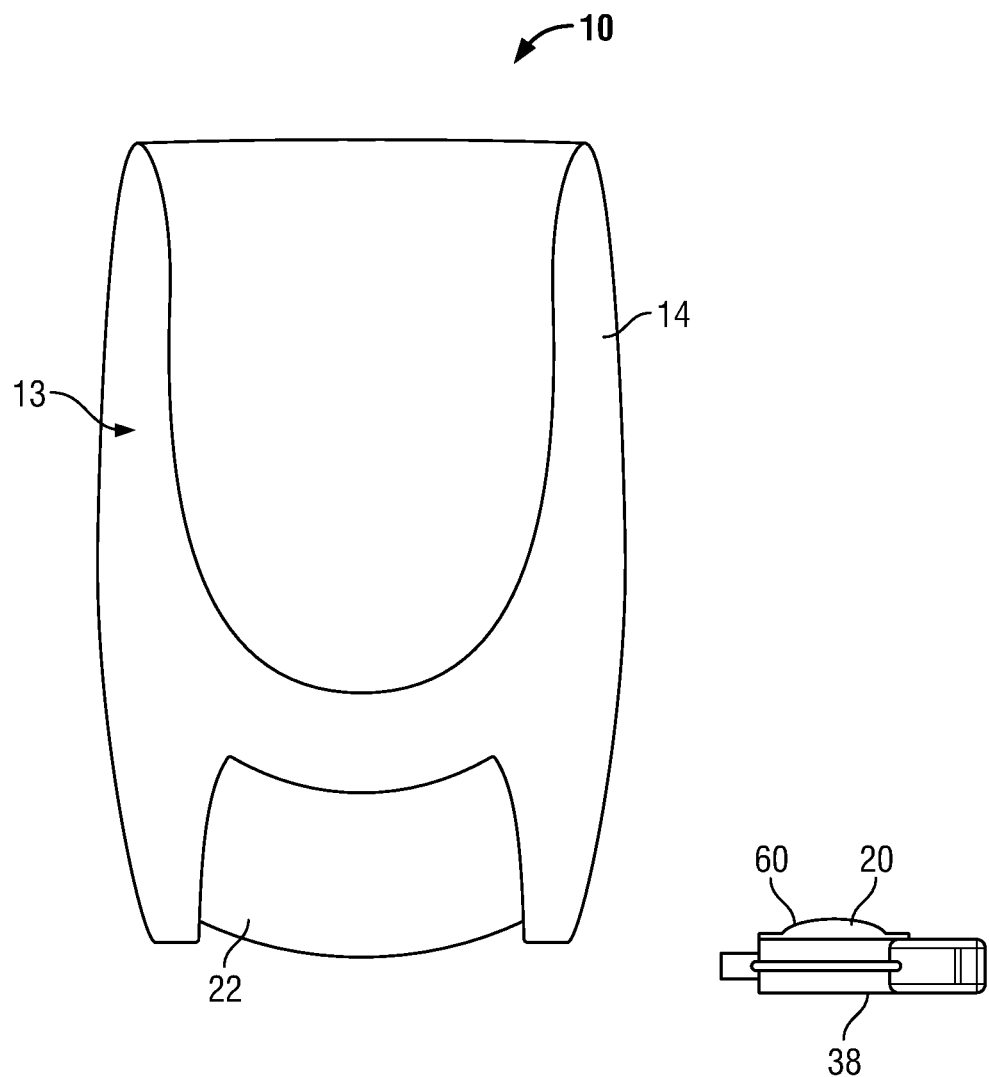
FIG. 17 shows a front view of FIG. 16 with the personal dispenser in an uncoupled state.
Figure 18:
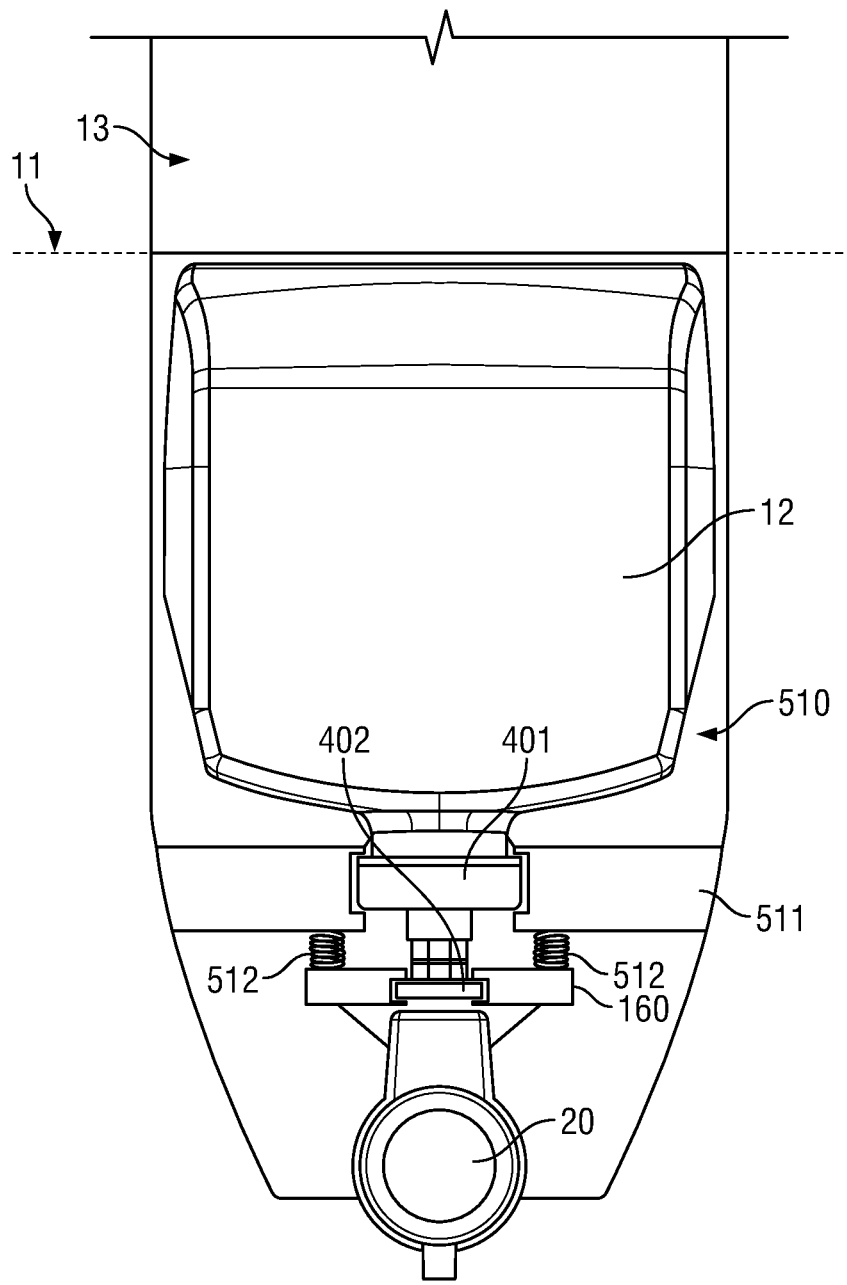
FIG. 18 shows a front view of a replaceable cartridge of the liquid master dispenser of FIG. 16 with the personal dispenser in a coupled state.

As is best shown in FIG. 17, the receptacle 38 incorporates an outwardly bulging diaphragm pump 60. As in the previous embodiments, the diaphragm pump 60 is manually compressible to expel the liquid contained in the receptacle 38 and biased to return to an initial unbiased position.

Figure 21:
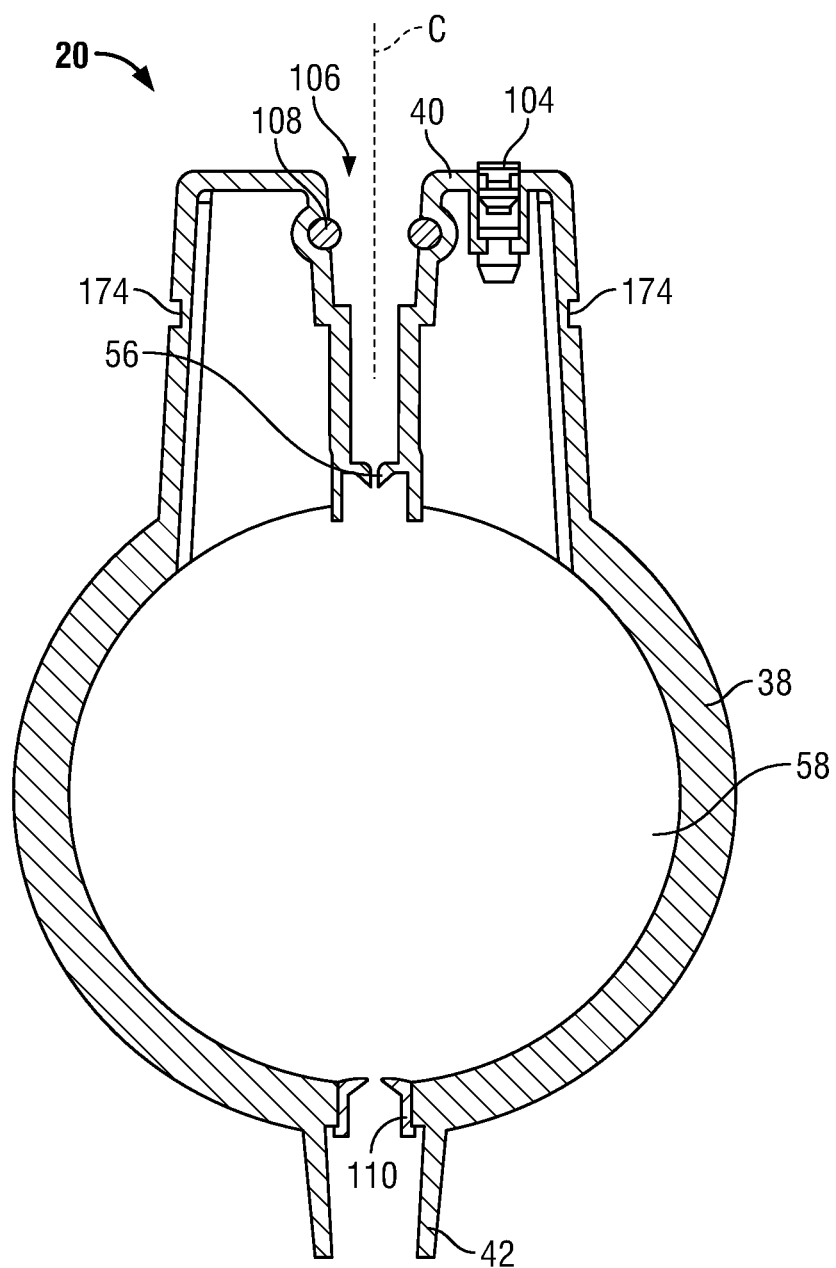
FIG. 21 shows a cross-sectional front view of the personal dispenser of FIG. 20.

The internal structure of the personal dispenser 20 is best shown in FIG. 21. The inlet port 40 defines a coupling channel 106 that extends along a coupling axis C. The coupling channel 106 is configured to receive the outlet tube 100 therein to couple the personal dispenser 20 and the dispenser outlet 18. An O-ring 108 is disposed coaxially within the coupling channel 106, and is arranged to engage with the annular groove 102 of the outlet tube 100 in a snap fit when the outlet tube 100 is received within the coupling channel 106. The engagement of the O-ring 108 with the annular groove 102 provides a preselected degree of resistance against the removal of the outlet tube 100 from the coupling channel 106. The degree of resistance is selected to prevent unintentional uncoupling of the personal dispenser 20 from the dispenser outlet 18, while permitting the personal dispenser 20 to be coupled and uncoupled when so desired.

The external laterally extending lateral channels 174 on personal dispenser 20 are configured to engage in a snap fit with the lateral protrusions 168 on the actuator plate 160, to provide further resistance against unintentional uncoupling of the personal dispenser 20. In particular, the engagement of the lateral channels 174 with the lateral protrusions 168 ensures that the personal dispenser 20 moves up and down with the actuator plate 160 when the manual actuator 22 is pressed, so as to remain coupled to the dispenser outlet 18.

The receptacle 38 is preferably formed from molded plastic, and defines an internal cavity 58 within which the liquid received from the inlet port 40 accumulates. The outlet port 42 is situated at the bottom of the receptacle 38, and includes a one-way outlet valve 110 configured to discharge fluid from the receptacle 38 only when a pressure differential across the outlet port 42 exceeds a preselected threshold.

To couple the personal dispenser 20 to the dispenser outlet 18, the outlet tube 100 is aligned with the coupling channel 106, such that the insertion axis I and the coupling axis C are coaxial, and the outlet tube 100 is inserted into the coupling channel 106. With the personal dispenser 20 coupled to the dispenser outlet 18, by manually pressing the manual actuator 22, the pump assembly 16 is activated to dispense the liquid from the reservoir 12 out through the outlet tube 100 and into the inlet port 40. The liquid then flows down into the internal cavity 58 of the receptacle 38, and begins accumulating therein.

As the liquid accumulates in the receptacle 38, the air displaced thereby is expelled through the pressure relief valve 104. This prevents the pressure within the internal cavity 58 from increasing to above the threshold pressure for the outlet valve 110, and so the outlet valve 110 does not open. Once the level of the liquid within the receptacle 38 reaches the height of the pressure relief valve 104, the pressure relief valve 104 closes and the pressure within the receptacle 38 may then rise to above the threshold pressure for the outlet valve 110 with liquid to be discharged out the outlet valve 110. The function of the pressure relief valve 104 may be achieved, for example, using a float that raises with the liquid to seal the pressure relief valve 104 when the level of the liquid within the receptacle 38 reaches the height of the pressure relief valve 104.

The personal dispenser 20 may be uncoupled from the dispenser outlet 18 once the desired volume of liquid has accumulated therein for remote use, or the personal dispenser 20 may be left coupled to the dispenser outlet 18. As in the previous embodiments, the construction of the liquid dispenser 10 advantageously permits the liquid to be discharged while the personal dispenser 20 remains coupled to the dispenser outlet 18. In particular, once the level of the liquid within the internal cavity 58 has reached the height of the pressure relief valve 104, the internal cavity 58 may be pressurized to create a pressure differential across the outlet port 42 that exceeds the preselected threshold, and thereby open the discharge valve 110 to dispense the liquid. As in the previous embodiments, the internal cavity 58 may be pressurized by introducing further liquid into the receptacle 38 through activation of the pump assembly 16, or by manual compression of the diaphragm pump 60.

The personal dispenser 20 can be easily uncoupled from the dispenser outlet 18 when desired, to provide a mobile supply of the liquid. As in the previous embodiments, the liquid is discharged from the personal dispenser 20 by manually compressing the diaphragm pump 60. Preferably, the pressure relief valve 104 is configured to remain closed while the personal dispenser 20 is uncoupled from the dispenser outlet 18.

As in the previous embodiments, the pump assembly 16 remains operable to dispense the liquid directly from the dispenser outlet 18 as onto a user's hand when the personal dispenser 20 is removed from the dispenser outlet 18.

When the supply of liquid within the reservoir 12 is depleted, the front cover 13 of the housing 14 can be hinged open to provide access to the replaceable cartridge 94 therein. The replaceable cartridge 94 can then easily be removed from the housing 14, and replaced with a new replaceable cartridge 94.

The invention is not limited to the preferred embodiments described herein. A person skilled in the art will appreciate that there are many possible variations and modifications that fall within the scope of the invention.

For instance, while the invention has been described in the preferred embodiments as for dispensing hand cleaners, the invention could also be applied to devices for dispensing other types of liquids such as hand cream, sunscreen, beverages, and other liquified cleaners, soaps and waxes. For example, in one alternate embodiment, it is envisioned that the invention could be applied to a device for dispensing car wax and/or polish in an auto body shop, to provide workers with portable refillable dispensers for small touch-ups.

While certain specific mechanisms for coupling and uncoupling the personal dispenser 20 and the dispenser outlet 18 have been described, it is to be appreciated that there may be many other suitable coupling mechanisms such as magnetic attachments, hook and loop fasteners, or elastic clips that fall within the scope of the invention. Furthermore, the coupling mechanisms that have been described with respect to one or more of the embodiments could optionally be used with the other embodiments, if desired. For example, the generally arcuate track 30 described with reference to the first embodiment shown in FIGS. 1 to 13 could, optionally, be used in a master dispenser 10 similar to the third embodiment shown in FIGS. 16 to 22. In particular, the actuator plate 160 could incorporate a generally arcuate track 30 for securely mounting the personal dispenser 20, and the personal dispenser 20 could be provided with a corresponding generally arcuate docking seat 44.

It is to be appreciated that the coupling mechanism could be configured to attach the personal dispenser 20 to any suitable part of the master dispenser 10 including, for example, the reservoir 12, the housing 14, the dispenser outlet 18, or the pump assembly 16, so long as the personal dispenser 20 is functionally linked to the master dispenser 10 in a way that allows liquid discharged from the master dispenser 10 to be received by the personal dispenser 20.

While the personal dispenser 20 has been described in some embodiments as optionally incorporating a transparent or semi-transparent diaphragm pump 60 for the purpose of visualizing the level of liquid therein, there may be many other suitable ways to determine the level of the liquid. For example, the personal dispenser 20 may incorporate a coloured float that rises with the level of the liquid. Alternatively, a transparent panel or chamber could be provided on the personal dispenser 20 through which the liquid is visible once it reaches a certain level.

While the preferred embodiments have described the receptacle 38 as incorporating a diaphragm pump 60 for the purpose of selectively discharging the liquid from the receptacle 38, it is to be understood that there are many alternative mechanisms that could be used. For example, the entire receptacle 38 could be formed from a flexible material such that the liquid is dischargeable by squeezing any part of the receptacle 38. The personal dispenser 20 could also incorporate other pump structures, such as an electric pump. Preferably, the personal dispenser 20 is configured to discharge between 1 ml and 5 ml of the liquid with each compression of the diaphragm pump 60, although any other desired discharge volume could be selected.

The liquid dispenser 10 may incorporate any suitable device for instructing the central processing unit 86 to activate the pump assembly 16, including but not limited to a button, a touchscreen, a wireless communication device, a microphone, a motion sensor, a radar sensor, a light sensor, an infrared sensor, or a camera.

In the first embodiment of FIGS. 1 to 13, three different configurations for the personal dispenser 20 are shown in which, while the personal dispenser 20 is coupled to the dispenser outlet 18 and full, operation of the master dispenser 10 discharges liquid through the personal dispenser 20 and onto a user's hand. This is preferred but not necessary. For example, each personal dispenser 20 could be configured such that while coupled to the dispenser outlet 18, once the personal dispenser 20 is filled with liquid, further operation of the pump assembly 16 will not discharge liquid out the personal dispenser 20. For example, the further operation of the pump assembly 16 after the personal dispenser 20 is full will not discharge any further liquid. The personal dispenser 20 must be removed from the dispenser outlet 18 for liquid to be discharged onto a user's hand from the dispenser outlet 18, or the personal dispenser 20 manually operated to discharge fluid from its outlet port 42 while the personal dispenser 20 is coupled to the dispenser outlet 18. In any case, preferably an arrangement is provided for detecting the amount of liquid discharged from the master dispenser 10 whether directly onto a user's hand or into a personal dispenser 20.

Reference is made to FIGS. 23 to 26 which show a liquid master dispenser 10 in accordance with a fourth preferred embodiment of the invention. The fourth embodiment of FIGS. 23 to 26 is identical to the first embodiment of FIGS. 1 to 11, with the exceptions that (a) a two way valve mechanism 200 including a refill tube 202 are provided on the spout tube 134, and (b) an opening 204 is provided through the shroud 19.

Figure 23:
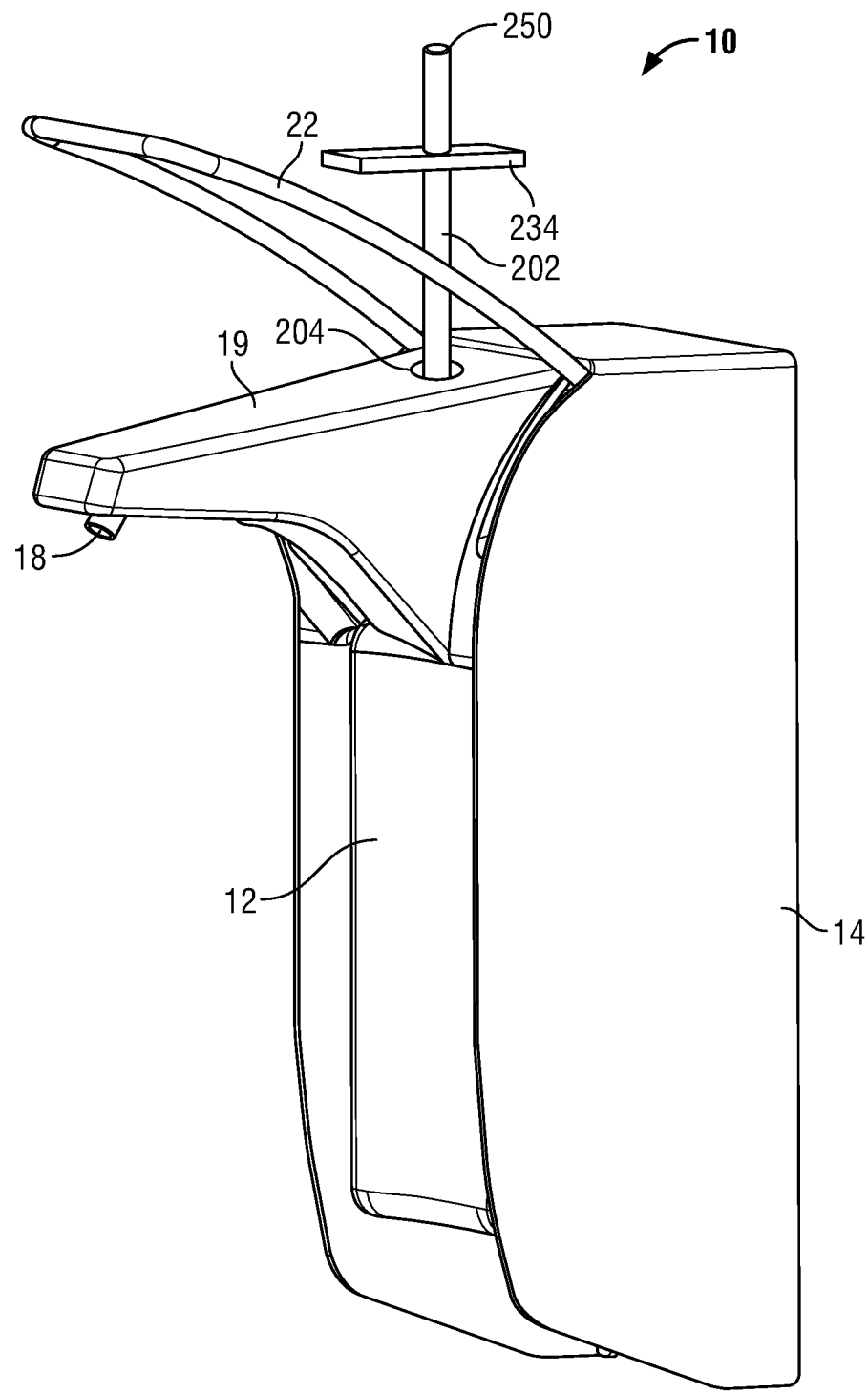
FIG. 23 shows a perspective view of a liquid master dispenser in accordance with a fourth preferred embodiment of the invention.
Figure 24:
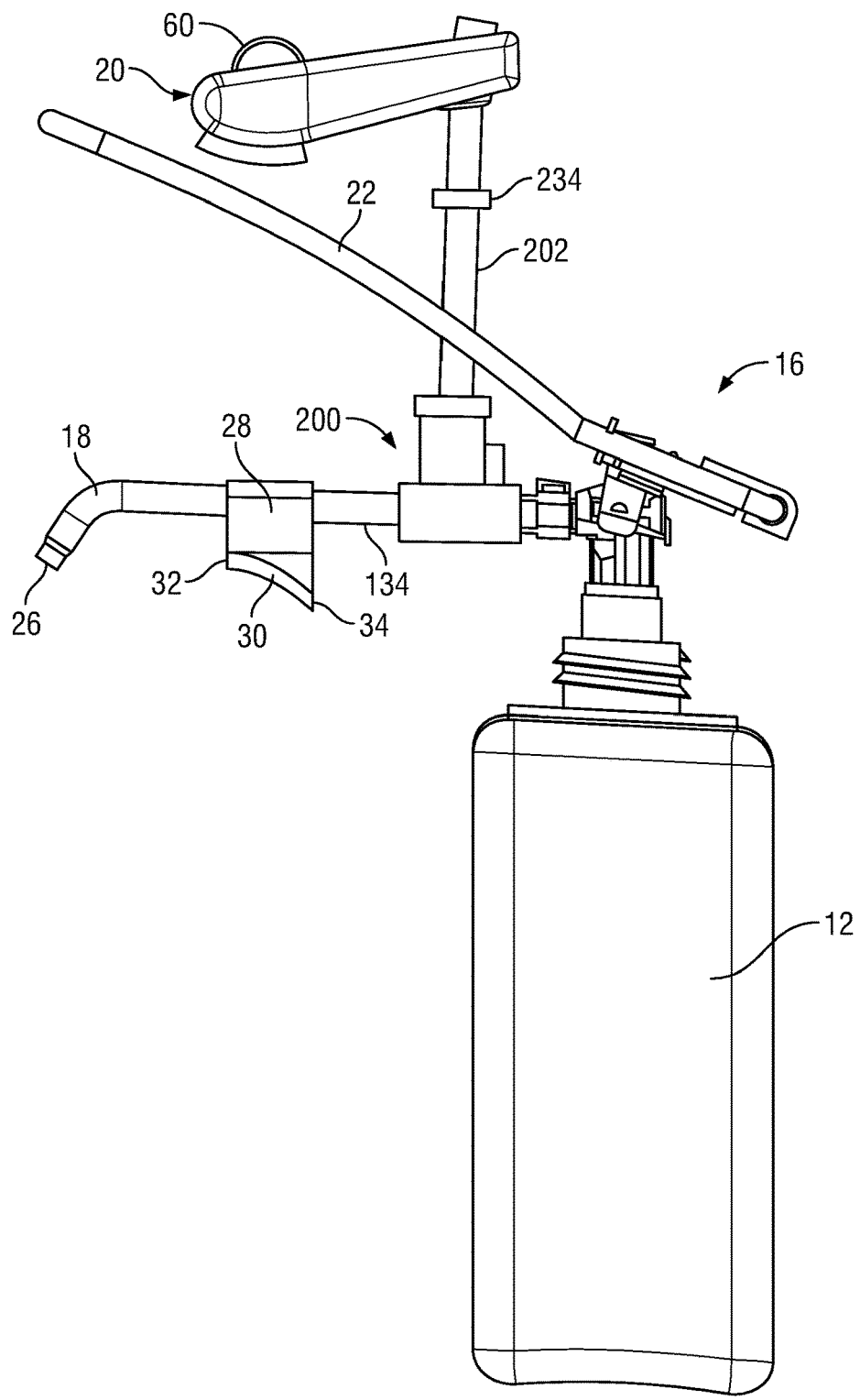
FIG. 24 shows a pictorial side view of the liquid master dispenser of FIG. 23 with the housing removed, and a personal dispenser in a coupled state to a refill tube.
Figure 25:
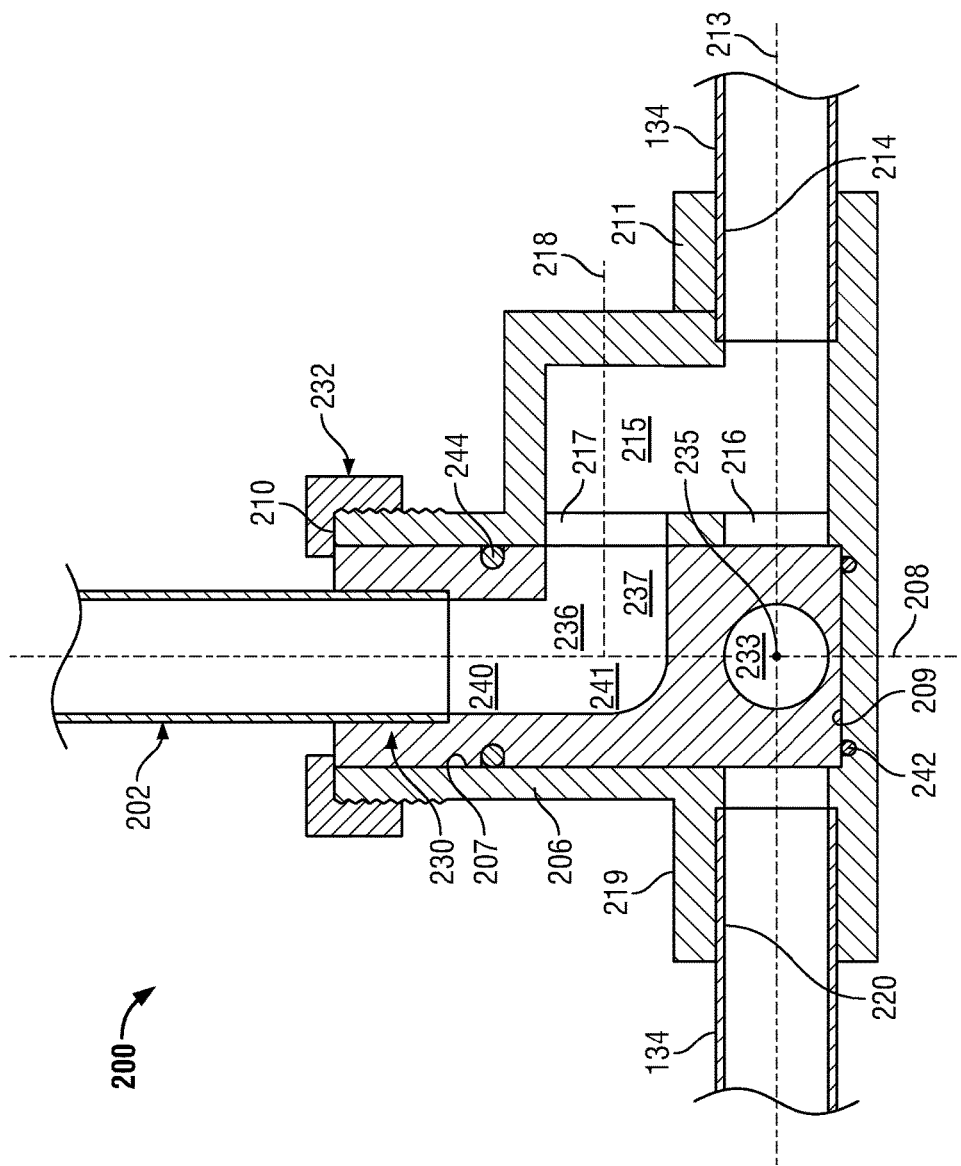
FIG. 25 shows an enlarged vertical cross-sectional view of the valve assembly in FIG. 24 in a diversion condition as in FIG. 24 to direct fluid via the refill tube to the personal dispenser.
Figure 26:
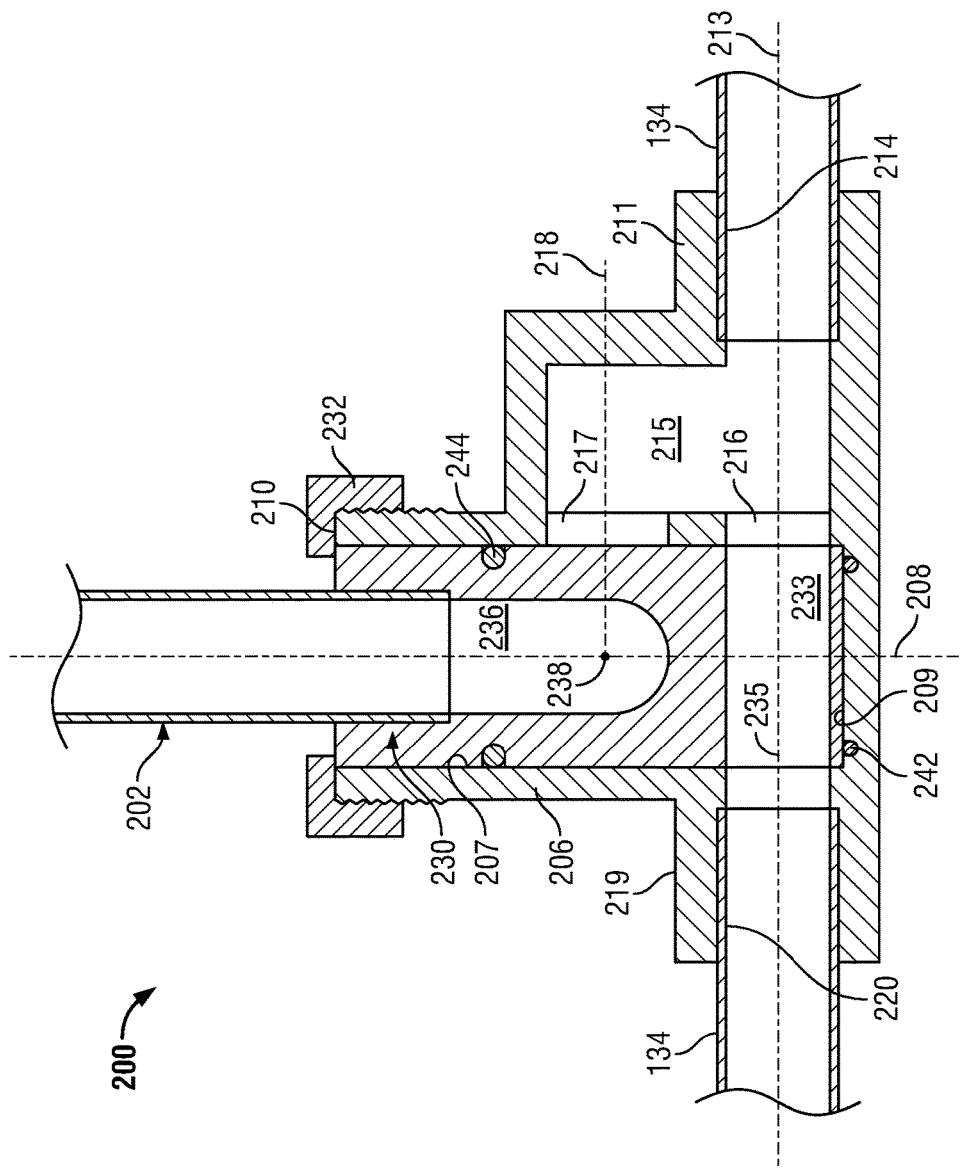
FIG. 26 shows the enlarged vertical cross-sectional view of the valve assembly as in FIG. 25 but in a flow through condition as in FIG. 23 to direct fluid to a discharge outlet.

The valve mechanism 200 is movable between a flow through condition as in FIGS. 23 and 26 in which fluid from the pump assembly 16 is directed merely to the discharge outlet 18, and a diversion condition as in FIGS. 24 and 25 in which fluid from the pump assembly 16 is directed merely to the refill tube 202.

Reference is made to FIG. 25 which shows a vertical cross-section through the valve mechanism 200. The valve mechanism 200 includes a valve housing 206, a valve member 230 and a cap 232.

The housing 206 defines a cylindrical bore 207 disposed about a vertical axis 208. The bore 207 is closed at a lower end 209 and open at an upper end 210.

The valve housing 206 has a cylindrical inlet collar 211 disposed about a lower horizontal axis 213. The inlet collar 211 receives coaxially therein an inlet portion 214 of the spout tube 134 which receives fluid from the pump assembly 16. The inlet collar 211 opens into a diverter chamber 215 which has two cylindrical outlet ports. A lower outlet port 216 opens into the bore 207 and is coaxial about the lower horizontal axis 213. An upper outlet port 217 opens into the bore 207 and is coaxial about an upper horizontal axis 218 spaced above the lower horizontal axis 213. The housing 206 has a cylindrical lower outlet collar 219 which opens into the bore 207 diametrically across from the lower outlet port 216 and is coaxial about the lower horizontal axis 213. The lower outlet collar 219 securely receives therein an outer portion 220 of the spout tube 134 which extends to the discharge outlet 18.

The valve member 230 is cylindrical and sized to be coaxially received within the bore 207 and for relative rotation therein about the vertical axis 208 between a flow-through condition as seen in FIG. 26 and a diversion condition as seen in FIG. 25 by rotation of the valve member 230 90 degrees about the axis 208, the refill tube 202 is fixedly secured to the valve member 233 with the refill tube 202 coaxial about the vertical axis 208. As can be seen in FIG. 23, a handle member 234 is fixedly secured to the refill tube 202 for rotation therewith and for movement between a position corresponding to the flow-through condition as shown in FIG. 23 in which the handle extends forwardly and rearwardly and a position corresponding to the diversion condition as shown in FIG. 24 in which the handle extends side to side.

The valve member 230 has two flow passageways therethrough. A cylindrical lower passageway 233 extends through the valve member 230 along a horizontal axis 235. An L-shaped diverter passageway 236 extends through the valve member 230 with a horizontal portion 237 about a horizontal axis 238 and a vertical portion 240 coaxial about the axis 208, and an arcuate portion 241 which joins the horizontal portion 237 and the vertical portion 240.

The refill tube 202 is fixedly coaxially received within an upper end of the vertical portion 240.

As seen in FIG. 25, corresponding to the diversion condition, the diverter passageway 236 is open to the diverter chamber 215 via the upper outlet port 217 such that fluid flow from the inlet portion 214 of the spout tube 134 passes through the diverter chamber 215 into the diverter passageway 236 and to the refill tube 202. In the position as seen in FIG. 25, the through passageway 233 is disposed to extend perpendicular to the lower horizontal axis 218 and thus fluid flow through the bore 207 from the diverter chamber 25 to the lower outlet collar 219 is prevented.

Referring to FIG. 26, which represents the flow-through condition, the flow-through passageway 233 is disposed coaxially with the lower horizontal axis 213 and fluid from the pump assembly 16 may flow from the inlet portion 214 of the spout tube 134 through the diverter chamber 215 through the lower outlet port 216 into the bore 207 through the flow-through passageway 233 in the valve member 230 and out the outlet collar 219 to the outer portion 220 of the spout tube 134 and hence to the discharge outlet 18. Flow from the diverter chamber 215 to the refill tube 202 is blocked since the valve member 230 blocks the upper outlet port 217.

The valve member 230 is axially retained within the bore 207 by a threaded cap 232 which engages an axial shoulder on the valve member 230 urging a lower end of the valve member 230 downwardly onto a first sealing ring 242 disposed between the lower end of the valve member 230 and the lower end 209 of the bore 207 coaxially about the vertical axis 208. A second sealing ring 244 is coaxially about the vertical axis 208 providing a seal between a cylindrical inner surface of the bore 207 and a cylindrical outer surface of the valve member 230.

As can be seen in FIG. 23, the refill tube 202 extends upwardly through the shroud 19 through the opening 204. The opening 204 permits the refill tube 202 to move vertically with the spout tube 134 relative the shroud 19 during an operation of the pump assembly 16 to dispense fluid.

The refill tube 202 has a refill outlet 250 preferably having a configuration similar to the outlet end 26 of the discharge outlet 18 such that a personal dispenser 20 of the type illustrated in FIG. 5 may be coupled to the refill outlet 250 as illustrated in FIG. 24. With the valve mechanism 200 in the diverted condition as seen in FIG. 24 or FIG. 26 with operation of the pump assembly 16, fluid is discharged into the personal dispenser 20 to fill the same by manual operation of the actuator 22. When the personal dispenser 20 becomes filled with liquid as may be seen, for example, by a person using the dispenser 10 seeing the fluid as filling the transparent diaphragm pump 60 in the personal dispenser 20, manual operation of the pump assembly 16 is ceased, the handle 234 may be rotated 90 degrees from the diversion condition to the flow-through condition as shown in FIG. 23 and the personal dispenser 20 removed from the refill tube 202 for remote use.

FIG. 24 shows a mounting dock 28 coupled to the spout tube 134. With a mounting dock 28 coupled to the spout tube 134, then a personal dispenser 20 may also be coupled to the discharge outlet 18 as with the first embodiment of FIG. 1. However, in the fourth embodiment, the provision of a mounting dock 28 on the spout tube 134 is not necessary.

In the fourth embodiment shown in FIG. 24, a personal dispenser 20 is shown as coupled to the refill tube 202 with the personal dispenser 20 having the same configuration as in FIG. 5. This, of course, is not necessary and a personal dispenser with a different configuration may be provided adapted for removable coupling to the refill tube 202 for filling. For example, a different personal dispenser might be arranged so as to extend more vertically upwardly from the refill tube 202 effectively coaxially about the refill tube 202 as for balancing of the personal dispenser upon the refill tube 202. The personal dispenser may be configured such that when the personal dispenser is full of the liquid, the flow of fluid out of the outlet of the personal dispenser 20 is prevented.

In accordance with the fourth embodiment of the invention, the discharge outlet 28 may include a spray nozzle in its outlet 26 of a type, for example, to spray small droplets or a mist of the liquid being dispensed as can be accommodated by providing restrictions or rotating members with the outlet 26. Similarly, the personal dispenser 20 may have, in addition to a one-way outlet valve 66, a discharge outlet which also provides such a spray nozzle to spray small droplets or a mist of the liquid when the personal dispenser such is manually operated. In the context of the arrangement in FIG. 24, insofar as the dispenser outlet 26 has a spray nozzle, it may be advantageous to refill the personal dispenser 20 from the refill nozzle rather than through the outlet 26.

The master dispenser 10 can incorporate additional mechanisms for discharging the liquid from the reservoir 12. For example, as in the fourth embodiment of FIGS. 23 to 26, liquid discharged by a single pump assembly 16 is delivered by suitable valving arrangements such as the two-way valve assembly 200 either to the dispenser outlet 18 or to a separate and distinct refill outlet 250 as on a refill tube 202 outlet, with a personal dispenser 20 to be removably attached to the refill outlet. The valving arrangements could have many alternate configurations to the two-way arrangement like that of the fourth embodiment which permit a manual selection as to which one of a number of outlets the liquid is to be dispensed, for example, through rotating or sliding a movable valve member to selectively choose which outlet receives fluid from an internal conduit 120 of the pump assembly 16. More than one such refill outlet may be provided. More than one discharge outlet may be provided.

A first alternate arrangement can be such that: (a) while a personal dispenser 20 is coupled to a refill outlet, fluid does not flow to the dispenser outlet 18 and fluid only flows out the refill outlet into the personal dispenser 20 until the personal dispenser 20 is full; (b) the liquid does not flow out of the personal dispenser 20 until the personal dispenser 20 is uncoupled from the refill outlet; (c) while the personal dispenser is not coupled to the refill outlet fluid merely flows to the discharge dispenser outlet 18 and onto a user's hand.

A second alternate arrangement can be such that: (a) while a personal dispenser 20 is coupled to the refill outlet, fluid does not flow to the dispenser outlet 18 and fluid only flows out the refill outlet into the personal dispenser 20 until the personal dispenser 20 is full; (b) the liquid does not flow out of the personal dispenser 20 until the personal dispenser 20 is uncoupled from the refill outlet; (c) while the personal dispenser 20 is coupled to the refill outlet and the personal dispenser 20 is full of liquid, liquid flows to the dispenser outlet 18 and onto a user's hand; and (d) while the personal dispenser 20 is not coupled to the refill outlet, fluid merely flows to the dispenser outlet 18 and onto a user's hand.

The master dispenser 10 could be provided with two different pump assemblies 16 with one to have liquid it discharges flow to the dispenser outlet 18 and onto a user's hand, and a second pump assembly to have the liquid it discharges flow to a refill outlet separate from the dispenser outlet 18, and adapted to have personal dispensers 20 removably coupled thereto for merely refilling. The pump assemblies 16 could be activated manually or driven by electric motors 142. Selection of the pump assembly 16 activated will determine where the liquid is delivered. Suitable selection of which pump assembly 16 may be activated can take into account whether or not a personal dispenser 20 is coupled to a refill outlet.

Any refill outlet which is separate from the dispenser outlet 18 may share some or all of their liquid pumping and delivery components with the dispenser outlet 18, or may be formed as entirely separate structures which do not share some or all of their liquid pumping and delivery components with the dispenser outlet 18. Preferably, all liquid dispensed is from the same reservoir 12. Preferably, however, an arrangement is provided for detecting the amount of liquid discharged from the master dispenser 10 whether directly onto a user's hand or into a personal dispenser 20.

Any suitable sensor arrangement for detecting the amount of liquid discharged from the master dispenser 10 could be used including, for example, ones that (i) detect a volume or a mass of the liquid contained in the reservoir 12; (ii) detect a flow of the liquid through the dispenser outlet 18; (iii) detect a flow of the liquid through the refill outlet; (iv) detect the activation of the discharge mechanism; or (v) detect the activation of the filling mechanism.

Figure 27:
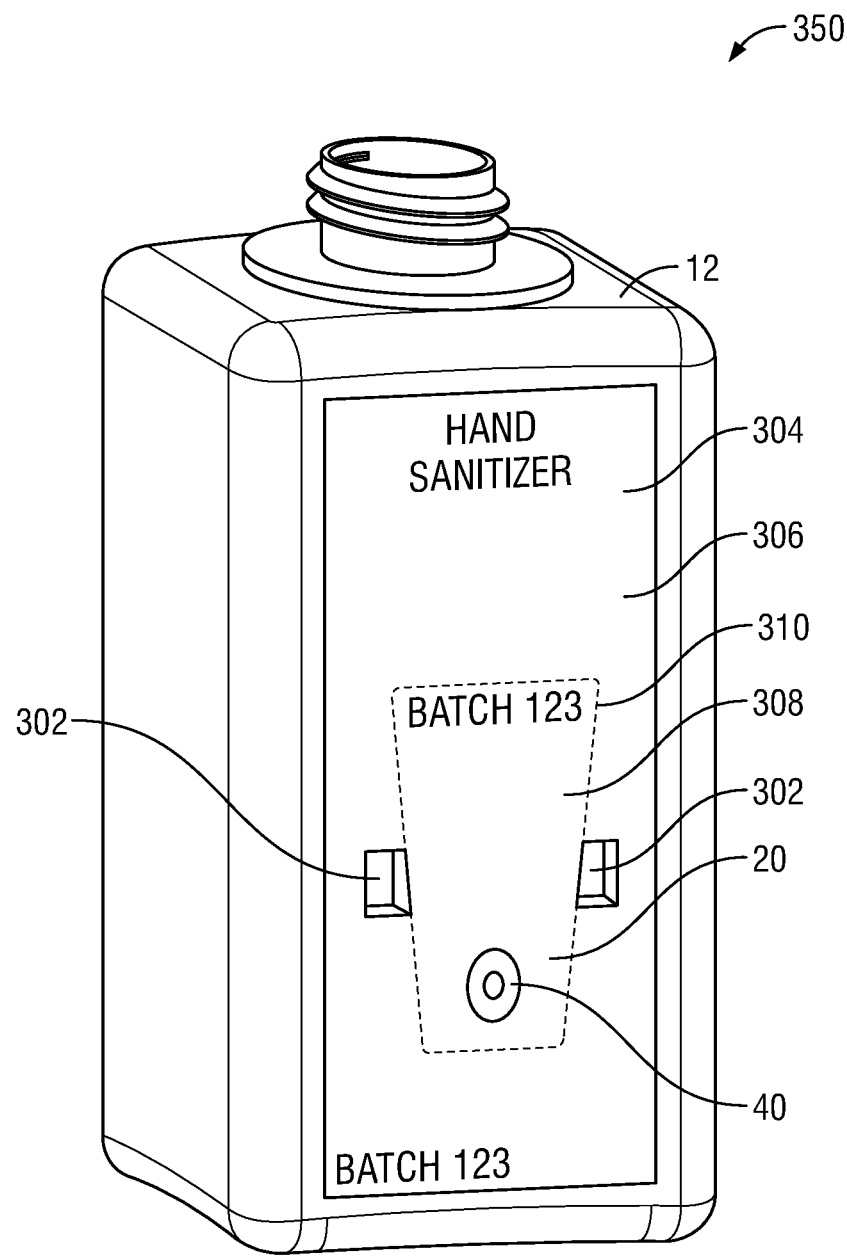
FIG. 27 shows a perspective view of a reservoir cartridge, comprising a reservoir with a personal dispenser held in a cavity thereof, in accordance with a fifth preferred embodiment of the invention.
Figure 28:
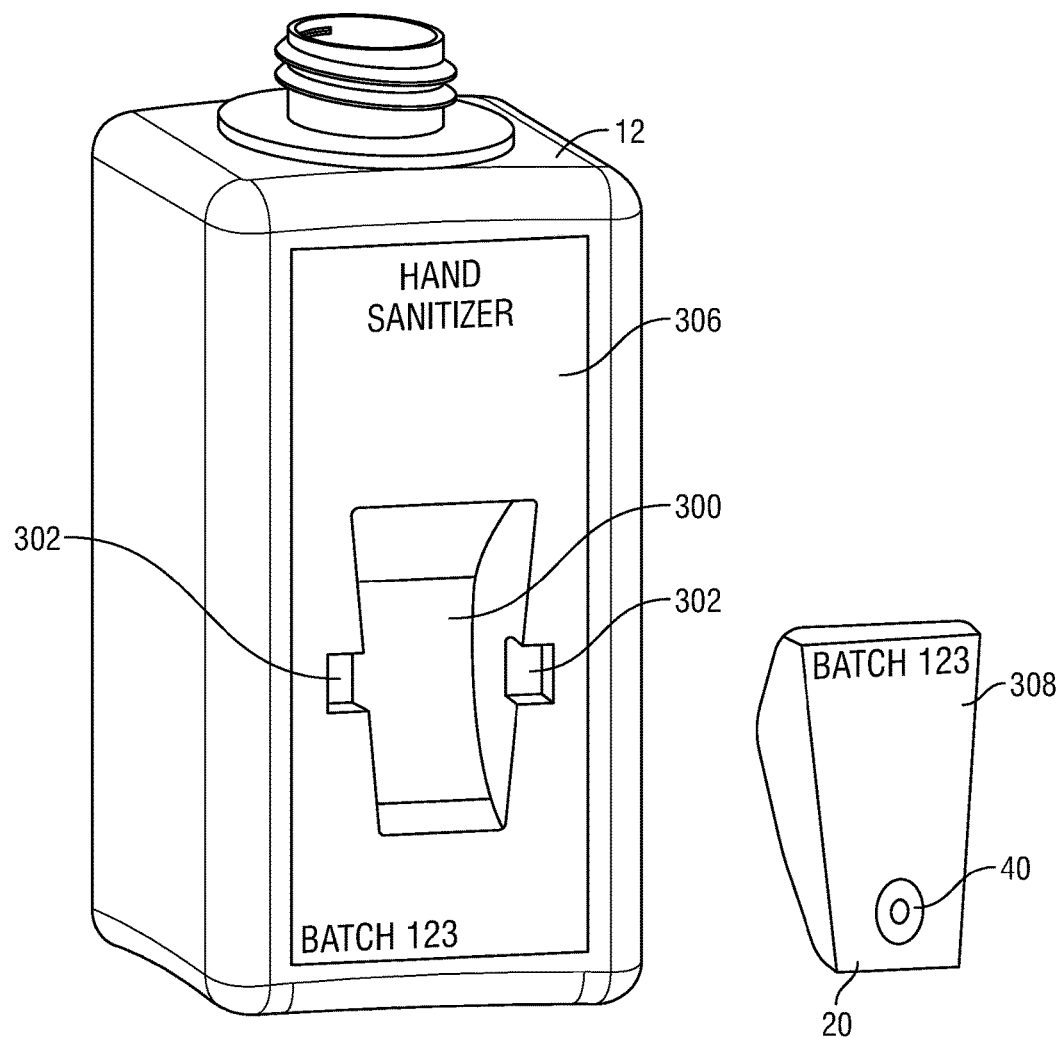
FIG. 28 shows a perspective view of the reservoir and personal dispenser of FIG. 27, with the personal dispenser removed from the cavity.

FIGS. 27 and 28 show a reservoir cartridge 350 in accordance with a fifth preferred embodiment of the invention, wherein like reference numerals are used to denote like components. The reservoir cartridge 350 comprises a reservoir 12 and a personal dispenser 20, which are configured to be used with a liquid master dispenser 10 in a similar manner as in the embodiments described above. What distinguishes the fifth embodiment of the invention from the previously described embodiments, is that the reservoir 12 and the personal dispenser 20 are packaged together in an initial bundled configuration for distribution. In particular, the reservoir 12 has a cavity 300 that is shaped to receive the personal dispenser 20 therein. The personal dispenser 20 is configured so as not to protrude from the cavity 300, with the face of the personal dispenser 20 approximately flush with the face of the reservoir 12. This gives the reservoir cartridge 350 a relatively flat and smooth outer profile, which permits the cartridge 350 to be efficiently packaged together for shipment to customers, such as stacked with other cartridges 350 in a box. The reservoir 12 has small indentations 302 on either side of the cavity 300, to allow customers to grasp the personal dispenser 20 to remove it from the cavity 300 for use.

The reservoir 12 and personal dispenser 20 are provided with a common label 304 having a first part 306 that is permanently affixed to the outer surface of the reservoir 12, and a second part 308 that is permanently affixed to the outer surface of the personal dispenser 20. The label 304 has a perforated line 310 at the junction between the first part 306 and the second part 308, which allows a user to cleanly tear the label 304 along the perforated line 310 when removing the personal dispenser 20 from the cavity 300. The common label 304 helps to hold the personal dispenser 20 within the cavity 300 during packaging and shipment, and also allows the reservoir 12 and personal dispenser 20 to be marked with required information such as batch numbers and the like. The label 304 also helps customers to detect if the cartridge 350 may have been tampered with during shipment. In particular, by inspecting the cartridge 350 to see if the label 304 has been torn, a customer can detect if the personal dispenser 20 has been removed from the cavity 300.

Figure 29:
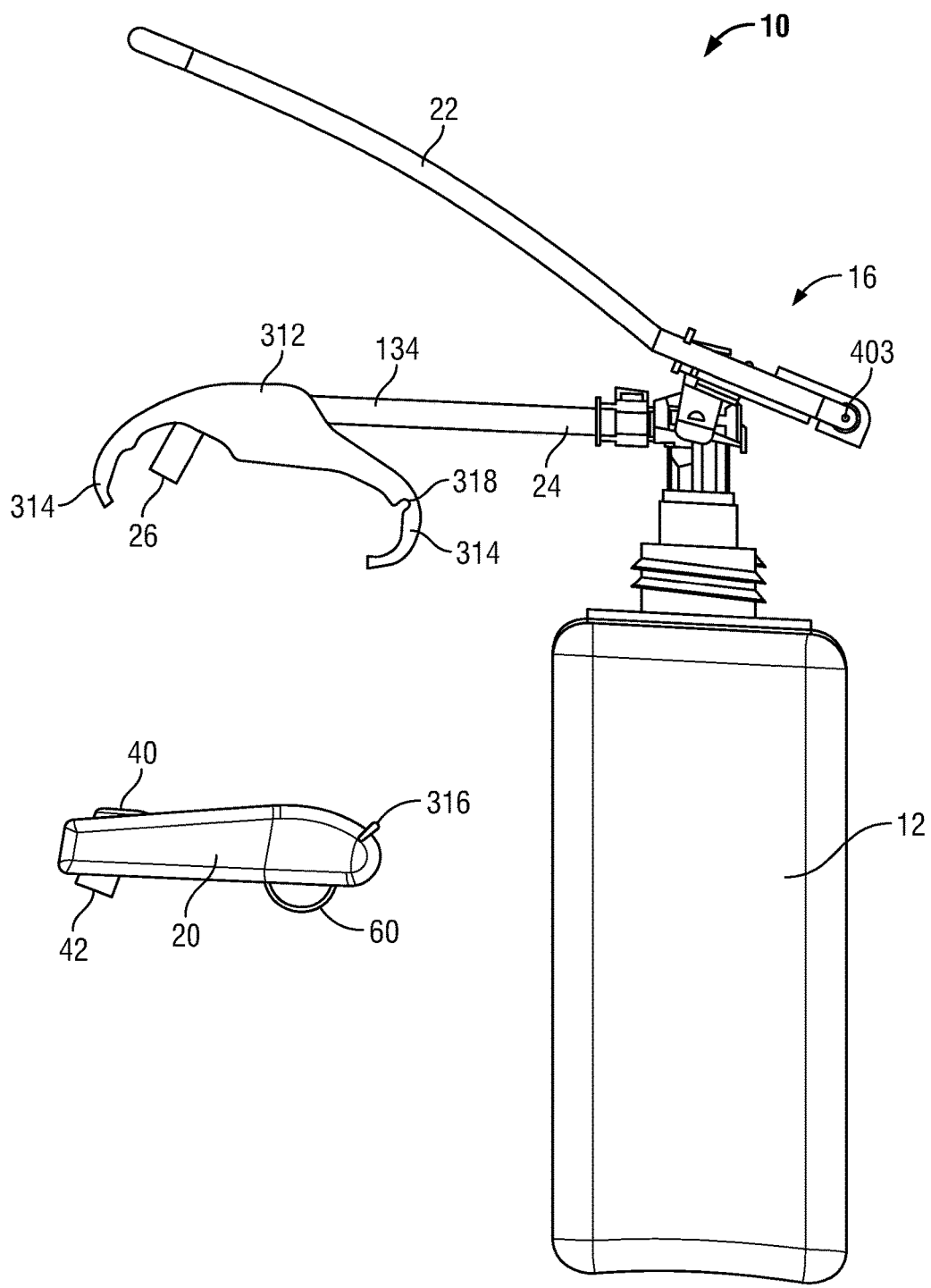
FIG. 29 shows a side view of a liquid master dispenser in accordance with a sixth preferred embodiment of the invention, with a personal dispenser in an uncoupled state.
Figure 30:
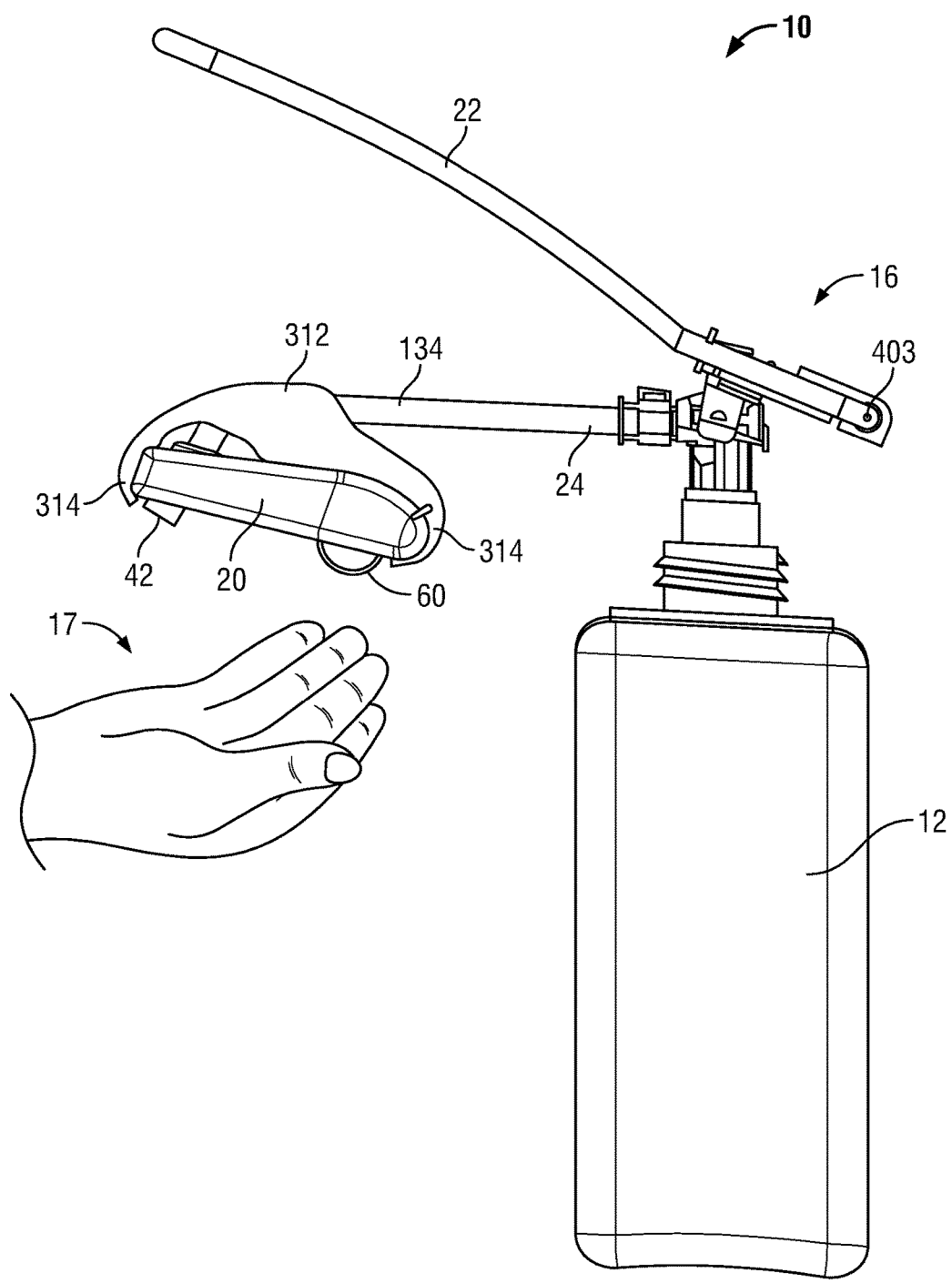
FIG. 30 shows a side view of the liquid master dispenser of FIG. 29, with the personal dispenser coupled to a spout tube of the master dispenser.

Reference is now made to FIGS. 29 and 30, which show a liquid master dispenser 10 in accordance with a sixth preferred embodiment of the invention, wherein like reference numerals are used to denote like components. This embodiment of the invention is generally similar to the first embodiment of the invention described above, and operates in a similar manner. The features of the sixth embodiment of the invention which differ from those of the first embodiment are described below.

The sixth embodiment of the invention uses a cradle type dock 312 for coupling the personal dispenser 20 to the spout tube 134 of the master dispenser 10, in place of the mounting dock 28 used in the first embodiment of the invention. The personal dispenser 20 is substantially the same as used in the first embodiment, with exception that the arcuate docking seat 44 is removed. The cradle type dock 312 has resiliently flexible arms 314 that, when in an unbiased state, define an inner profile that is complimentary to the outer profile of the personal dispenser 20. To couple the personal dispenser 20 to the dock 312, the arms 314 are manually pulled apart and the personal dispenser 20 is positioned therebetween, with the outlet end 26 of the spout tube 134 inserted into the inlet port 40 of the personal dispenser 20. The arms 314 are then released, allowing them to return to their unbiased state around the personal dispenser 20, holding the personal dispenser 20 in place. To uncouple the personal dispenser 20 from the dock 312, the arms 314 are pulled apart and the personal dispenser 20 is removed.

Preferably, the personal dispenser 20 and dock 312 incorporate lock-out features that prevent them from coupling with unapproved devices, such as devices made by other manufacturers. For example, as shown in FIGS. 29 and 30, the personal dispenser 20 can incorporate a rib 316 that fits into a complementary void 318 in the dock 312. When an approved personal dispenser 20 is used with the corresponding dock 312, the rib 316 and the void 318 are aligned so that docking is possible. However, if a user attempts to use an unauthorized personal dispenser 20 having a different shape, including ribs 316 that are not properly aligned with voids 318 in the dock 312, the lock-out features will prevent the dock 312 and the personal dispenser 20 from coupling. This prevents any impairment of performance that might otherwise occur if an unauthorized personal dispenser 20 was coupled to the master dispenser 10. It is to be appreciated that any desired configuration of lock-out features could be used, including, for example, any combination of one or more sets of ribs 316, voids 318, protrusions, cavities, and keyed structures located on the personal dispenser 20 and dock 312, or on other associated structures.

Reference is now made to FIGS. 31 to 37, which show a liquid master dispenser 10 in accordance with a seventh preferred embodiment of the invention, wherein like reference numerals are used to denote like components. The seventh embodiment of the invention corresponds identically to the first embodiment of the invention described above, with the exception that the personal dispenser 20 has a modified, airless construction. The mounting dock 28 also has an alternate construction for coupling with the modified personal dispenser 20.

Figure 31:
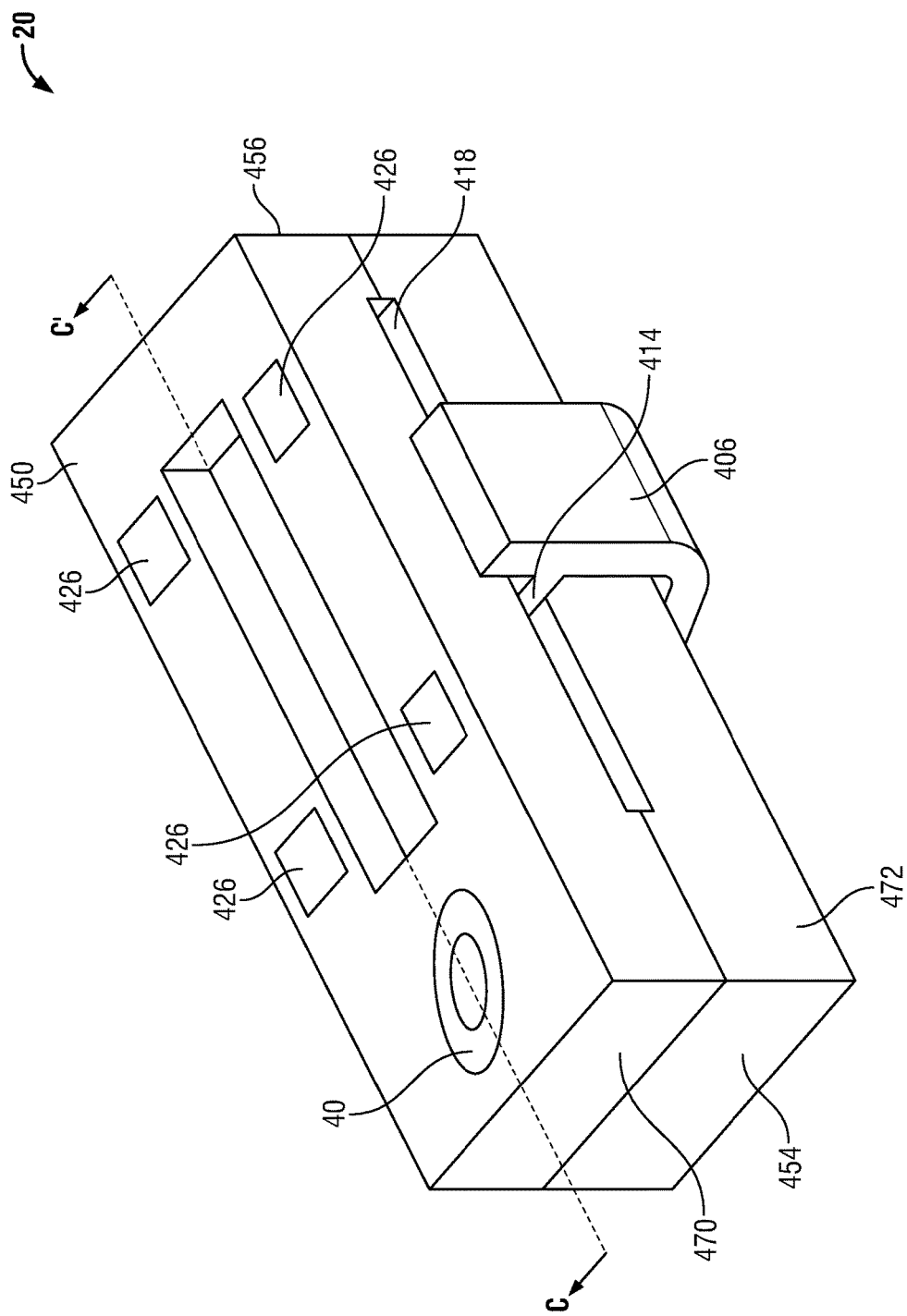
FIG. 31 shows a perspective view of a personal dispenser in accordance with a seventh preferred embodiment of the invention.
Figure 32:
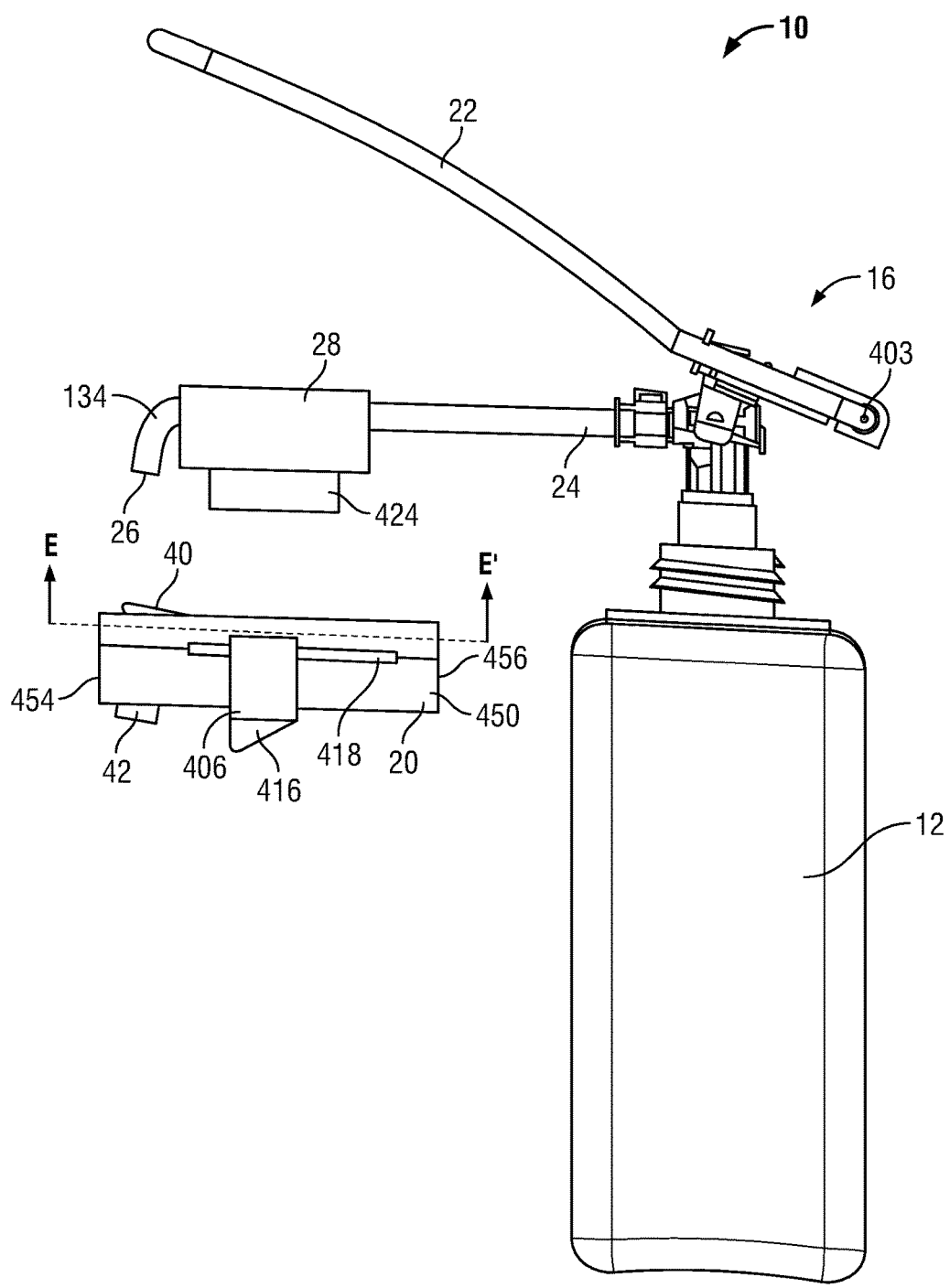
FIG. 32 shows a side view of a liquid master dispenser incorporating the personal dispenser of FIG. 31, with the personal dispenser in an uncoupled state.
Figure 33:
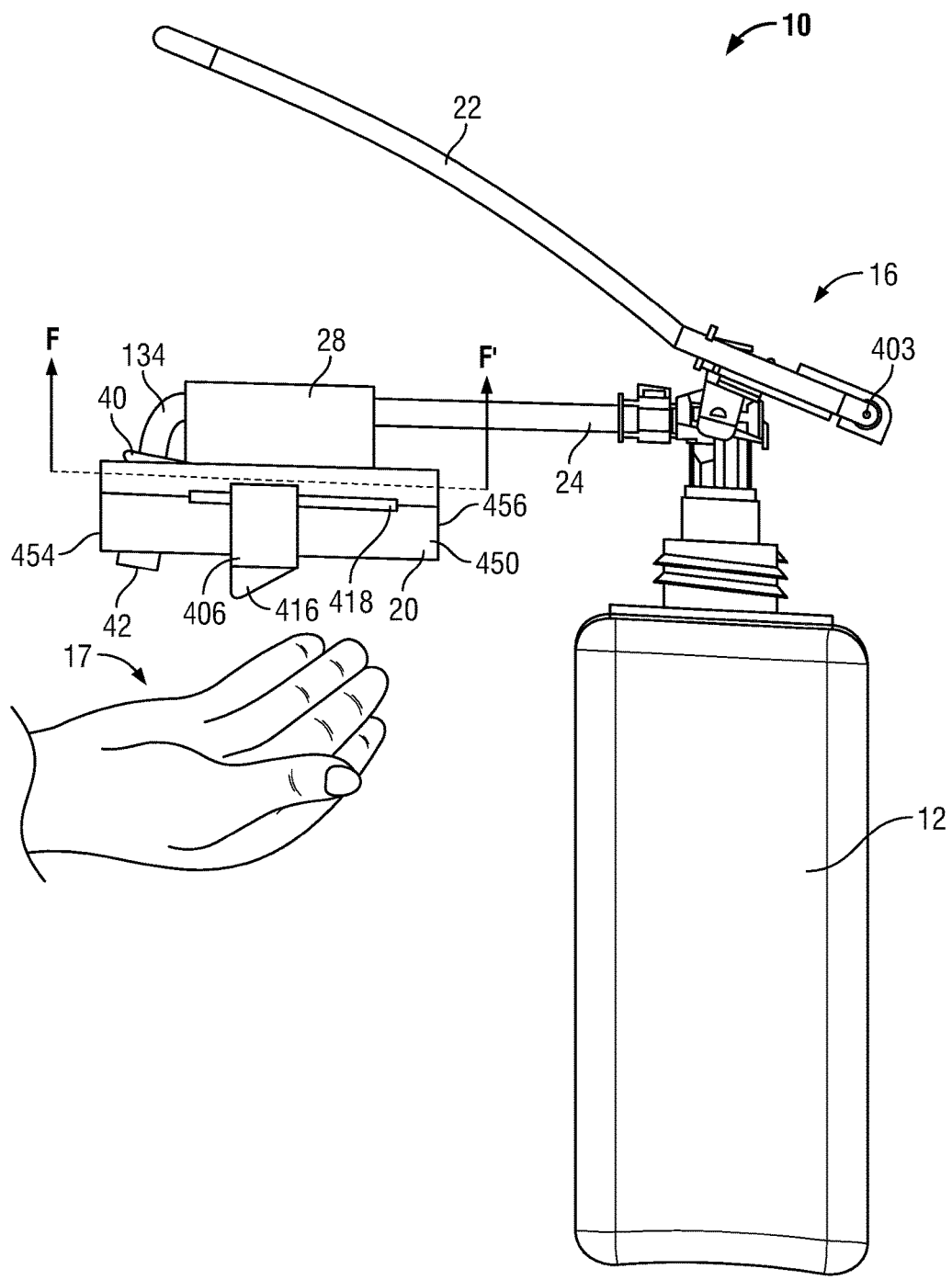
FIG. 33 shows a side view of the liquid master dispenser of FIG. 32, with the personal dispenser in a coupled state.
Figure 34:
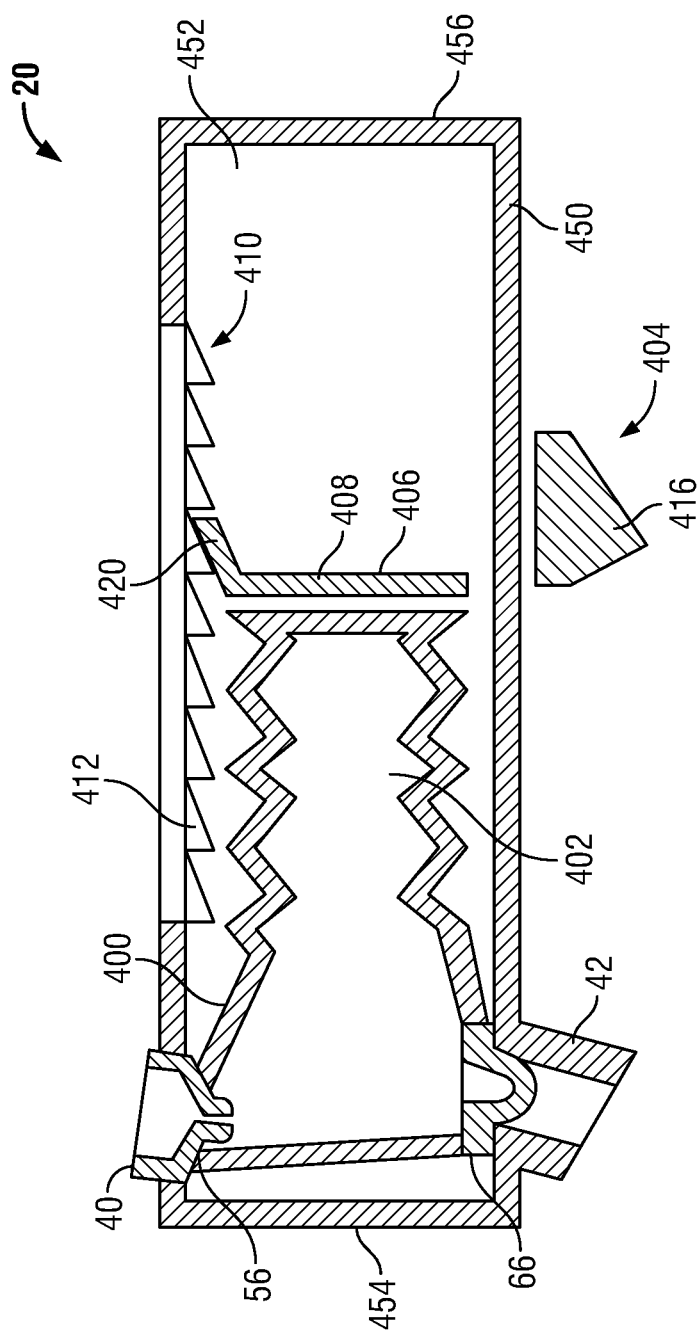
FIG. 34 shows a cross-sectional view of the personal dispenser of FIG. 31 along section line C-C'.

As shown in FIG. 31, the personal dispenser 20 has a rigid, generally rectangular outer housing 450. As best shown in FIG. 34, the housing 450 defines an internal cavity 452 that extends longitudinally between a first end 454 and a second end 456 of the housing 450. The inlet port 40 and the outlet port 42 are situated near the first end 454, and are spaced from the second end 456. A collapsible internal bellows or bag 400 is arranged within the internal cavity 452, and is attached in a liquid tight manner to the one-way inlet valve 56 of the inlet port 40 and the one-way outlet valve 66 of the outlet port 42. The bag 400 defines a liquid chamber 402 for containing liquid within the personal dispenser 20. The bag 400 expands and contracts longitudinally within the cavity 452 as liquid enters from the inlet port 40 or exits from the outlet port 42, such that the volume of the liquid chamber 402 varies depending on the amount of liquid contained therein.

The personal dispenser 20 incorporates a ratcheted plunger mechanism 404 for compressing the bag 400, to thereby expel the liquid contained in the bag 400 out through the outlet port 42. The ratcheted plunger mechanism 404 comprises a plunger body 406 with a flexible pawl 408 that engages with a rack 410 of teeth 412 arranged longitudinally on an internal upper surface of the housing 450. A connecting body 414 connects the flexible pawl 408, located within the housing 450, to an external push button 416. As best shown in FIG. 31, the connecting body 414 is slidably arranged within a side slot 418 of the housing 450. The plunger body 406 can be moved longitudinally toward the first end 454 of the housing 450 by manually pushing the push button 416 in that direction.

The flexible pawl 408 has an angled foot 420 that engages with the rack 410. As the plunger body 406 moves toward the first end 454 of the housing 450, the flexible nature of the pawl 408 permits the foot 420 to bend downwards, away from the rack 410, as it passes over the teeth 412. This permits the plunger body 406 to be moved freely toward the first end 454. In doing so, the plunger body 406 presses against the bag 400, causing it to compress. This increases the internal pressure of the liquid within the bag 400, and once a threshold pressure has been reached, forces the liquid through the one-way outlet valve 66 of the outlet port 42. The one-way inlet valve 56 prevents the liquid from discharging from the inlet port 40.

Preferably, the personal dispenser 20 is configured so that each step of the plunger body 406 along the rack 410 consistently discharges a known quantity of the liquid from the outlet port 42. For example, the personal dispenser 20 could be configured to discharge 0.5 ml of the liquid with each step of the plunger body 406 along the rack 410, such that a user is able to estimate the total amount of liquid that has been discharged from the personal dispenser 20 by counting the number of audible clicks that are heard as the plunger 406 is moved. The housing 450 could also be provided with markings that indicate the volume of liquid held within the bag 400 at each position of the push button 416.

Once the bag 400 has been fully compressed and the plunger body 406 is located near the first end 454 of the housing 450, the angle of the foot 420 against the teeth 412 of the rack 410 prevents the foot 420 from being moved back along the rack 410 toward the second end 456. This locks the plunger body 406 in place, preventing the bag 400 from expanding so long as the foot 420 remains engaged with the rack 410. To release the engagement of the foot 420 with the rack 410, and thereby unlock the plunger body 406, the personal dispenser 20 is docked to the mounting dock 28.

Figure 35:
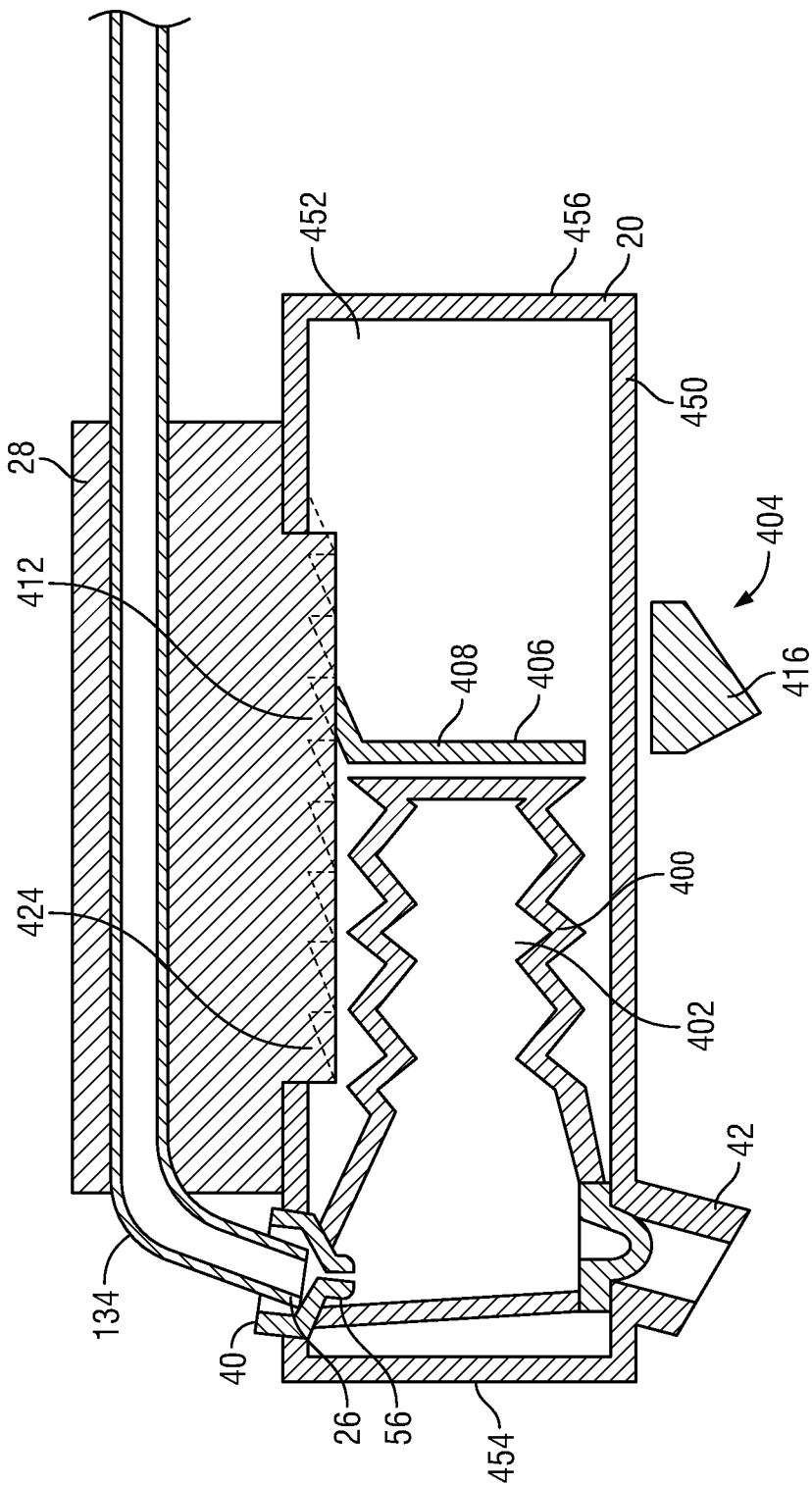
FIG. 35 shows a cross-sectional view of the personal dispenser of FIG. 31, which is the same view as shown in FIG. 34, but with the personal dispenser in a coupled state as in FIG. 33.
Figure 36:
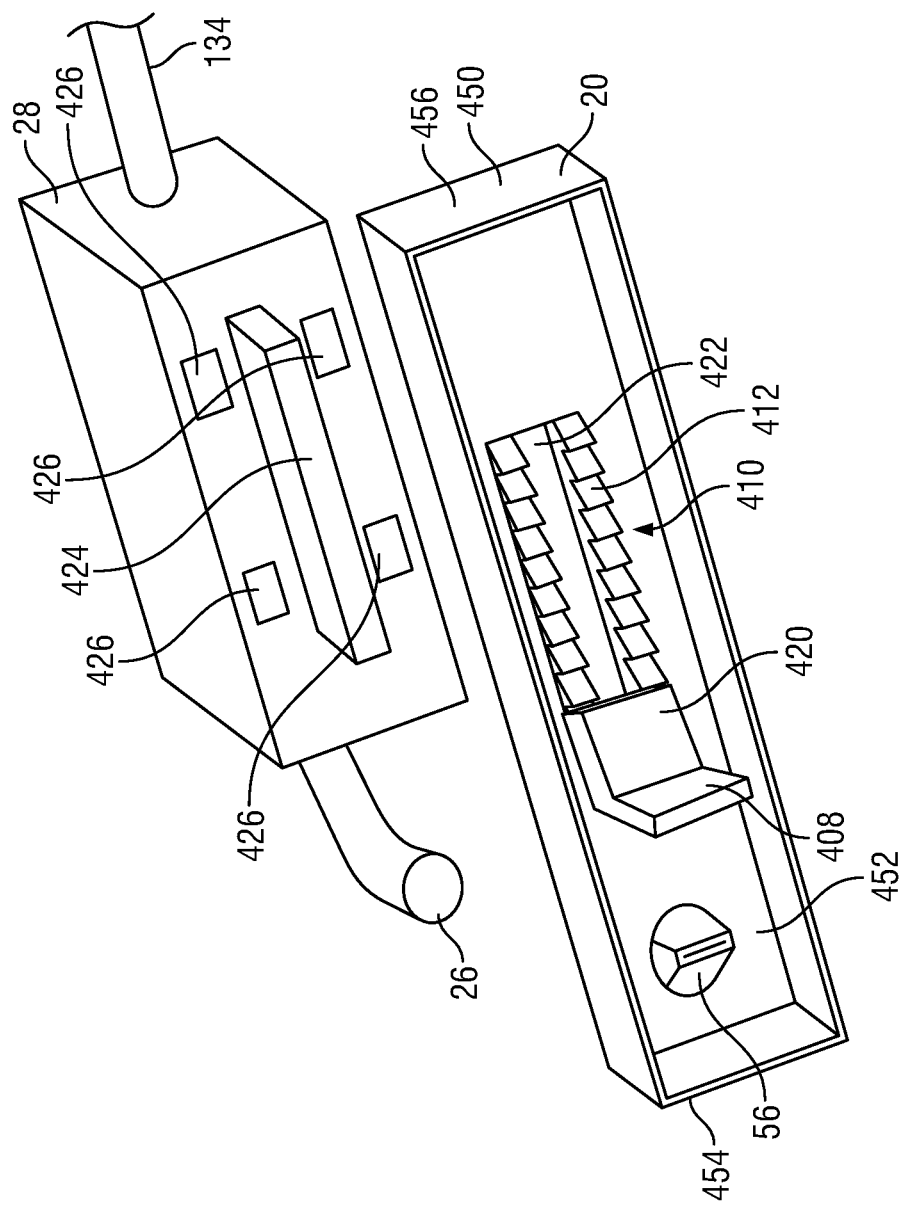
FIG. 36 shows a cross-sectional perspective view of the personal dispenser of FIG. 32 along sectional line E-E', with the personal dispenser in the uncoupled state.
Figure 37:
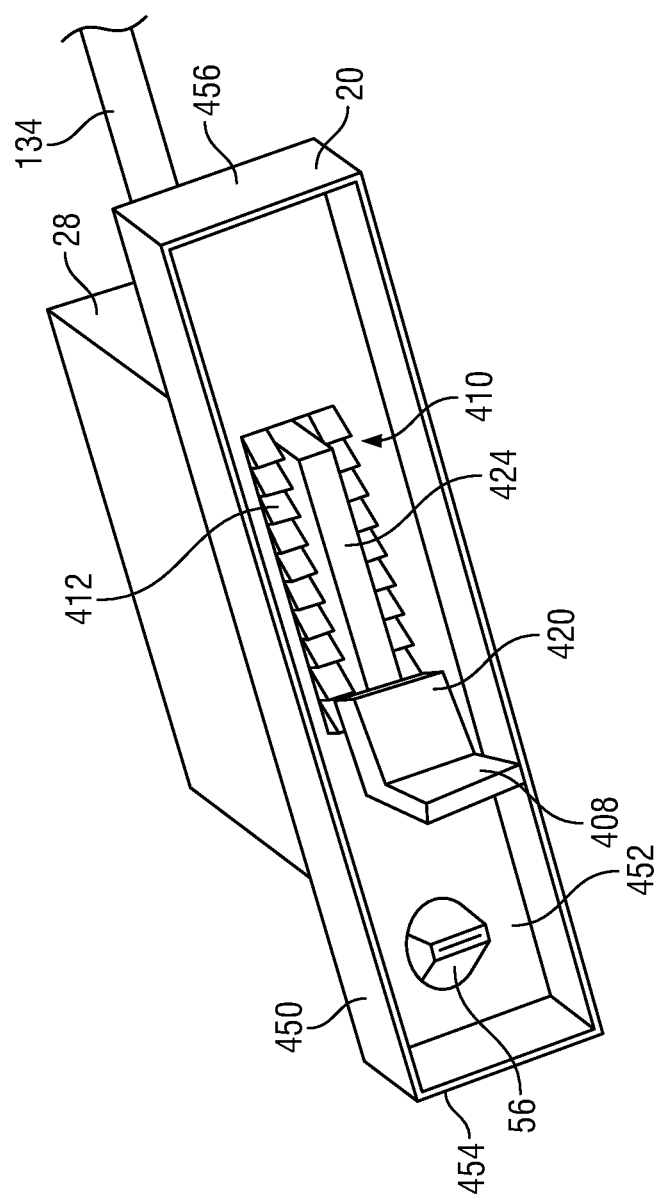
FIG. 37 shows a cross-sectional perspective view of the personal dispenser of FIG. 33 along sectional line F-F', with the personal dispenser in the coupled state.

FIGS. 36 and 37 illustrate the arrangement of the flexible pawl 408 relative to the rack 410 when uncoupled from the mounting dock 28 (FIG. 36), and when coupled to the mounting dock 28 (FIG. 37). To improve clarity, the bag 400 has been omitted from FIGS. 36 and 37. As can be seen in FIGS. 31 and 36, the top surface of the housing 450 has a centrally located mounting slot 422. The teeth 412 of the rack 410 are arranged longitudinally on either side of the mounting slot 422. The slot 422 is sized to receive an unlocking rib 424 of the mounting dock 28 therein. When the personal dispenser 20 is mounted to the mounting dock 28, the unlocking rib 424 is received within the mounting slot 422, and the rib 424 pushes the foot 420 of the flexible pawl 408 away from, and out of engagement with, the rack 410. This is shown in FIGS. 35 and 37 (in FIG. 35, the teeth 412 located behind the rib 424 are shown in dashed lines). With the foot 420 disengaged from the rack 410, the plunger body 406 is unlocked and can freely move toward the second end 456 of the housing 450. As such, it is possible to fill the bag 400 with further liquid while the personal dispenser 20 is mounted to the dock 28.

As shown in FIGS. 31 and 36, the personal dispenser 20 and the mounting dock 28 have a set of complimentary magnets 426 that align when the unlocking rib 424 of the mounting dock 28 is received within the mounting slot 422 of the personal dispenser 20. These magnets 426 hold the personal dispenser 20 and the mounting dock 28 together when coupled. It is to be appreciated, however, that any other suitable mounting mechanism could be used instead to hold the personal dispenser 20 and the mounting dock 28 together.

As in the previously described embodiments, when the personal dispenser 20 is mounted to the mounting dock 28, the outlet end 26 of the spout tube 134 is sealingly received within the inlet port 40 of the personal dispenser 20. Liquid is pumped into the bag 400 of the personal dispenser 20 by activating the pump assembly 16 of the master dispenser 10, as in the previously described embodiments. The liquid enters the personal dispenser 20 via the inlet port 40, and fills up the bag 400. As the bag 400 fills, it expands longitudinally, pushing the plunger body 406 toward the second end 456 of the housing 450. Once the bag 400 has reached its maximum capacity, any further liquid that is pumped into the bag 400 increases the internal pressure therein. Once the threshold pressure is reached, pumping further liquid into the bag 400 forces an allotment of liquid through the one-way outlet valve 66 of the outlet port 42.

As in the previously described embodiments, the personal dispenser 20 can be removed from the master dispenser 10, and used to provide a supply of the liquid at another location. The liquid within the bag 400 is discharged from the outlet port 42 by pushing the push button 416 toward the first end 454 of the housing 450, in the manner as described above. The personal dispenser 20 can then be refilled as needed by mounting it to the master dispenser 10, and activating the pump assembly 16.

The inventors have appreciated that this construction of the personal dispenser 20 reduces or eliminates contact between the liquid received by the personal dispenser 20 and atmospheric air. In particular, the bag 400 simply expands as it fills with liquid, and there is no air contained therein that needs to be expelled to accommodate the liquid. Furthermore, when the liquid is expelled from the outlet port 42, the bag 400 simply collapses, and there is no need to take in air to replace the discharged liquid.

As such, with this construction of the personal dispenser 20, liquid can be pumped directly from the master dispenser 10 into the personal dispenser 20 without contacting atmospheric air. This reduces the risk of the liquid becoming contaminated by air borne contaminants, including air borne bacteria such as *Legionella*.

Preferably, the master dispenser 10 is also configured to eliminate contact between the liquid and atmospheric air, to further reduce the risk of contamination. For example, the reservoir 12 is preferably designed to collapse as liquid is discharged therefrom, instead of taking in atmospheric air to replace the discharged liquid. The sealing engagement between the outlet end 26 of the spout tube 134 and the inlet port 40 furthermore prevents the liquid from contacting atmospheric air as it is transferred from the spout tube 134 to the personal dispenser 20.

During manufacturing, the housing 450 of the personal dispenser 20 is optionally constructed from separate top 470 and bottom 472 halves. While the top 470 and bottom 472 halves are detached from one another, the internal cavity 452 is easily accessible so that the internal components of the personal dispenser 20 can be arranged therein. For example, the bag 400 can be placed between the top 470 and bottom 472 halves of the housing 450, so that the bag 400 will sit within the internal cavity 452 once the two halves 470, 472 of the housing 450 are attached together. The plunger body 406 can also be put in place, with the push button 416 arranged on the outer surface of the bottom half 472 of the housing 450, and the connecting body 414 positioned so that it will sit within the side slot 418 once the top half 470 is attached. Once the internal components are in place, the top 470 and bottom 472 halves can be securely attached to one another using glue, heat bonding, snap connections, or any other suitable bonding or attachment techniques.

The reservoir 12 is preferably made from plastic, although any other suitable materials that would adequately contain the liquid could be used instead, such as, in some embodiments of the invention, metal. The liquid is preferably hand soap or hand sanitizer, although other liquids such as hand lotion or sunscreen could be used as desired. Preferably, the reservoir 12 is sized to contain 250 to 5000 ml of the liquid, and more preferably 500 to 2000 ml, although any other desired size could be used instead.

The receptacle 38 is preferably formed from molded plastic, though any other suitable materials could be used instead. Preferably, the receptacle 38 is sized to contain between 10 ml and 80 ml of the liquid, and more preferably between 20 ml and 60 ml, or between 20 ml and 25 ml, although any other desired size could be used. The receptacle 38 may be fully or partially transparent, to permit visual assessment of the volume of the liquid contained therein.

While the preferred embodiments have described the pump assembly 16 as a piston pump, it is to be appreciated that any suitable pump construction could be used including, for example, different positive displacement pumps, gear pumps, plunger pumps, and hydraulic pumps. Furthermore, the invention is not limited to the specific valve constructions that have been depicted and described.

While the preferred embodiments have been described as incorporating particular sensor types, it is to be appreciated that many other sensor types could be used to achieve the desired functionality including, for example, devices that sense mass, motion, temperature, position, electrical properties, magnetic properties, optical properties, or any other detectable properties.

In the first embodiment of the invention described above, preferably the width of the elongated dovetail shaped projection 36 at the front end 32 of the elongated dovetail shaped projection 36 is approximately equal to the width of the elongated dovetail shaped channel 52 at the front end 46 of the elongated dovetail shaped channel 52; and a width of the elongated dovetail shaped projection 36 immediately adjacent to the front end 32 of the elongated dovetail shaped projection 36 is greater than the width of the elongated dovetail shaped channel 52 at the front end 46 of the elongated dovetail shaped channel 52. Also, the width of the elongated dovetail shaped projection 36 at the back end 34 of the elongated dovetail shaped projection 36 is greater than the width of the elongated dovetail shaped channel 52 at the front end of the elongated dovetail shaped channel 52; and the width of the elongated dovetail shaped channel 52 at the back end 48 of the elongated dovetail shaped channel 52 is greater than the width of the elongated dovetail shaped projection 36 at the front end 32 of the elongated dovetail shaped projection 36.

It is to be appreciated that the term "personal dispenser" 20 as used herein is intended to include within its scope mobile dispensing devices that are used by multiple individuals, as well as mobile dispensing devices that may be used by only a single individual. For example, the personal dispenser 20 could be positioned at a point of care, such as at a patient's bedside, where it is available to dispense the liquid to any healthcare worker that visits the patient. The term "personal" is not intended to, in any way, limit the scope of the personal dispenser 20 of the present invention to dispensing devices that are only used by a single user.

As used herein, the term "liquid" is intended to refer broadly to any flowable and relatively dense substance including, for example, gels, creams, foams, and flowable composite materials.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments which are functional or mechanical equivalents of the specific embodiments and features that have been described and illustrated herein.

We claim:

1. A replaceable cartridge for a liquid master dispenser, comprising:
   a reservoir for containing liquid to be dispensed from the liquid master dispenser; and
   a personal dispenser removably coupled to the reservoir, the personal dispenser comprising:
   a receptacle for containing liquid to be dispensed from the personal dispenser; and
   an outlet port for discharge of the liquid from the receptacle;
   wherein the personal dispenser is configured for selectively discharging the liquid contained in the receptacle from the outlet port, after the personal dispenser is removed from the reservoir.

2. The replaceable cartridge according to claim 1, wherein the reservoir has a cavity sized for removably receiving the personal dispenser.

3. The replaceable cartridge according to claim 2, wherein the personal dispenser is held within the cavity of the reservoir in an initial bundled configuration.

4. The replaceable cartridge according to claim 3, further comprising a label that is secured to a face of the reservoir and a face of the personal dispenser while in the initial bundled configuration;
   wherein the label is configured to be severed upon removal of the personal dispenser from the cavity, so as to leave a first portion of the label secured to the face of the reservoir and a second portion of the label secured to the face of the personal dispenser.

5. The replaceable cartridge according to claim 2, wherein the personal dispenser is held within the cavity of the reservoir, without protruding from the cavity, when in an initial bundled configuration.

6. The replaceable cartridge according to claim 5, wherein the reservoir has a face in which the cavity is formed, and the personal dispenser has a face that is substantially flush with the face of the reservoir when in the initial bundled configuration.

7. The replaceable cartridge according to claim 6, wherein the replaceable cartridge has a substantially flat profile when in the initial bundled configuration.

8. The replaceable cartridge according to claim 2, wherein the reservoir has at least one indentation adjacent to the cavity.

9. The replaceable cartridge according to claim 8, wherein the at least one indentation is configured to provide manual access for removal of the personal dispenser from the cavity.

10. The replaceable cartridge according to claim 9, wherein the at least one indentation comprises two indentations that are provided on opposite sides of the cavity, the two indentations being sized and spaced to allow a user to grasp and remove the personal dispenser from the cavity.

11. The replaceable cartridge according to claim 2, wherein the reservoir comprises:
    a top wall with an outlet opening;
    a bottom wall; and
    a side wall that connects the top wall and the bottom wall;
    wherein the cavity is formed as a recess in the side wall.

12. The replaceable cartridge according to claim 1, wherein the reservoir is formed from plastic.

13. The replaceable cartridge according to claim 3, wherein the reservoir has a reservoir outlet for selective discharge of the liquid from the reservoir;
    wherein the personal dispenser has an inlet port for receiving the liquid discharged from the reservoir outlet and communicating the liquid to the receptacle;
    wherein the personal dispenser is configured to sealingly engage with the reservoir outlet so that the liquid discharged from the reservoir outlet accumulates in the receptacle, the personal dispenser being selectively removable from the reservoir outlet;
    wherein the inlet port comprises a one-way inlet valve that permits fluid to enter the receptacle through the inlet port, and prevents fluid from exiting the receptacle through the inlet port; and
    wherein the receptacle defines an internal volume and is compressible to selectively reduce the internal volume from an uncompressed volume to a compressed volume upon application of a compressing force, to thereby discharge the liquid from the outlet port.

14. The replaceable cartridge according to claim 1, wherein the liquid to be dispensed from the master liquid dispenser and the liquid to be dispensed from the personal dispenser comprises a hand cleaner.

15. A liquid dispenser, comprising:
    a reservoir for containing liquid to be dispensed;
    a dispenser outlet for discharge of the liquid from the reservoir;
    a discharge mechanism operable to discharge the liquid from the dispenser outlet when activated;
    a refill outlet configured to couple with a personal dispenser and deliver the liquid from the reservoir to the personal dispenser; and
    a filling mechanism operable to deliver the liquid from the refill outlet when activated;
    wherein the dispenser outlet is separate from the refill outlet.

16. The liquid dispenser according to claim 15, further comprising a valve arrangement for directing the liquid from the reservoir to the dispenser outlet or the refill outlet, wherein the valve arrangement is configured to:
    permit the liquid to flow from the reservoir to the refill outlet, and prevent the liquid from flowing from the reservoir to the dispenser outlet, when the personal dispenser is coupled to the refill outlet and contains less than a preselected volume of the liquid;
    permit the liquid to flow from the reservoir to the dispenser outlet, and prevent the liquid from flowing from the reservoir to the refill outlet, when the personal dispenser is coupled to the refill outlet and contains the preselected volume of the liquid; and
    permit the liquid to flow from the reservoir to the dispenser outlet, and prevent the liquid from flowing from the reservoir to the refill outlet, when the personal dispenser is uncoupled from the refill outlet.

17. The liquid dispenser according to claim 15, further comprising a conduit for conveying the liquid from the reservoir to the dispenser outlet or the refill outlet, the conduit having a conduit inlet in fluid communication with the reservoir and a conduit outlet;
    wherein the dispenser outlet and the refill outlet are rotatably mounted relative to the conduit outlet for selectively alternating between a dispensing condition, wherein the dispenser outlet is aligned with and in fluid communication with the conduit outlet, and a refill condition, wherein the refill outlet is aligned with and in fluid communication with the conduit outlet.

18. The liquid dispenser according to claim 15, further comprising a usage monitoring system configured to generate information indicative of an amount of the liquid dispensed from the liquid dispenser, wherein said amount includes both the liquid dispensed from the dispenser outlet and the liquid delivered to the personal dispenser from the refill outlet;

wherein the usage monitoring system comprises at least one of:

a sensor configured to detect a volume or a mass of the liquid contained in the reservoir;

a sensor configured to detect a flow of the liquid through the dispenser outlet;

a sensor configured to detect a flow of the liquid through the refill outlet;

a sensor configured to detect the activation of the discharge mechanism; and a sensor configured to detect the activation of the filling mechanism.

19. The liquid dispenser according to claim 15, further comprising:

a sensor configured to detect if the personal dispenser is coupled to the refill outlet; and a sensor configured to detect if the personal dispenser is full;

wherein the filling mechanism is configured to automatically deliver the liquid from the refill outlet to the personal dispenser, when the personal dispenser is coupled to the refill outlet; and wherein the filling mechanism is configured to automatically stop delivery of the liquid from the refill outlet to the personal dispenser, when the personal dispenser is full.

20. The liquid dispenser according to claim 15, wherein the liquid comprises a hand cleaner.

* * * * *